(12) United States Patent
Ismagilov et al.

(10) Patent No.: US 11,278,898 B2
(45) Date of Patent: Mar. 22, 2022

(54) METHOD FOR CONDUCTING AN AUTOCATALYTIC REACTION IN PLUGS IN A MICROFLUIDIC SYSTEM

(71) Applicant: The University of Chicago, Chicago, IL (US)

(72) Inventors: Rustem F. Ismagilov, Chicago, IL (US); Joshua David Tice, Chicago, IL (US); Cory John Gerdts, Chicago, IL (US); Bo Zheng, Chicago, IL (US)

(73) Assignee: The University of Chicago, Chicago, IL (US)

( * ) Notice: Subject to any disclaimer, the term of this patent is extended or adjusted under 35 U.S.C. 154(b) by 214 days.

(21) Appl. No.: 15/926,988

(22) Filed: Mar. 20, 2018

(65) Prior Publication Data
US 2018/0304268 A1 Oct. 25, 2018

Related U.S. Application Data

(63) Continuation of application No. 15/087,176, filed on Mar. 31, 2016, which is a continuation of application
(Continued)

(51) Int. Cl.
*B01L 3/00* (2006.01)
*B01F 5/06* (2006.01)
(Continued)

(52) U.S. Cl.
CPC ...... *B01L 3/502784* (2013.01); *B01D 9/0072* (2013.01); *B01F 5/0646* (2013.01);
(Continued)

(58) Field of Classification Search
CPC .. B01F 13/0071; B01F 5/0646; B01F 5/0647; B01F 2215/0037; B01F 3/0861; B01F 5/0403; B01J 19/0046; B01J 19/0093; B01J 14/00; B01L 2200/0673; B01L 2300/0867; B01L 3/502784; G01N 35/08;
(Continued)

(56) References Cited

U.S. PATENT DOCUMENTS 3,960,187 A 6/1976 Stock et al.
4,853,336 A 8/1989 Saros et al.
(Continued)

FOREIGN PATENT DOCUMENTS

CN 2482070 Y 3/2002
EP 0912238 A1 5/1999
(Continued)

OTHER PUBLICATIONS

Stroock, Abraham D. et al., "Chaotic Mixer for Microchannels", Science, vol. 295, pp. 647-651, 2002.
(Continued)

*Primary Examiner* — Lyle Alexander
*Assistant Examiner* — Bryan Kilpatrick
(74) *Attorney, Agent, or Firm* — Brown Rudnick LLP; Thomas C. Meyers

(57) ABSTRACT

The present invention provides microfabricated substrates and methods of conducting reactions within these substrates. The reactions occur in plugs transported in the flow of a carrier-fluid.

17 Claims, 40 Drawing Sheets

Related U.S. Application Data

No. 13/024,165, filed on Feb. 9, 2011, now Pat. No. 9,329,107, which is a continuation of application No. 12/777,099, filed on May 10, 2010, now abandoned, which is a continuation of application No. 10/765,718, filed on Jan. 26, 2004, now Pat. No. 7,901,939, which is a continuation-in-part of application No. 10/434,970, filed on May 9, 2003, now Pat. No. 7,129,091.

(60) Provisional application No. 60/394,544, filed on Jul. 8, 2002, provisional application No. 60/379,927, filed on May 9, 2002.

(51) Int. Cl.

| | | |
|---|---|---|
| B01F 13/00 | (2006.01) | |
| B01J 19/00 | (2006.01) | |
| B82Y 30/00 | (2011.01) | |
| G01N 35/08 | (2006.01) | |
| G01N 1/28 | (2006.01) | |
| B01D 9/00 | (2006.01) | |
| C07K 14/43 | (2006.01) | |
| C12N 9/36 | (2006.01) | |
| C30B 7/14 | (2006.01) | |
| C30B 29/54 | (2006.01) | |
| C30B 29/58 | (2006.01) | |
| B01J 14/00 | (2006.01) | |
| C12Q 1/6806 | (2018.01) | |

(52) U.S. Cl.
CPC ........ *B01F 5/0647* (2013.01); *B01F 13/0071* (2013.01); *B01J 14/00* (2013.01); *B01J 19/0046* (2013.01); *B01J 19/0093* (2013.01); *B01L 3/50273* (2013.01); *B01L 3/502715* (2013.01); *B82Y 30/00* (2013.01); *C07K 14/43* (2013.01); *C12N 9/2462* (2013.01); *C12Q 1/6806* (2013.01); *C30B 7/14* (2013.01); *C30B 29/54* (2013.01); *C30B 29/58* (2013.01); *G01N 1/28* (2013.01); *G01N 35/08* (2013.01); *B01D 2009/0086* (2013.01); *B01J 2219/0086* (2013.01); *B01J 2219/00286* (2013.01); *B01J 2219/00576* (2013.01); *B01J 2219/00585* (2013.01); *B01J 2219/00599* (2013.01); *B01J 2219/00722* (2013.01); *B01J 2219/00725* (2013.01); *B01J 2219/00736* (2013.01); *B01J 2219/00756* (2013.01); *B01J 2219/00783* (2013.01); *B01J 2219/00837* (2013.01); *B01J 2219/00869* (2013.01); *B01J 2219/00889* (2013.01); *B01J 2219/00891* (2013.01); *B01J 2219/00894* (2013.01); *B01J 2219/00903* (2013.01); *B01J 2219/00975* (2013.01); *B01J 2219/00977* (2013.01); *B01L 2200/0673* (2013.01); *B01L 2200/12* (2013.01); *B01L 2300/0867* (2013.01); *B01L 2400/0487* (2013.01); *C12Y 302/01017* (2013.01); *Y10T 117/10* (2015.01); *Y10T 137/0318* (2015.04); *Y10T 436/117497* (2015.01); *Y10T 436/143333* (2015.01); *Y10T 436/25* (2015.01)

(58) Field of Classification Search
CPC ............ G01N 15/1484; G01N 35/085; C12Q 1/6806; Y10T 436/117497; Y10T 436/118339; Y10T 436/2575
See application file for complete search history.

(56) References Cited

U.S. PATENT DOCUMENTS

| | | |
|---|---|---|
| 4,963,498 A | 10/1990 | Hillman et al. |
| 5,185,099 A | 2/1993 | Delpuech et al. |
| 5,739,036 A | 4/1998 | Parris |
| 5,800,690 A | 9/1998 | Chow et al. |
| 5,842,787 A | 12/1998 | Kopf-Sill et al. |
| 5,872,010 A | 2/1999 | Karger et al. |
| 5,876,675 A | 3/1999 | Kennedy |
| 5,887,755 A | 3/1999 | Hood, III |
| 5,948,684 A | 9/1999 | Weigl et al. |
| 5,997,636 A | 12/1999 | Gamarnik et al. |
| 6,010,607 A | 1/2000 | Ramsey |
| 6,068,752 A | 5/2000 | Dubrow et al. |
| 6,118,849 A | 9/2000 | Tanimori et al. |
| 6,130,098 A | 10/2000 | Handique et al. |
| 6,140,053 A | 10/2000 | Koster |
| 6,180,372 B1 | 1/2001 | Franzen |
| 6,296,673 B1 | 10/2001 | Santarsiero et al. |
| 6,409,832 B2 * | 6/2002 | Weigl ............... B01F 13/0093 117/200 |
| 6,569,631 B1 | 5/2003 | Pantoliano et al. |
| 6,630,006 B2 | 10/2003 | Santarsiero et al. |
| 6,656,267 B2 | 12/2003 | Newman |
| 6,766,817 B2 | 7/2004 | da Silva |
| 6,790,328 B2 | 9/2004 | Jacobson et al. |
| 6,797,056 B2 | 9/2004 | David |
| 6,872,250 B2 | 3/2005 | David et al. |
| 7,041,481 B2 | 5/2006 | Anderson et al. |
| 7,129,091 B2 | 10/2006 | Ismagilov et al. |
| 7,156,917 B2 | 1/2007 | Moriyama et al. |
| 7,294,503 B2 | 11/2007 | Quake et al. |
| RE43,122 E | 1/2012 | Harrison et al. |
| 8,273,573 B2 | 9/2012 | Ismagilov et al. |
| 8,329,407 B2 | 12/2012 | Ismagilov et al. |
| 9,579,622 B2 | 2/2017 | Ismagilov et al. |
| 2001/0048900 A1 | 12/2001 | Bardell et al. |
| 2002/0012971 A1 | 1/2002 | Mehta |
| 2002/0029814 A1 | 3/2002 | Unger et al. |
| 2002/0058332 A1 | 5/2002 | Quake et al. |
| 2002/0067800 A1 | 6/2002 | Newman et al. |
| 2003/0061687 A1 | 4/2003 | Hansen et al. |
| 2003/0064414 A1 | 4/2003 | Benecky et al. |
| 2003/0229376 A1 | 12/2003 | Sandhu |
| 2004/0005582 A1 | 1/2004 | Shipwash |
| 2004/0037739 A1 | 2/2004 | McNeely et al. |
| 2004/0037813 A1 | 2/2004 | Simpson et al. |
| 2004/0136497 A1 | 7/2004 | Meldrum et al. |
| 2004/0181131 A1 | 9/2004 | Maynard et al. |
| 2004/0224419 A1 | 11/2004 | Zheng et al. |
| 2004/0258203 A1 | 12/2004 | Yamano et al. |
| 2005/0048561 A1 | 3/2005 | Fulwyler et al. |
| 2005/0087122 A1 * | 4/2005 | Ismagliov ............... G01N 35/08 117/2 |
| 2005/0170431 A1 | 8/2005 | Ibrahim et al. |
| 2006/0094119 A1 | 5/2006 | Ismagilov et al. |
| 2006/0257893 A1 | 11/2006 | Takahashi et al. |
| 2007/0026439 A1 | 2/2007 | Faulstich et al. |
| 2009/0021728 A1 | 1/2009 | Heinz et al. |
| 2009/0060797 A1 | 3/2009 | Mathies et al. |
| 2010/0022414 A1 | 1/2010 | Link et al. |

FOREIGN PATENT DOCUMENTS

| | | | |
|---|---|---|---|
| EP | 1871903 A2 | 1/2008 | |
| GB | 2 097 692 A | 11/1982 | |
| GB | 2097692 A * | 11/1982 | ............ B01F 5/0403 |
| WO | 84/02000 | 5/1984 | |
| WO | 9802237 A1 | 1/1998 | |
| WO | 9852691 A1 | 11/1998 | |
| WO | 0112327 A1 | 2/2001 | |
| WO | 0164332 A1 | 9/2001 | |
| WO | 02/23163 | 3/2002 | |
| WO | 02/23163 A1 | 3/2002 | |

(56) References Cited

FOREIGN PATENT DOCUMENTS

| WO | 2004/038363 | 5/2004 |
|---|---|---|
| WO | 2006/101851 A2 | 9/2006 |

OTHER PUBLICATIONS

Sugiura, Shinji et al., "Effect of Channel Structure on MicroChannel Emulsification", Langmuir, vol. 18, pp. 5708-5712, 2002.
Takayama et al., Patterning Cells and Their Environments Using Multiple Laminar Fluid Flows in Capillary Networks, Proc. Natl. Acad. Sci. USA, vol. 96, pp. 5545-5548, 1999.
Taniguchi, Tomohiro et al., "Chemical Reactions in Microdroplets by Electrostatic Manipulation of Droplets in Liquid Media", Lab on a Chip, vol. 2, pp. 19-23, 2002.
Thorsen et al., "Microfluidic Large-Scale Integration", Science, vol. 298, pp. 580-584, 2002.
Thorsen, Todd et al., "Dynamic Pattern Formation in a Vesicle-Generating Microfluidic Device", Physical Review Letters, vol. 86, No. 18, pp. 4163-4166, 2001.
Tice et al. "Formation of Droplets and Mixing in Multiphase Microfluidics at Low Values of the Reynolds and the Capillary Numbers", Langmuir, vol. 19, pp. 9127-9133, 2003.
Tice, "Effects of Viscosity on Droplet Formation and Mixing in Microfluidic Channels", Analytica Chimica Acta, vol. 507, pp. 73-77, 2004.
Titomanlio et at, Capillary experiments of flow induced crystallization of HDPF', AlChe Journal, 1990, v36, No. 1, pp. 13-18.
Tokeshi, Manabu et al., "Continuous-Flow Chemical Processing on a Microchip by Combining Microunit Operations and Multiphase Flow Network", Analytical Chemistry, vol. 74, No. 7, pp. 1565-1571, 2002.
Torkkeli A. et al., "Droplet Manipulation on a Superhydrophobic Surface for Microchemical Analysis", 11th International Conference on Solid-State Sensors and Actuators. Digest of Technical Papers, Munich, Jun. 10-14, 2001; vol. 2, pp. 1150-1153.
Umbanhowar, P.B. et al., "Monodisperse Emulsion Generation via Drop Break Off in a Coflowing Stream", Langmuir, vol. 16, pp. 347-351, 2000.
Wang, Hongzhi et al., "Preparation of Titania Particles Utilizing the Insoluble Phase Interface in a MicroChannel Reactor", Chemical Communications, pp. 1462-1463, 2002.
Zhao, Bin et al., "Control and Applications of Immiscible Liquids in Microchannels", J. Am. Chem. Soc., vol. 124, pp. 5284-5285, 2002.
Zheng et al., "A Droplet-Based, Composite PDMS/Glass Capillary Microfluidic System for Evaluating Protein Crystallization Conditions by Microbatch and Vapor-Diffusion Methods with On-Chip X-Ray Diffraction", Angew. Chem., pp. 1-4, 2004.
Zheng et al., "Formation of Droplets of Alternating Composition in Microfluidic Channels and Applications to Indexing of Concentrations in Droplet-Based Assays", Anal. Chem., 2004, v. 76, p. 4977-4982.
Zheng et al., "Screening of Protein Crystallization Conditions on a Microfluidic Chip Using Nanoliter Size Droplets", Journal of the American Chemical Society, vol. 125, No. 37, p. 11170-11171, 2003.
Auroux, Pierre-Alain et al., "Micro Total Analysis Systems. 2. Analytical Standard Operations and Applications", Analytical Chemistry, vol. 74, No. 12, 2002, pp. 2637-2652.
Anna, Shelley A. et al., "Formation of Dispersions Using 'Flow Focusing' in Microchannels", Applied Physics Letters, vol. 82, No. 3, 2003, pp. 364-366.
Atencia, Javier, et al. "Controlled Microfluidic Interfaces", Nature, 2005, vol. 437, No. 29, pp. 648-655.
Beer et al., 2007, On-Chip, Real-Time, Single-Copy Polymerase Chain Reaction in Picoliter Droplets, Anal. Chem., 79:847-8475.
Bico, Jose et al., "Rise of Liquids and Bubbles in Angular Capillary Tubes", Journal of Colloid and Interface Science, vol. 247, pp. 162-166, 2002.

Bringer et al., "Microfluidic Systems for Chemical Kinetics That Rely on Chaotic Mixing in Droplets", Phil. Trans. R. Soc. Lond., pp. 1-18, 2004.
Burns et al., "Microfabricated structures for integrated DNA analysis", Proc. Natl. Acad. Sci. USA, May 1996, vol. 93, pp. 5556-5561.
Burns, J.R. et al., "The Intensification of Rapid Reactions in Multiphase Systems Using Slug Flow in Capillaries", Lab on a Chip, vol. 1, pp. 10-15, 2001.
Burns, Mark et al., "An Integrated Nanoliter DNA Analysis Device", Science, vol. 282, pp. 484-487, 1998.
Chan, Emory M. et al., "Size-Controlled Growth of CdSe Nanocrystals in Microfluidic Reactors", Nano Letters, vol. 3, No. 2, pp. 199-201, 2003.
Chayen, N.E., "Crystallization with oils: a new dimension in macromolecular crystal growth", Journal of Crystal Growth 196 (1999), pp. 434-441.
Cho, Sung Kwon et al., "Splitting a Liquid Droplet for Electrowetting-Based Microfluidics", Proceedings of 2001 ASME International Mechanical Engineering Congress and Exposition, pp. 1-7, 2001.
De-Bashan et al., 2002, "Removal of ammonium and phosphorus ions from synthetic wastewater by the microalgae Chlorella vulgaris coimmobilized in alginate beads with the microalgae growth-promoting bacterium Azospirillum brasilense", Water Research 36:2941-2948.
Duffy, David C. et al., "Rapid Prototyping of Microfluidic Systems in Poly(dimethylsiloxane)", Analytical Chemistry, vol. 70, pp. 4974-4984, 1998.
Edel, Joshua B. et al., "Microfluidic Routes to the Controlled Production of Nanoparticles", Chemical Communications, pp. 1136-1137, 2002.
Eggers, Jens et al., "Coalescence of Liquid Drops", J. Fluid Mech., vol. 401, pp. 293-310, 1999.
Fowler, Jesse et al., "Enhancement of Mixing By Droplet-Based Microfluids", 2002 Institute of Electrical Engineers 1& International Conference on Micro Electro Mechanical Systems, pp. 97-100, 2002.
Garcia-Ruiz et at "A super-saturation wave of protein crystallization", J. Crystal Growth, 2001, v232, pp. 149-155.
Garcia-Ruiz et at, Investigation on protein crystal growth by the gel acupuncture method, Acta, Cryst., 1994, D50, 99. pp. 484-490.
Goodall, J. L. et at, "Operation of Mixed-Culture Immobilized Cell Reactors for the Metabolism of Meta- and Para-Nitrobenzoate by *Comamonas* Sp. JS46 and *Comamonas* Sp. JS47", Biotechnology and Bioengineering, vol. 59, No. 1, Jul. 5, 1998, pp. 21-27.
Gu, Hao, et al., "Droplets Formation and Merging in Two-Phase Flow Microfluidics", Int. J. Mol. Sci., 2011, vol. 12, pp. 2572-2597.
He, Mingyan et at, "Selective Encapsulation of Single Cells and Subcellular Organelles into Picoliter- and Femtoliter-Volume Droplets", Analytical Chemistry, vol. 77, No. 6, Mar. 15, 2005, pp. 1539-1544.
Huebner, A. et at, "Quantitative detection of protein expression in single cells using droplet microfluidics", Chem. Commun, 2007, pp. 1218-1220.
Kopp, M.U. et al., Chemical Amplification: Continuous-Flow PCR on a Chip, Science, 1998, vol. 280, pp. 1046-1048.
Nisisako, T. et at, Formation of Droplets Using Branch Channels in a Microfluidic Circuit, SICE 2002, Aug. 5-7, 2002, Osaka, pp. 1262-1264.
Pollack et al., "Electrowetting-based actuation of droplets for integrated microfluidics", Lab Chip, 2002, v. 2, pp. 96-101.
Thorsen et al., 2001, Dynamic Pattern Formation in a Vesicle-Generating Microfluidic Device, Phys. Rev. Lett., 86 (18):4163-4166.
Tanaka et al., 1986, "Ethanol Production from Starch by a Coimmobilized Mixed Culture System of Aspergillus awamori and Zymomonas mobilis", Biotechnology and Bioengineering, XXVII:1761-1768.
Seong G.H. et at, "Efficient Mixing and reactions within Microfluidic Channels Using Microbead-Supported Catalysts", J. Am. Chem. Soc. 2002, 124, p. 13360-13361.
Seong, G.H. et at, "Fabrication of Microchambers Defined by Photopolymerized Hydrogels and Weirs within Microfluidic Sys-

(56) References Cited

OTHER PUBLICATIONS tems: Application to DNA Hybridization", Analytical Chemistry, vol. 74, No. 14, Jul. 15, 2002, pp. 3372-3377.

Sugiura et at, "Interfacial tension driven monodispersed droplet formation from microfabricated channel array", Langmuir, 2001, v17, pp. 5562-5566.

Vogelstein, et al., "Digital PCR", Proc. Natl. Acad. Sci. USA, Aug. 1999, vol. 96, pp. 9236-9241, Genetics.

Gerdts et al., "A Synthetic Reaction Network: Chemical Amplification Using Nonequilibrium Autocatalytic Reactions Coupled in Time", J. Am. Chem. Soc., vol. 126, pp. 6327-6331, 2004.

Handique, K et al., "On-Chip Thermopneumatic Pressure for Discrete Drop Pumping", Analytical Chemistry, vol. 73, pp. 1831-1838, 2001.

Hansen, Carl L. et al., "A Robust and Scalable Microfluidic Metering Method That Allows Protein Crystal Growth by Free Interface Diffusion", PNAS, vol. 99, No. 26, p. 16531-16536, 2002.

Harries, N. et al., "A Numerical Model for Segmented Flow in a Microreactor", International Journal of Heat and Mass Transfer, vol. 46, pp. 3313-3322, 2003.

Hosokawa, Kazuo et al., "Handling of Picoliter Liquid Samples in a Poly(dimethylsiloxane)-Based Microfluidic Device", Analytical Chemistry, vol. 71, No. 20, pp. 4781-4785, 1999.

Ismagilov, "Integrated Microfluidic Systems", Angew. Chem. Int. Ed., vol. 42, pp. 4130-4132, 2003.

Liu, Robin H. et al., "Passive Mixing in a Three-Dimensional Serpentine MicroChannel", Journal of Microelectromechanical Systems, vol. 9, No. 2, pp. 190-197, 2000.

McDonald J. Cooper et al., "Fabrication of Microfluidic Systems in Poly(dimethylsiloxane)", Electrophoresis, vol. 21, pp. 27-40, 2000.

Ng et at, "Protein crystallization by capillary counter-diffusion for applied crystallographic structure determination", J. Struct. Biol. 2003, v142, pp. 218-231.

Nisisako, Takasi et al., "Droplet Formation in a MicroChannel Network", Lab on a Chip, vol. 2, pp. 24-26, 2002.

Pabit, Suzette A. et al., "Laminar-Flow Fluid Mixer for Fast Fluorescence Kinetics Studies", Biophysical Journal, vol. 83, pp. 2872-2878, 2002.

Peng, Shuangjiu et al., "Controlled Production of Emulsions Using a Crossflow Membrane", Particle & Particle Systems Characterization, vol. 15, pp. 21-25, 1998.

Reyes, Darwin R. et al., "Micro Total Analysis Systems. 1. Introduction, Theory and Technology", Analytic Chemistry, vol. 74, No. 12, pp. 2623-2636, 2002.

Shestopalov, Ilya, et al., "Multi-Step Synthesis of Nanoparticles Performed on Millisecond Time Scale in a Microfluidic Droplet-Based System", Lab-Chip, 2004, vol. 4, pp. 316-321.

Song et al., "A Microfluidic System for Controlling Reaction Networks in Time", Angew. Chem. Int. Ed., vol. 42, No. 7, pp. 768-772, 2003.

Song et al., "Experimental Test of Scaling of Mixing by Chaotic Advection in Droplets Moving Through Microfluidic Channels", Applied Physics Letters, vol. 83, No. 22, pp. 4664-4666, 2003.

Song et al., "Millisecond Kinetics on a Microfluidic Chip Using Nanoliters of Reagents", J. Am. Chem. Soc., vol. 125, pp. 14613-14619, 2003.

Song, Helen et al., "A Microfluidic System for Controlling Reaction Networks in Time", Angew. Chem. Int. Ed., vol. 42, No. 7, pp. 768-772, 2003.

Extended European Search Report issued in European Application No. 20171949.9, dated Dec. 15, 2020, 7 pages.

Office Action issued in European Patent Application No. 10183131.1, dated Feb. 11, 2021, 8 pages.

\* cited by examiner

FIG. 14A(i)  FIG. 14A(ii)  FIG. 14A(iii)

FIG. 14B(i)  FIG. 14B(ii)  FIG. 14B(iii)

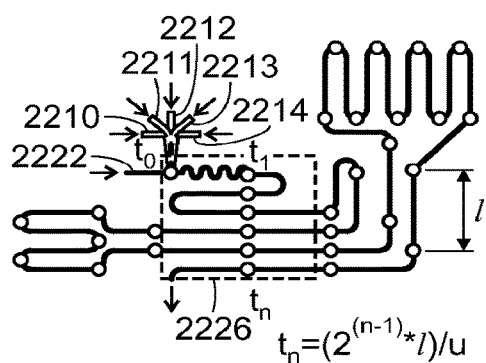
FIG. 22C
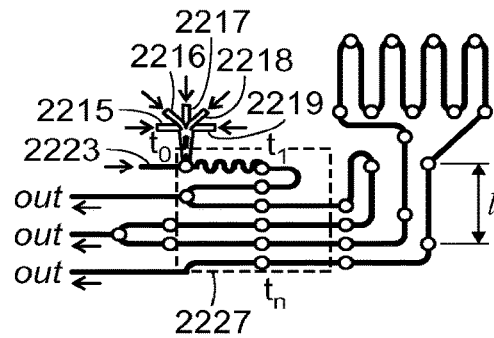
FIG. 22D
| Size of channel (height x width) | ΔP [atm] | U [m/s] | length [μm] | time |
|---|---|---|---|---|
| 15 μm x 50 μm | 0.003 | 0.001 | 10000 | |
| 2 μm x 5 μm | 0.4 | 0.08 | 200 | |
| 2 μm x 1 μm | 0.45 | 0.4 | 10 | 25 μs ↳ mix |
| 2 μm x 3 μm | 2.0 | 0.13 | 400 | 3000 μs = 3.0 ms ↳ observe |
| 15 μm x 50 μm | 0.003 | 0.001 | 10000 | |
FIG. 23

FIG. 48A
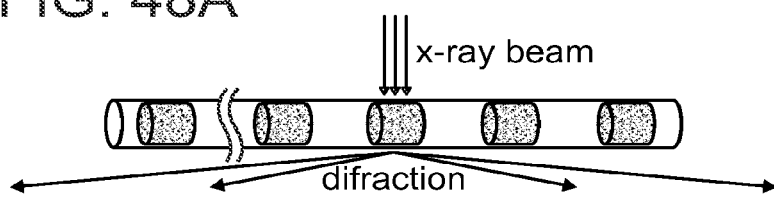
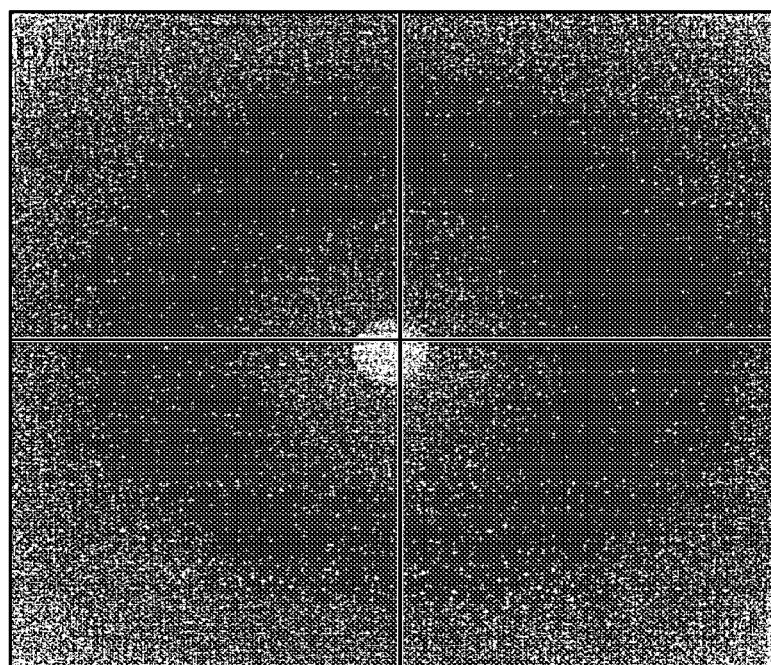
FIG. 48B

METHOD FOR CONDUCTING AN AUTOCATALYTIC REACTION IN PLUGS IN A MICROFLUIDIC SYSTEM

This application is a continuation of U.S. patent application Ser. No. 15/087,176, filed Mar. 31, 2016, which is a continuation of U.S. patent application Ser. No. 13/024,165, filed Feb. 9, 2011, now U.S. Pat. No. 9,329,107, which is a continuation of U.S. patent application Ser. No. 12/777,099, filed May 5, 2010, which is a continuation of U.S. patent application Ser. No. 10/765,718, filed Jan. 26, 2004, now U.S. Pat. No. 7,901,939, which is a continuation-in-part of U.S. patent application Ser. No. 10/434,970, filed May 9, 2003, now U.S. Pat. No. 7,129,091, which claims the benefit of, and priority to, U.S. Provisional Application No. 60/394,544, filed Jul. 8, 2002, and U.S. Provisional Application No. 60/379,927, filed May 9, 2002, all of which are incorporated herein by reference in their entireties.

BACKGROUND

Nonlinear dynamics, in conjunction with microfluidics, play a central role in the design of the devices and the methods according to the invention. Microfluidics deals with the transport of fluids through networks of channels, typically having micrometer dimensions. Microfluidic systems (sometimes called labs-on-a-chip) find applications in microscale chemical and biological analysis (micro-total-analysis systems). The main advantages of microfluidic systems are high speed and low consumption of reagents. They are thus very promising for medical diagnostics and high-throughput screening. Highly parallel arrays of microfluidic systems are used for the synthesis of macroscopic quantities of chemical and biological compounds, e.g., the destruction of chemical warfare agents and pharmaceuticals synthesis. Their advantage is improved control over mass and heat transport.

Microfluidic systems generally require means of pumping fluids through the channels. In the two most common methods, the fluids are either driven by pressure or driven by electroosmotic flow (EOF). Flows driven by EOF are attractive because they can be easily controlled even in complicated networks. EOF-driven flows have flat, plug-like velocity profile, that is, the velocity of the fluid is the same near the walls and in the middle of the channel. Thus, if small volumes of multiple analytes are injected sequentially into a channel, these plugs are transported as non-overlapping plugs (low dispersion), in which case the dispersion comes mostly from the diffusion between plugs. A main disadvantage of EOF is that it is generated by the motion of the double layer at the charged surfaces of the channel walls. EOF can therefore be highly sensitive to surface contamination by charged impurities. This may not be an issue when using channels with negative surface charges in DNA analysis and manipulation because DNA is uniformly negatively charged and does not adsorb to the walls. However, this can be a serious limitation in applications that involve proteins that are often charged and tend to adsorb on charged surfaces. In addition, high voltages are often undesirable, or sources of high voltages such as portable analyzers may not be available.

Flows driven by pressure are typically significantly less sensitive to surface chemistry than EOF. The main disadvantage of pressure-driven flows is that they normally have a parabolic flow profile instead of the flat profile of EOF. Solutes in the middle of the channel move much faster (about twice the average velocity of the flow) than solutes near the walls of the channels. A parabolic velocity profile normally leads to high dispersion in pressure-driven flows; a plug of solute injected into a channel is immediately distorted and stretched along the channel. This distortion is somewhat reduced by solute transport via diffusion from the middle of the channel towards the walls and back. But the distortion is made worse by diffusion along the channel (the overall dispersion is known as Taylor dispersion).

Taylor dispersion broadens and dilutes sample plugs. Some of the sample is frequently left behind the plug as a tail. Overlap of these tails usually leads to cross-contamination of samples in different plugs. Thus, samples are often introduced into the channels individually, separated by buffer washes. On the other hand, interleaving samples with long buffer plugs, or washing the system with buffer between samples, reduces the throughput of the system.

In EOF, flow transport is essentially linear, that is, if two reactants are introduced into a plug and transported by EOF, their residence time (and reaction time) can be calculated simply by dividing the distance traveled in the channel by the velocity. This linear transport allows precise control of residence times through a proper adjustment of the channel lengths and flow rates. In contrast, dispersion in pressure-driven flow typically creates a broad range of residence times for a plug traveling in such flows, and this diminishes time control.

The issue of time control is important. Many chemical and biochemical processes occur on particular time scales, and measurement of reaction times can be indicative of concentrations of reagents or their reactivity. Stopped-flow type instruments are typically used to perform these measurements. These instruments rely on turbulent flow to mix the reagents and transport them with minimal dispersion. Turbulent flow normally occurs in tubes with large diameter and at high flow rates. Thus stopped-flow instruments tend to use large volumes of reagents (on the order of ml/s). A microfluidic analog of stopped-flow, which consumes smaller volumes of reagents (typically µL/min), could be useful as a scientific instrument, e.g., as a diagnostic instrument. So far, microfluidic devices have not be able to compete with stopped-flow type instruments because EOF is usually very slow (although with less dispersion) while pressure-driven flows suffer from dispersion.

In addition, mixing in microfluidic systems is often slow regardless of the method used to drive the fluid because flow is laminar in these systems (as opposed to turbulent in larger systems). Mixing in laminar flows relies on diffusion and is especially slow for larger molecules such as DNA and proteins.

In addition, particulates present handling difficulty in microfluidic systems. While suspensions of cells in aqueous buffers can be relatively easy to handle because cells are isodense with these buffers, particulates that are not isodense with the fluid tend to settle at the bottom of the channel, thus eventually blocking the channel. Therefore, samples for analysis often require filtration to remove particulates.

SUMMARY ACCORDING TO THE INVENTION

In one aspect, a microfluidic system includes a substrate with one or more inlet ports, one or more outlet ports, and an array of traps in fluidic communication with the inlet and outlet ports, and with one or more means for applying force to introduce a fluid via the one or more inlet ports so that a plurality of fluid portions are trapped in the array of traps. Each fluid portion includes reagents sufficient for an autocatalytic reaction including a first species of molecule in a concentration such that each fluid portion contains no more than a single molecule of the first species, and wherein the fluid portions are trapped at least for a period of time sufficient for the autocatalytic reaction to occur such that the single molecule is amplified.

In another aspect the fluid portions are moved to the one or more outlet ports after the period of time has passed. The one or more of the outlet ports may also be an inlet port.

In another aspect, the single molecule is a single biological molecule. The single biological molecule may be DNA or RNA and the autocatalytic reaction may be a polymerase-chain reaction.

In yet another aspect, the system further includes a detector to detect, monitor, or analyze one or more properties of the autocatalytic reaction during and/or after it has occurred. The properties may include light emission. The reagents may include one or more fluorescent labels and the detector may detect emissions from the one or more fluorescent labels.

In a further aspect, the fluid portions are trapped for a period of time that may range from tens of microseconds to hours to weeks.

In another aspect, the array of traps includes an array of connected microchannels. The system may further include one or more valves that are used to control the flow of fluid portions into and/or out of the traps.

In another aspect, each fluid portion is a fluid plug. Each fluid plug may be substantially spherical in shape. In addition, each fluid plug may be substantially surrounded by and immiscible in a carrier fluid.

In yet another aspect, the means for applying force may be a means for applying pressure.

BRIEF DESCRIPTION OF THE DRAWINGS AND PHOTOGRAPHS

FIG. 1A is a schematic diagram of a basic channel design that may be used to induce rapid mixing in plugs. FIGS. 1B-1, 1B-2, 1B-3, and 1B-4 are schematic diagrams depicting a series of periodic variations of the basic channel design. FIGS. 1C-1, 1C-2, 1C-3, and 1C-4 are schematic diagrams depicting a series of aperiodic combinations resulting from a sequence of alternating elements taken from a basic design element shown in FIG. 1A and an element from the periodic variation series shown in FIGS. 1B-1, 1B-2, 1B-3, and 1B-4.

FIGS. 2A-1 and 2A-2 are schematic diagrams contrasting laminar flow transport and plug transport in a channel, respectively. FIG. 2B-1 shows a photograph (right side, top portion) illustrating rapid mixing inside plugs moving through winding channels. FIG. 2B-2 shows a photograph (right side, lower portion) showing that winding channels do not accelerate mixing in a laminar flow in the absence of PFD.

Figure 6:
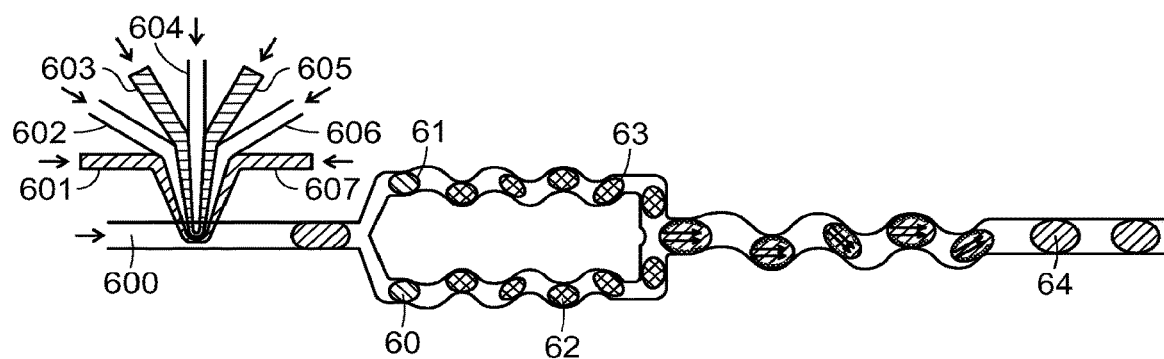

FIG. 6 is a schematic representation of part of a microfluidic network that uses multiple inlets and that allows for both splitting and merging of plugs. This schematic diagram shows two reactions that are conducted simultaneously. A third reaction (between the first two reaction mixtures) is conducted using precise time delay.

Figure 7A:
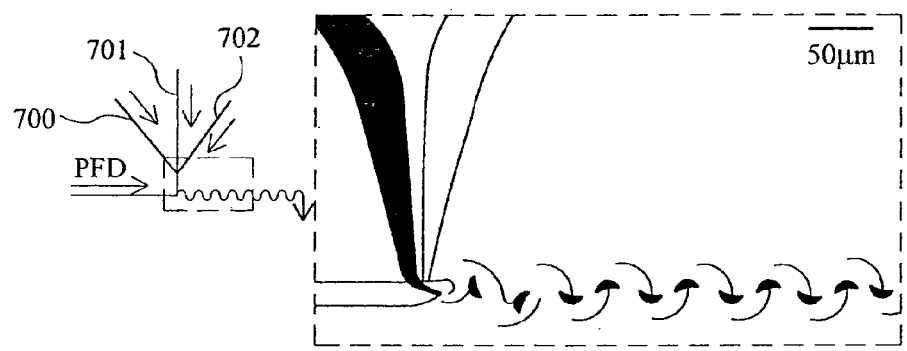
Figure 7B:
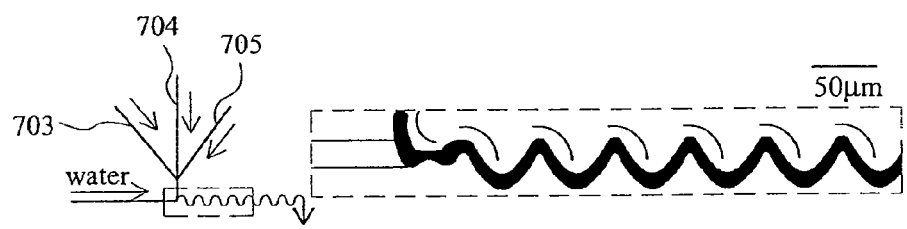
Figure 7C:
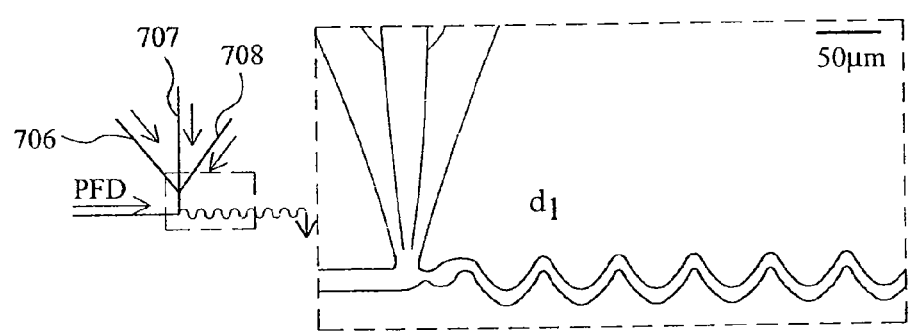
Figure 7E:
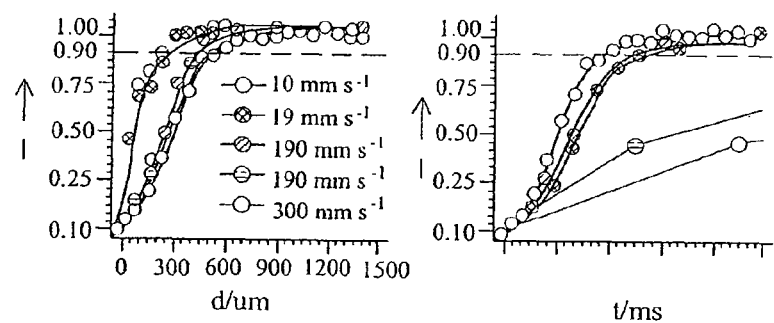
Figure 7E:
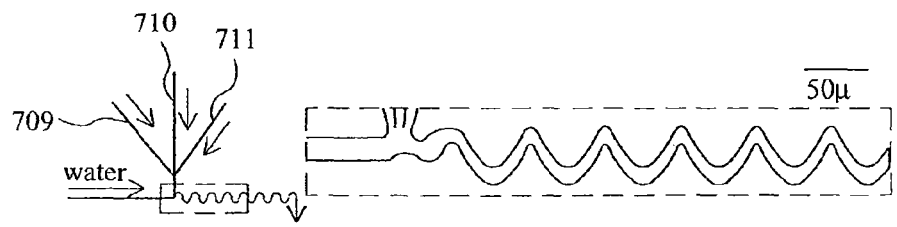
Figure 8A:
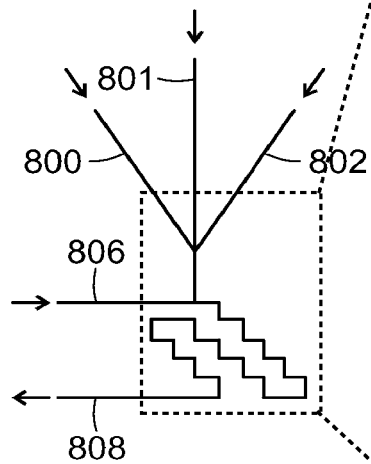
Figure 8B:
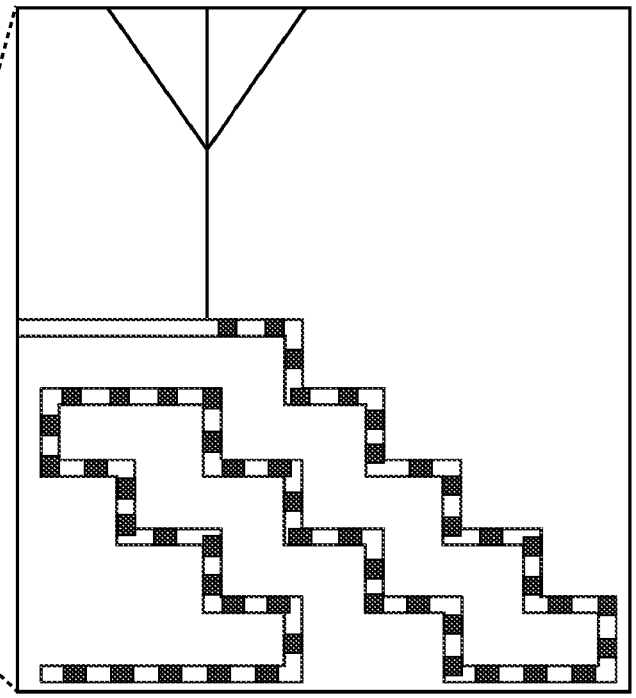
Figure 8C:
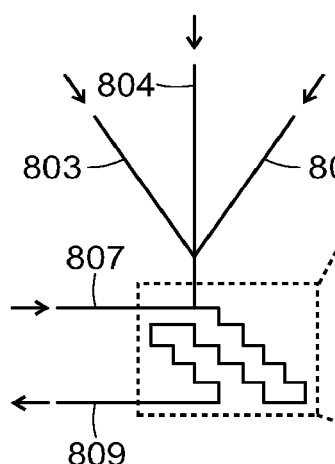
Figure 8D:
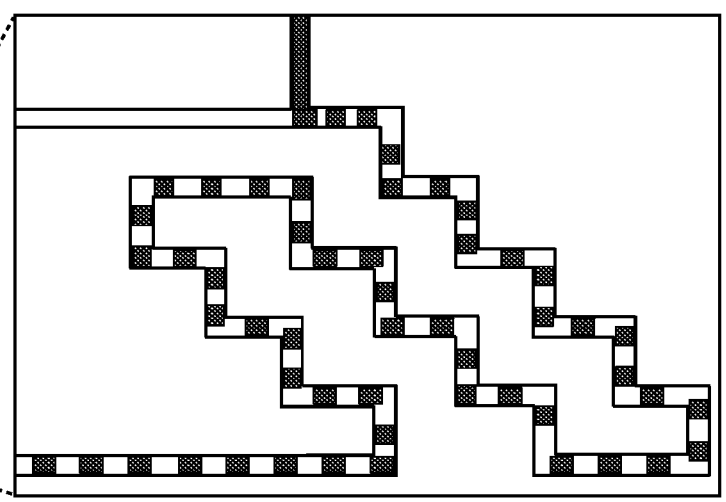
Figure 9A:
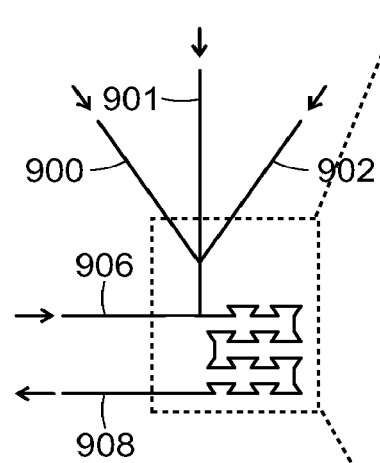
Figure 9B:
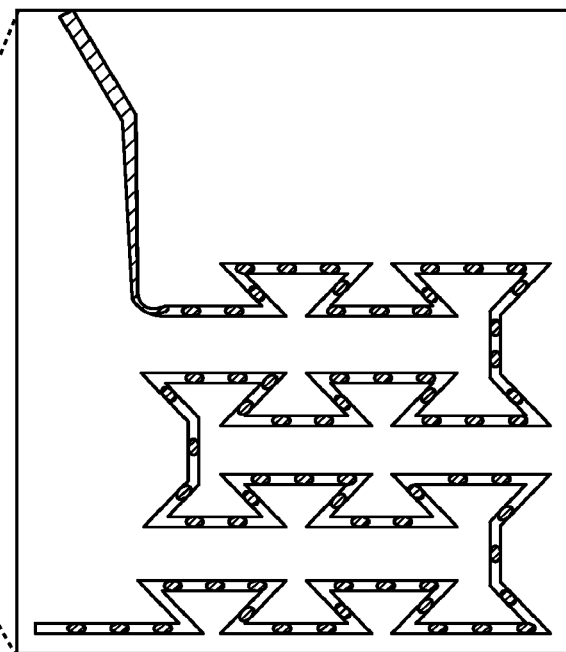
Figure 9C:
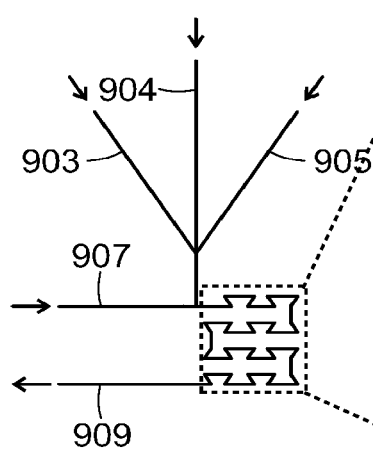
Figure 9D:
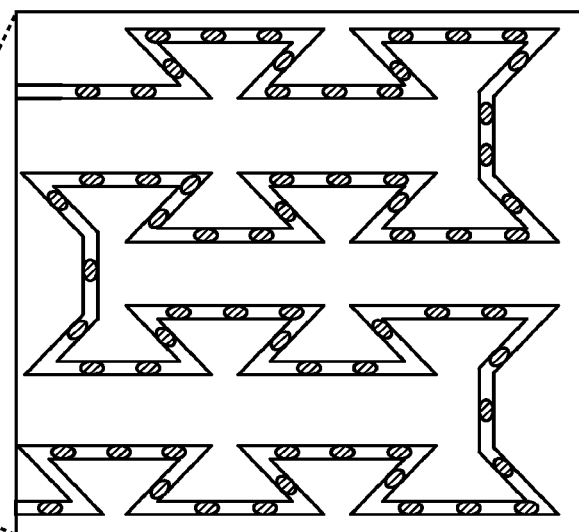

FIGS. 7A-7B show microphotographs (10 µs exposure) illustrating rapid mixing inside plugs (a) and negligible mixing in a laminar flow (b) moving through winding channels at the same total flow velocity. FIG. 7C shows a false-color microphotograph (2 s exposure, individual plugs are invisible) showing time-averaged fluorescence arising from rapid mixing inside plugs of solutions of Fluo-4 and $CaCl_2$. FIGS. 7D(i) and 7D(ii) show plots of the relative normalized intensity (I) of fluorescence obtained from images such as shown in FIG. 7C as a function of distance (FIG. 7D(i)) traveled by the plugs and of time required to travel that distance FIG. 7D(ii) at a given flow rate. FIG. 7E shows a false-color microphotograph (2 s exposure) of the weak fluorescence arising from negligible mixing in a laminar flow of the solutions used in FIG. 7C.

FIGS. 8A, 8B, 8C, and 8D show photographs (FIGS. 8B and 8D) and schematics (FIGS. 8A and 8C) that illustrate fast mixing at flow rates of about 0.5 µL/min and about 1.0 µL/min using 90°-step channels.

FIGS. 9A, 9B, 9C, and 9D show schematics (FIGS. 9A and 9C) and photographs (FIGS. 9B and 9D) illustrates fast mixing at flow rates of about 1.0 µL/min and about 0.5 µL/min using 135°-step channels.

Figure 10A:
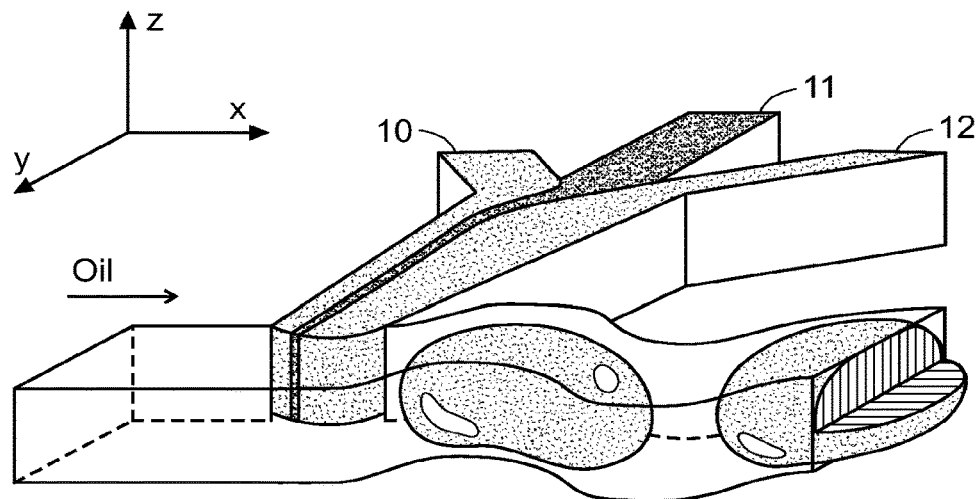
Figure 10B:
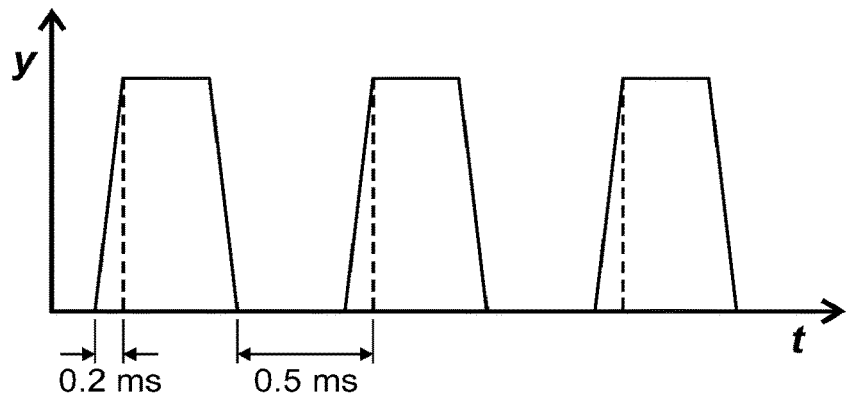

FIG. 10A is a schematic diagram depicting three-dimensional confocal visualization of chaotic flows in plugs. FIG. 10B is a plot showing a sequence preferably used for visualization of a three-dimensional flow.

Figure 11:
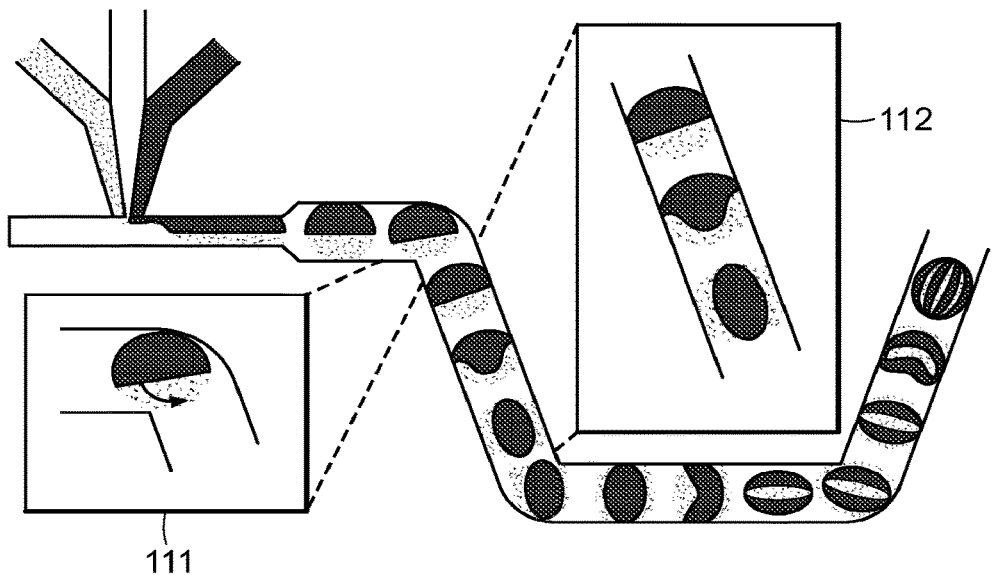

FIG. 11 shows a schematic diagram of a channel geometry designed to implement and visualize the baker's transformation of plugs flowing through microfluidic channels.

Figure 12A:
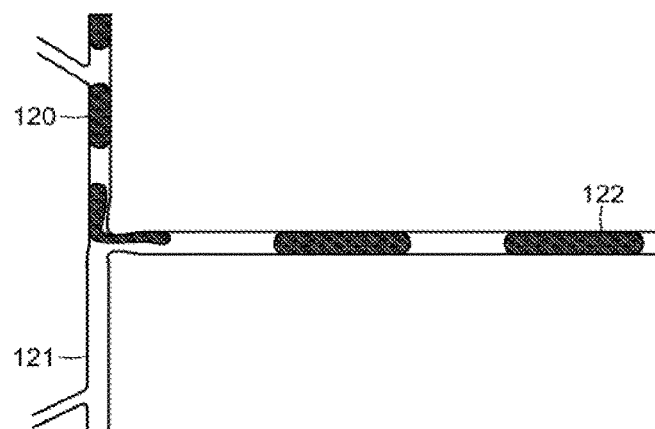
Figure 12B:
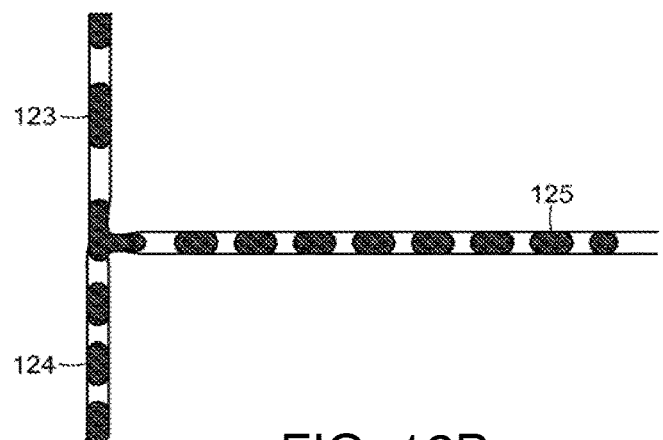

FIGS. 12A and 12B show photographs depicting the merging of plugs (FIG. 12A) and splitting of plugs (FIG. 12B) that flow in separate channels or channel branches that are perpendicular.

Figure 13:
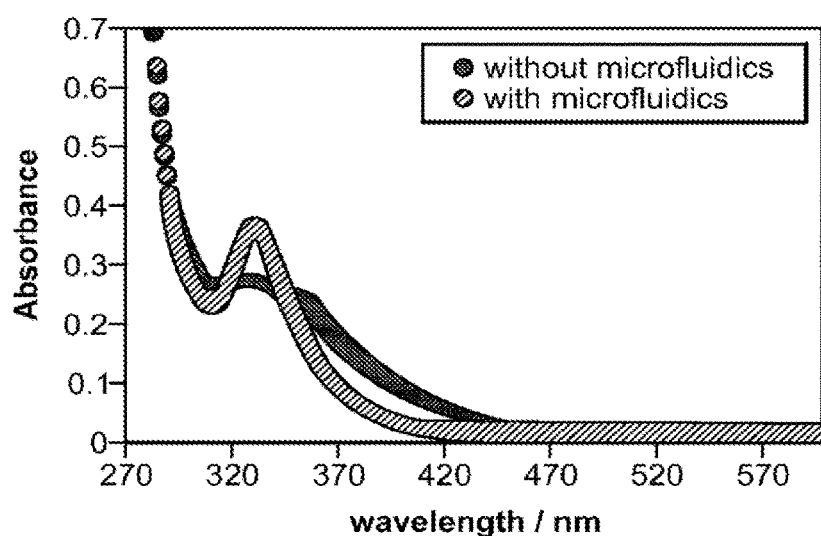

FIG. 13 shows UV-VIS spectra of CdS nanoparticles formed by rapid mixing in plugs (spectrum with a sharp absorption peak) and by conventional mixing of solutions.

Figure 14A:
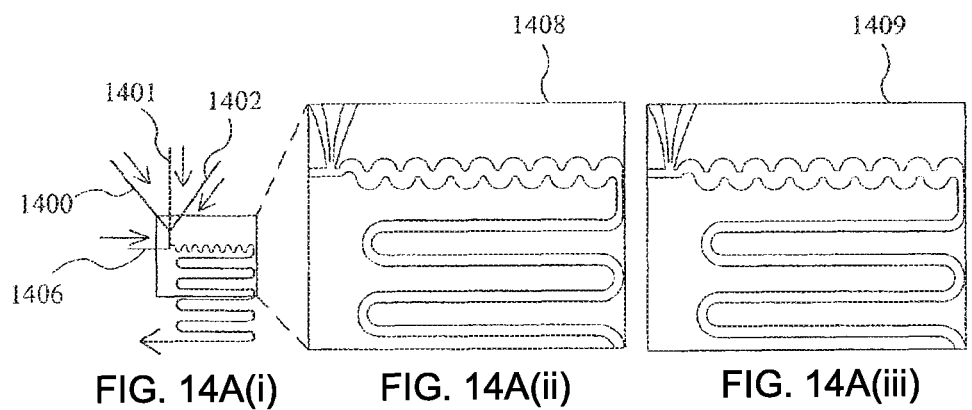
Figure 14B:
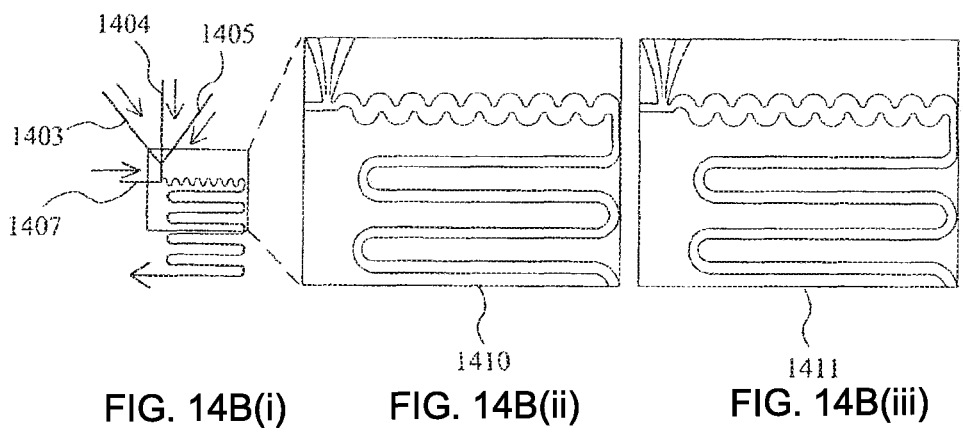

FIGS. 14A and 14B illustrate the synthesis of CdS nanoparticles in PDMS microfluidic channels in single-phase aqueous laminar flow (FIG. 14A) and in aqueous plugs that are surrounded by water-immiscible perfluorodecaline (FIG. 14B). In particular, FIGS. 14A(i), 14A(ii), and 14A(iii) and 14B(i), 14B(ii), and 14B(iii)-show schematic diagrams (FIGS. 14A(i) and 14B(i)) and photographs (FIGS. 14A(ii), 14A(iii), 14B(ii), and 14B(iii)) that illustrate the synthesis of CdS nanoparticles in PDMS microfluidic channels in single-phase aqueous laminar flow (FIGS. 14A(i), 14A(ii), and 14A(iii)) and in aqueous plugs that are surrounded by water-immiscible perfluorodecaline (FIGS. 14B(i), 14B(ii), and 14B(iii)).

Figure 15:
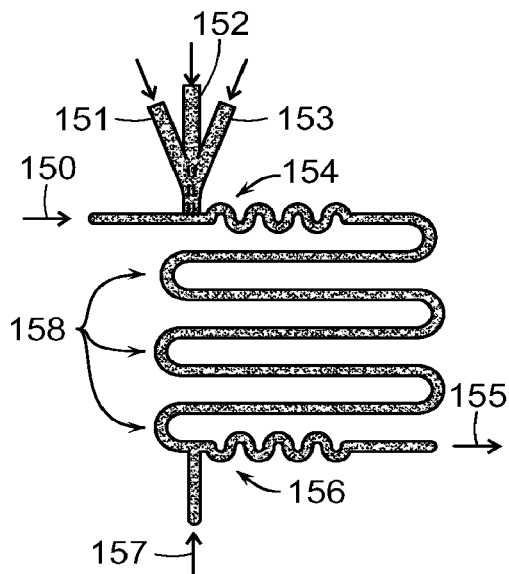

FIG. 15 shows schematic representations of the synthesis of CdS nanoparticles inside plugs.

Figure 16:
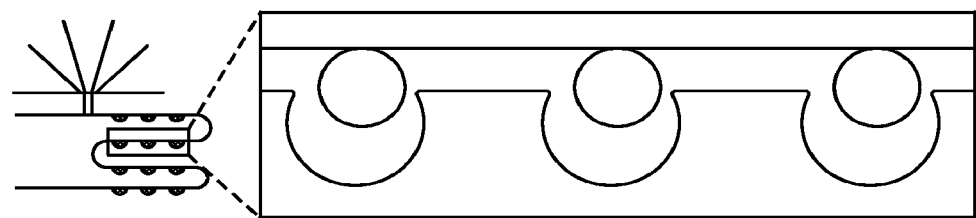

FIG. 16 is a schematic illustration of a microfluidic device according to the invention that illustrates the trapping of plugs.

Figure 17:
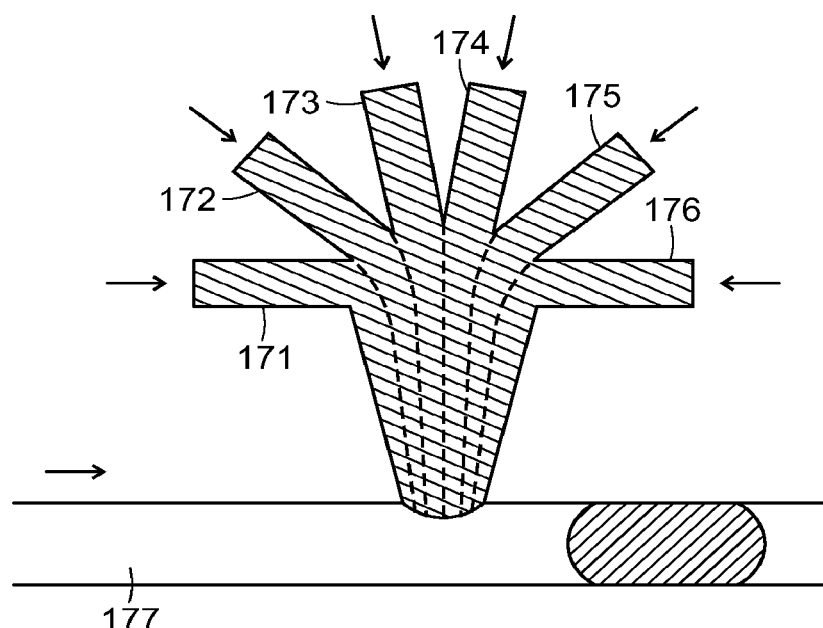

FIG. 17 is a schematic of a microfluidic method for forming plugs with variable compositions for protein crystallization.

Figure 18:
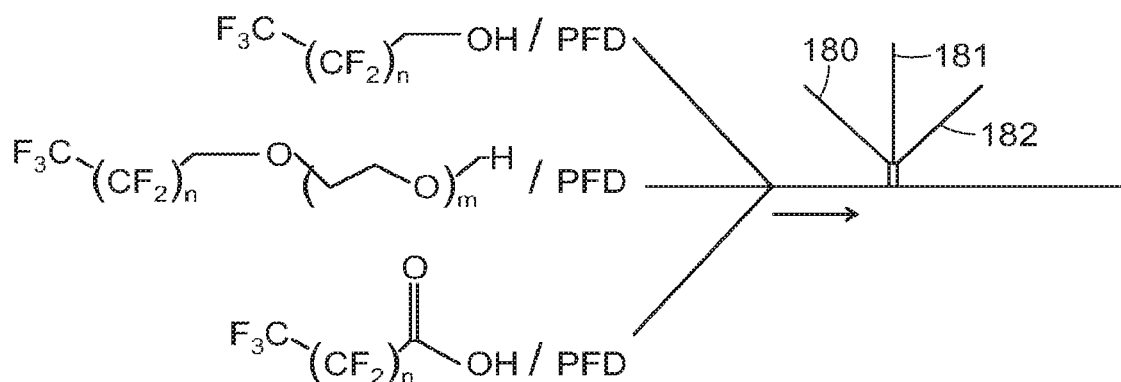

FIG. 18 is a schematic illustration of a method for controlling heterogeneous nucleation by varying the surface chemistry at the interface of an aqueous plug-fluid and a carrier-fluid.

Figure 19:
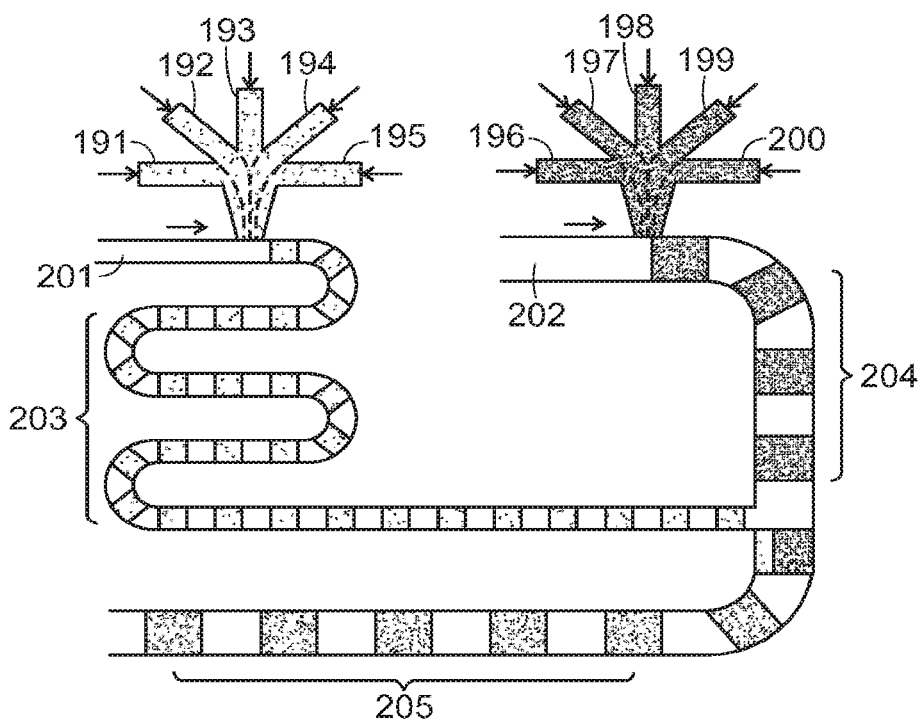

FIG. 19 is a schematic diagram that illustrates a method of separating nucleation and growth using a microfluidic network according to the present invention.

Figures 20A, 20B:
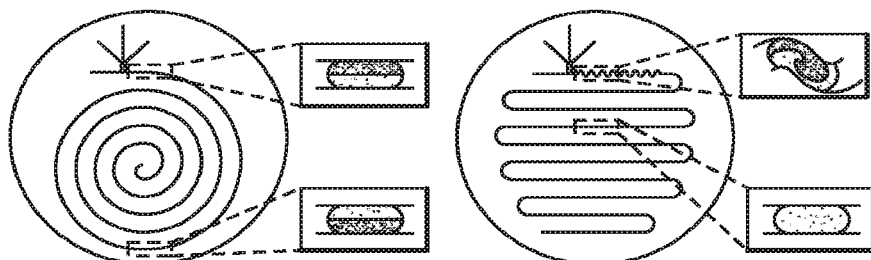

FIGS. 20A and 20B show schematic diagrams that illustrate two methods that provide a precise and reproducible degree of control over mixing and that can be used to determine the effect of mixing on protein crystallization.

Figure 21:
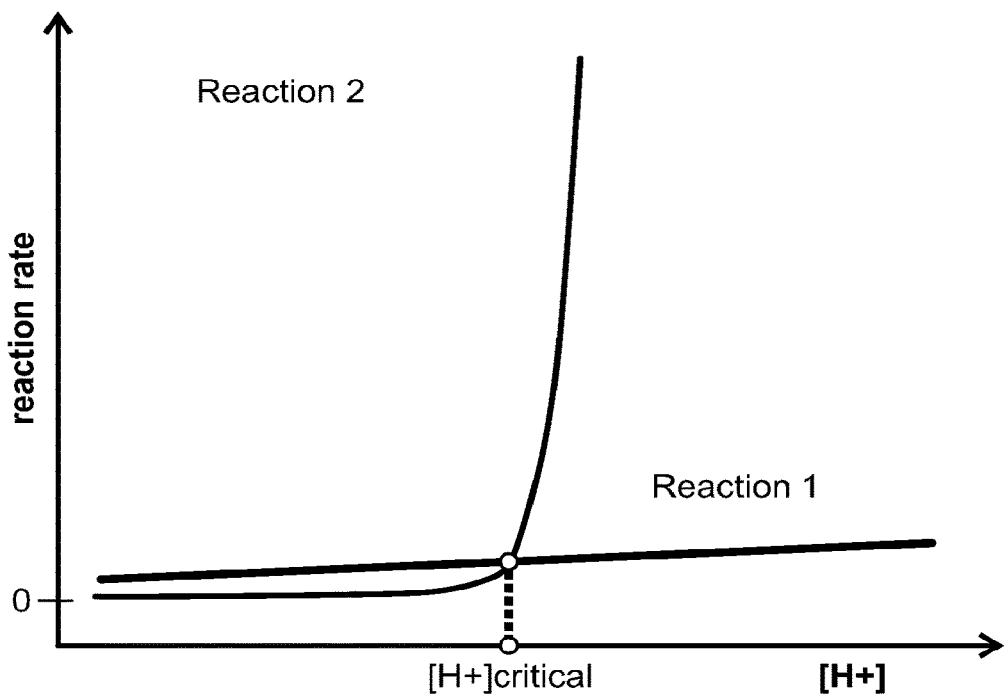
Figure 22A:
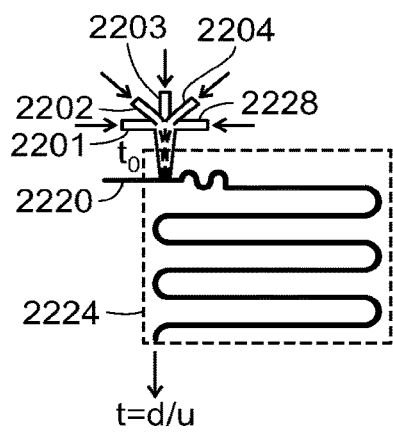
Figure 22B:
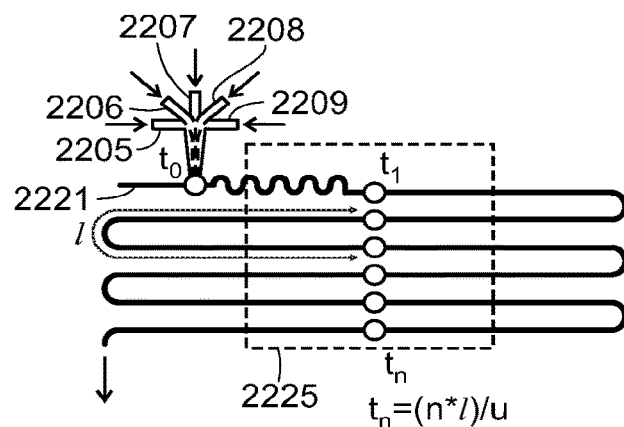

FIG. 21 is a reaction diagram illustrating an unstable point in the chlorite-thiosulfate reaction.

FIGS. 22A, 22B, 22C, and 22D are schematic diagrams that show various examples of geometries of microfluidic channels according to the invention for obtaining kinetic information from single optical images.

FIG. 23 shows a schematic of a microfluidic network (left side) and a table of parameters for a network having channel heights of 15 and 2 µm.

Figure 24A:
Figure 24B:
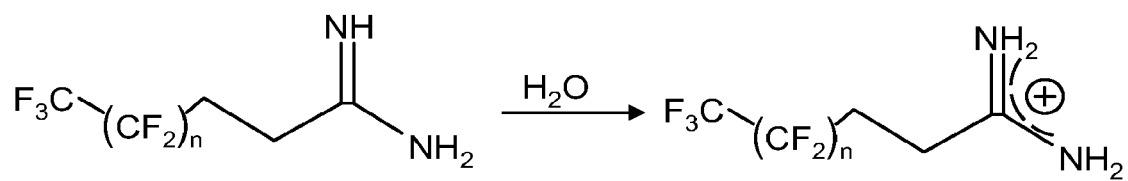
Figure 24C:
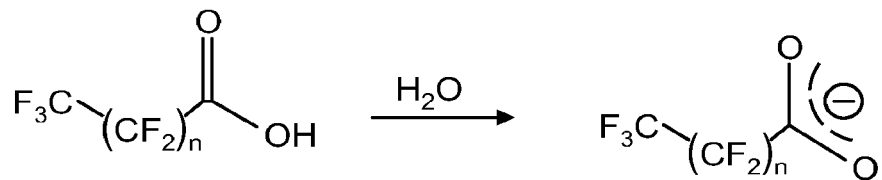

FIG. 24A shows a reaction scheme that depicts examples of fluorinated surfactants that form monolayers that are: (a) resistant to protein adsorption; (b) positively charged; and (c) negatively charged. FIG. 24B shows a chemical structure of neutral surfactants charged by interactions with water by protonation of an amine or a guanidinium group. FIG. 24C shows a chemical structure of neutral surfactants charged by interactions with water deprotonation of a carboxylic acid group.

Figure 25A:
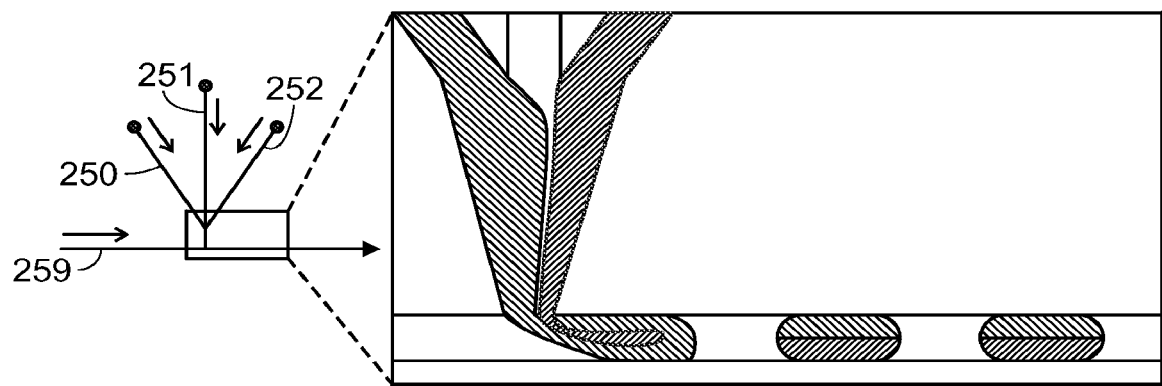
Figure 25B:
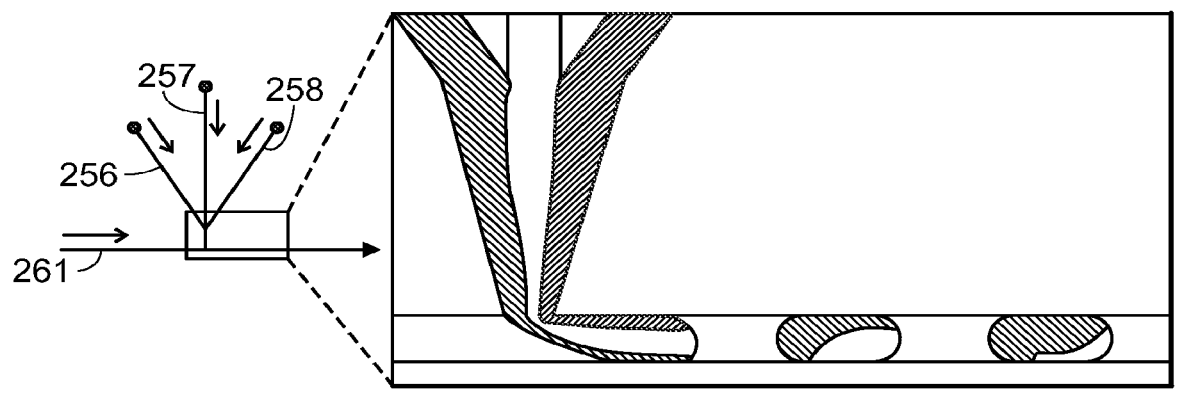
Figure 25C:
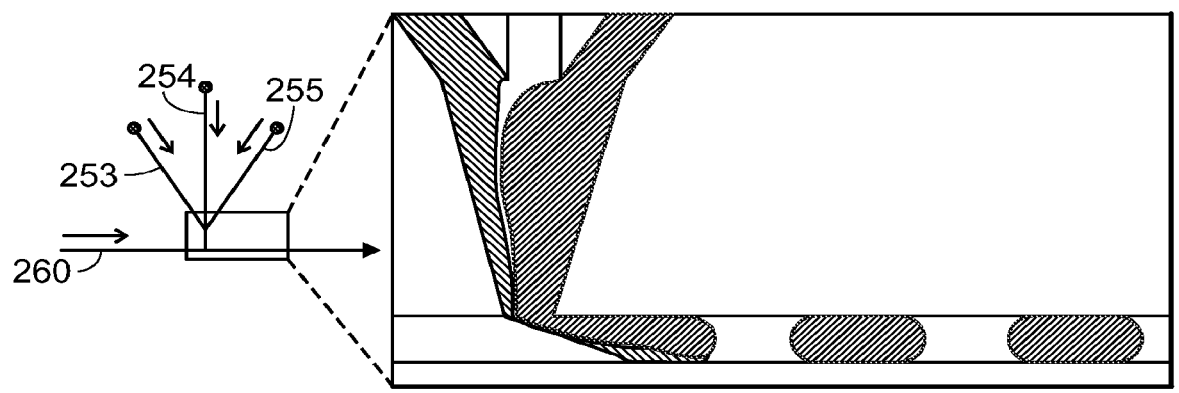

FIGS. 25A, 25B, and 25C are schematic diagrams of microfluidic network (left side of FIGS. 25A, 25B, 25C) that can be used for controlling the concentrations of aqueous solutions inside the plugs, as well as photographs (right side of FIGS. 25A, 25B, 25C) showing the formation of plugs with different concentrations of the aqueous streams.

Figure 26A:
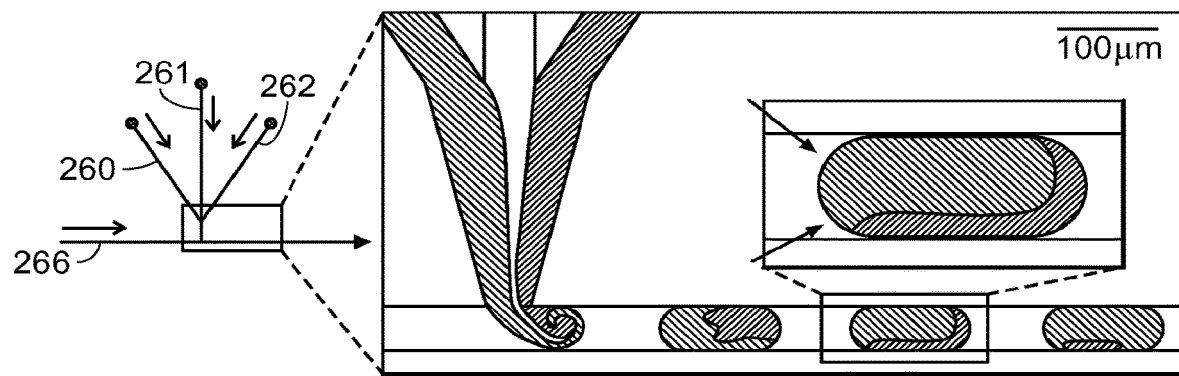
Figure 26B:
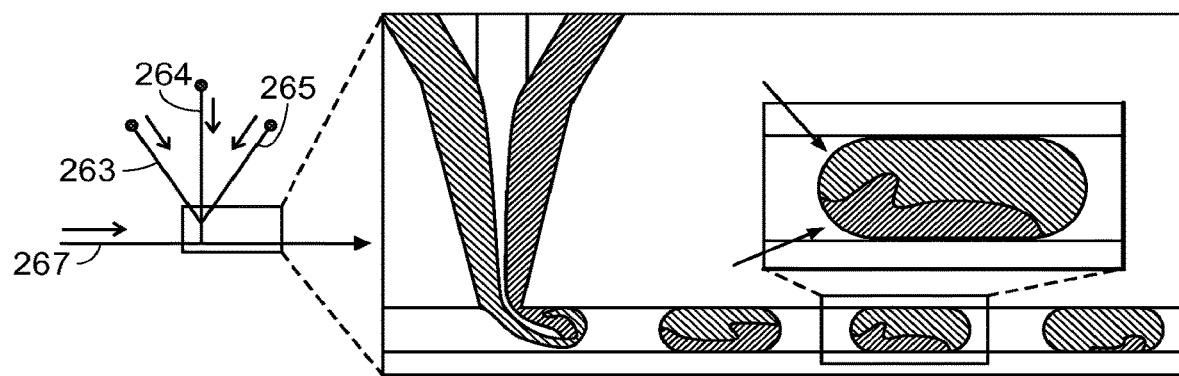

FIGS. 26A and 26B are schematic diagrams of microfluidic network (left side of FIG. 26A and FIG. 26B) and photographs (right side of FIG. 26A and FIG. 26B) of the plug-forming region of the network in which the aqueous streams were dyed with red and green food dyes to show their flow patterns.

Figure 1A:
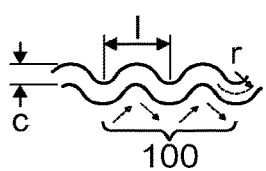
Figures 1, 1B:
Figures 1, 1B, 2:
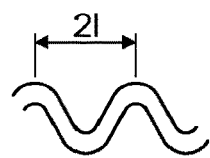
Figures 1, 27A:
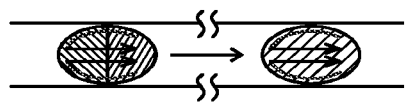
Figures 2, 27A:
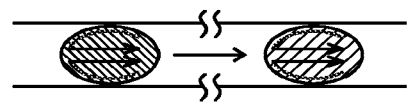
Figure 27B:
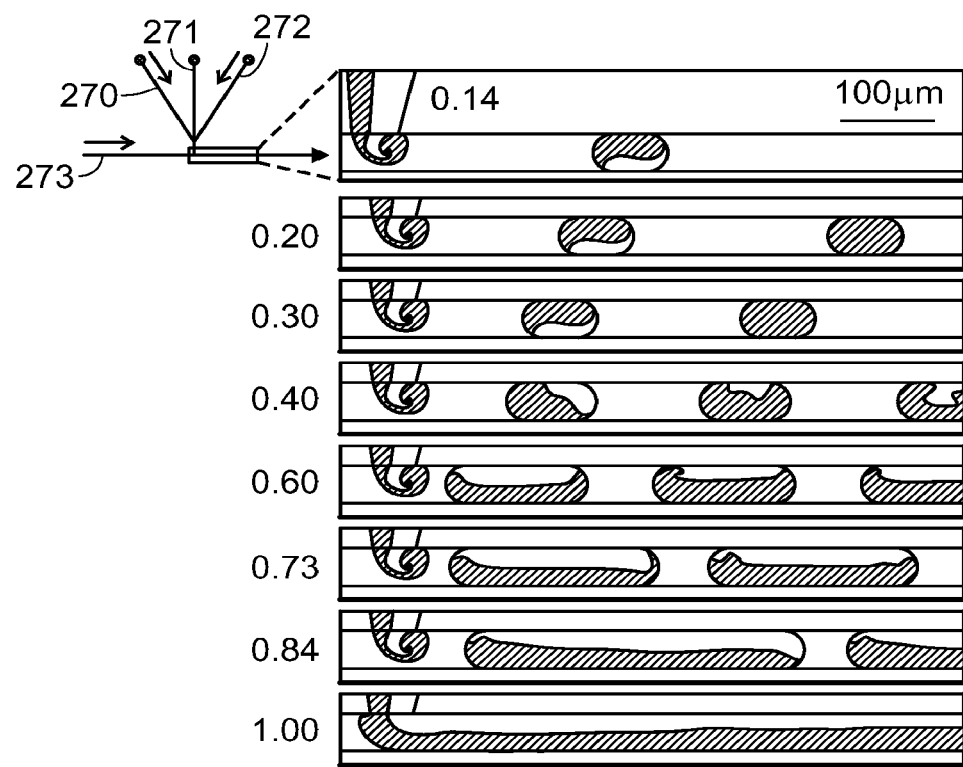
Figures 1, 27C:
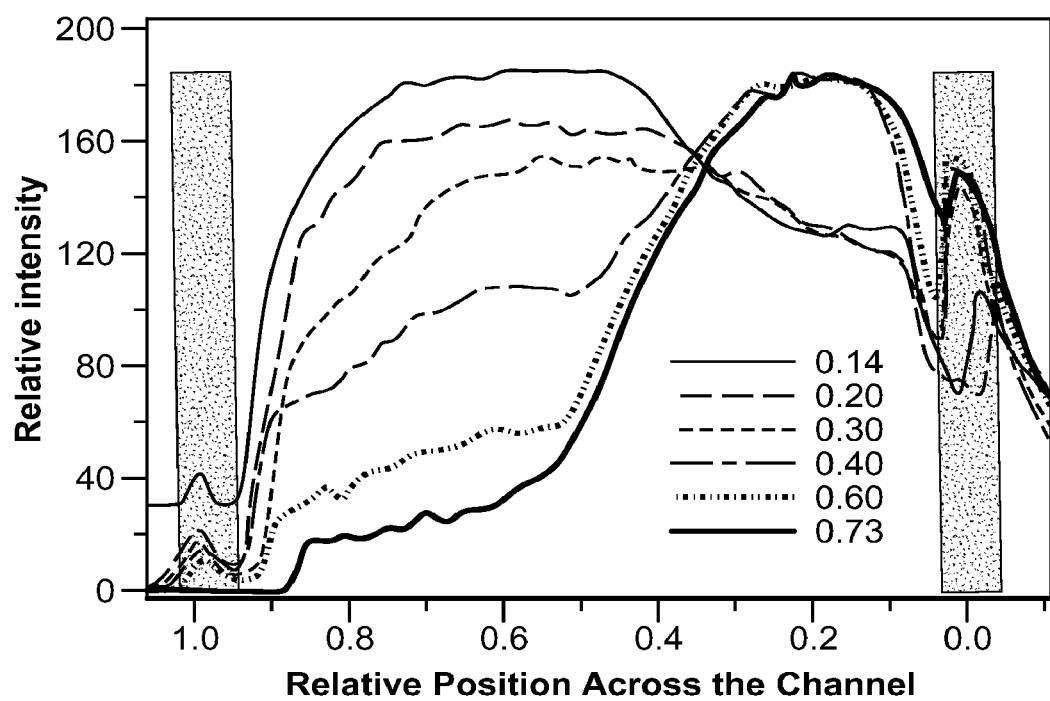
Figures 2, 27C:
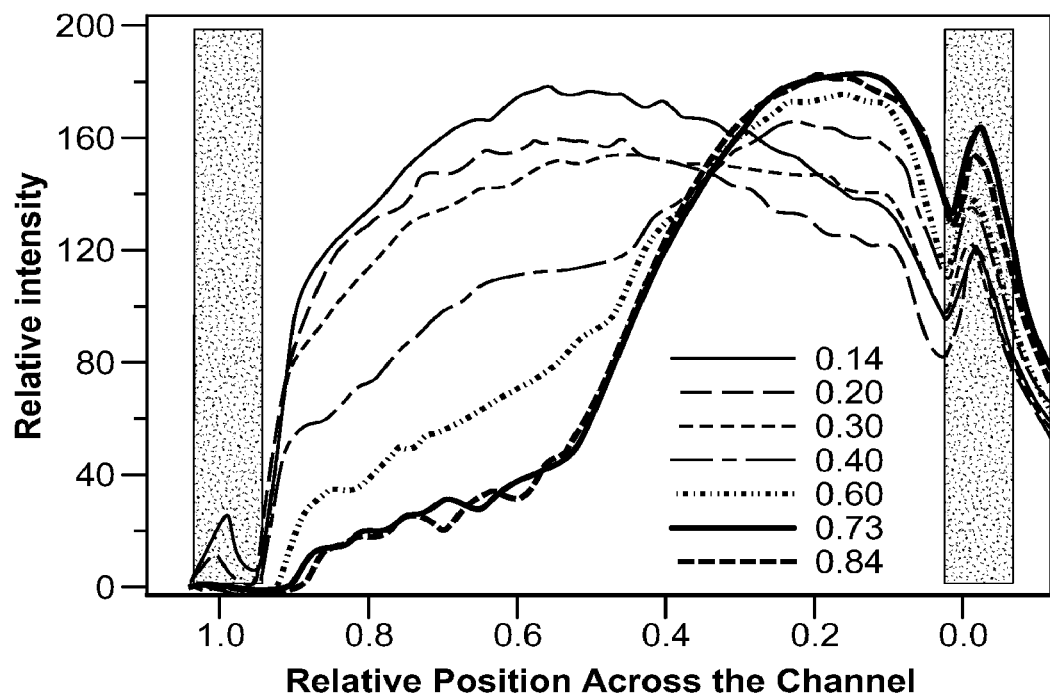

FIGS. 27A-1 to 27A-2, 27B, and 27C-1 to 27C-2 are photographs and plots showing the effects of initial conditions on mixing by recirculating flow inside plugs moving through straight microchannels. FIG. 27A-1 is a schematic diagram showing that recirculating flow (shown by black arrows) efficiently mixed solutions of reagents that were initially localized in the front and back halves of the plug. FIG. 27A-2 is a schematic diagram showing that recirculating flow (shown by black arrows) did not efficiently mix solutions of reagents that were initially localized in the left and right halves of the plugs. FIG. 27B shows a schematic diagram showing the inlet portions (left side) and photographs of images showing measurements of various periods and lengths of plugs. FIG. 27C-1 shows a graph of the relative optical intensity of Fe(SCN)x(3-x)+ complexes in plugs of varying lengths. FIG. 27C-2 is the same as FIG. 27c1) except that each plug traverses a distance of 1.3 mm.

Figure 28:
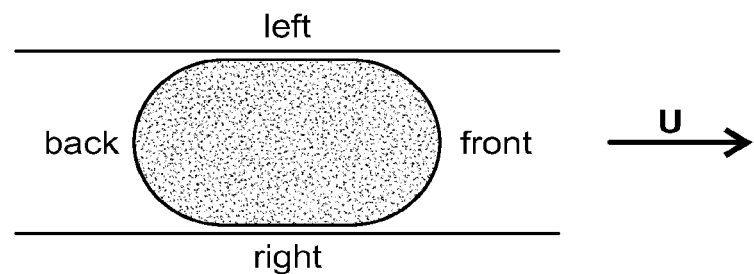

FIG. 28 is a schematic illustration of a plug showing the notation used to identify different regions of the plugs relative to the direction of motion.

Figure 29A:
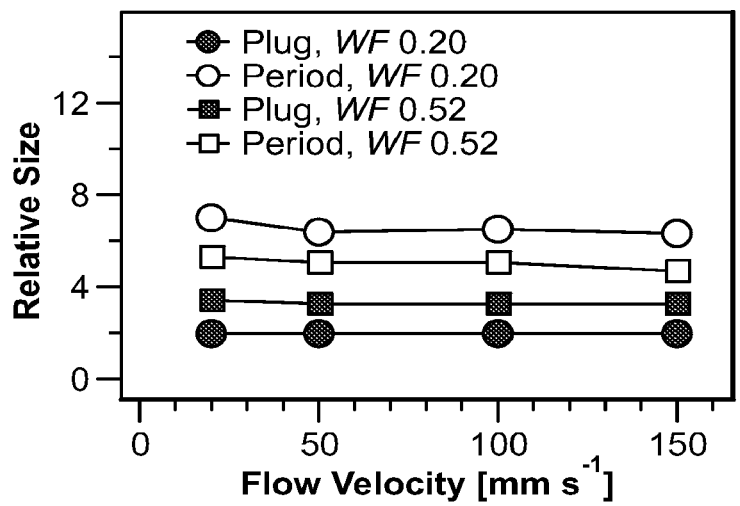
Figure 29B:
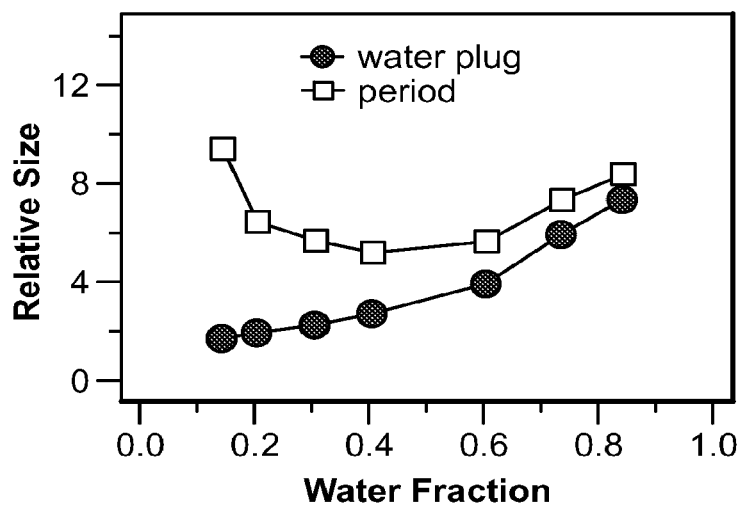

FIGS. 29A and 29B are plots of the periods and the lengths of plugs as a function of total flow velocity (FIG. 29A) and water fraction (FIG. 29B).

Figure 30:
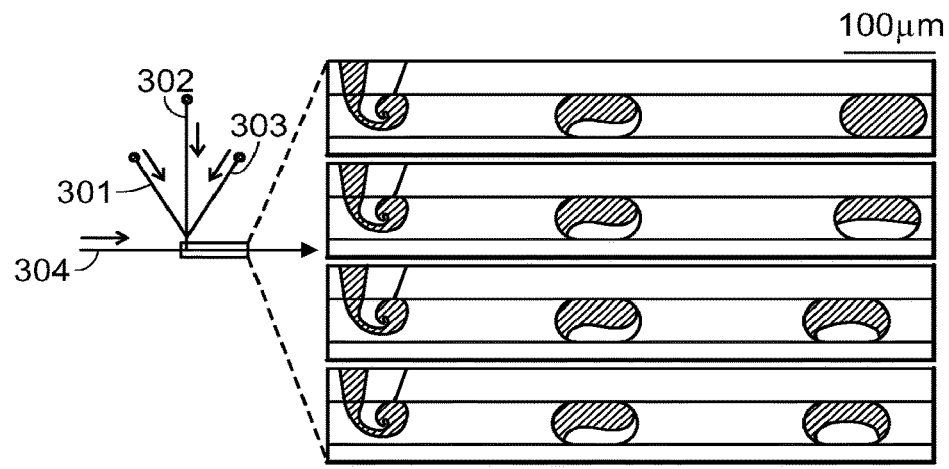

FIG. 30 shows photographs illustrating weak dependence of periods, length of plugs, and flow patterns inside plugs on total flow velocity.

Figure 31A:
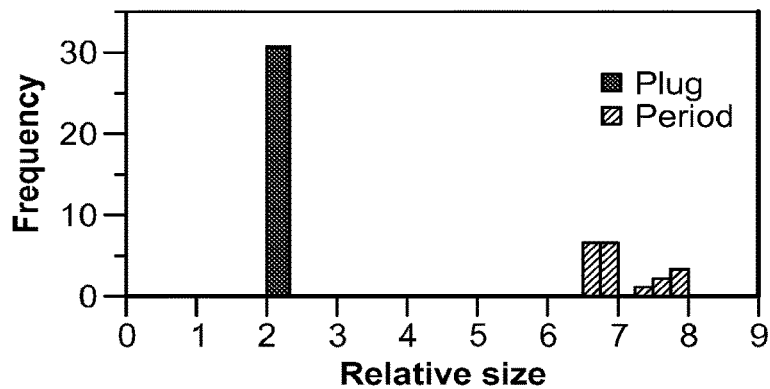
Figure 31B:
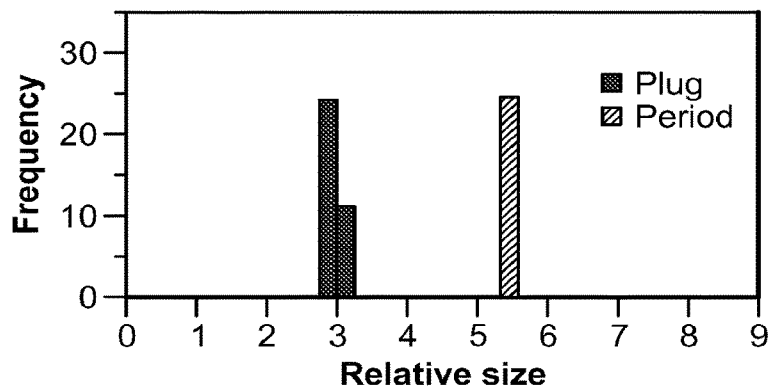
Figure 31C:
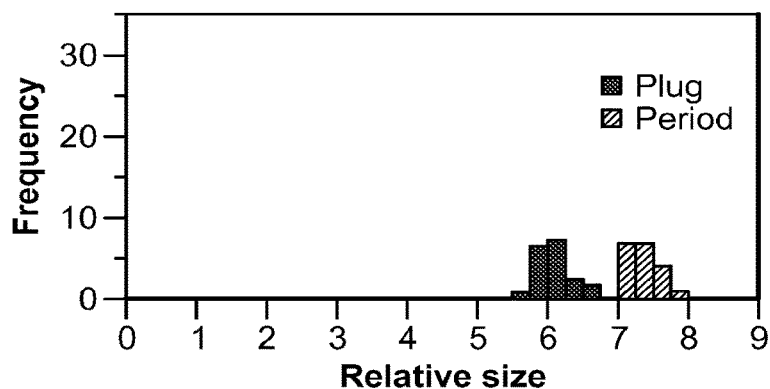

FIGS. 31A, 31B, and 31C are plots showing the distribution of periods and lengths of plugs where the water fractions were 0.20 (FIG. 31A), 0.40 (FIG. 31B), and 0.73 (FIG. 31C), respectively.

Figure 32:
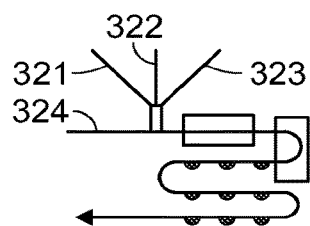
Figure 32:
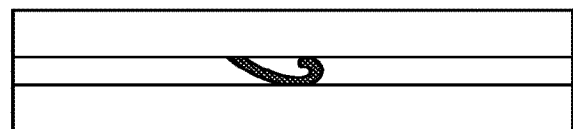
Figure 32:
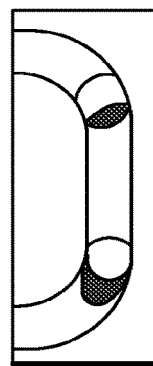

FIG. 32 shows photographs (middle and right side) that show that plug traps are not required for crystal formation in a microfluidic network, as well as a diagram of the microfluidic network (left side).

Figure 33A:
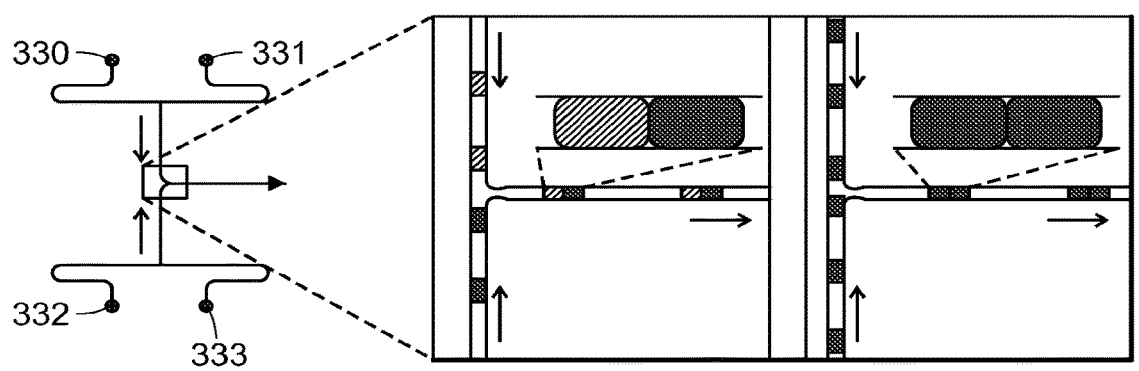
Figure 33B:
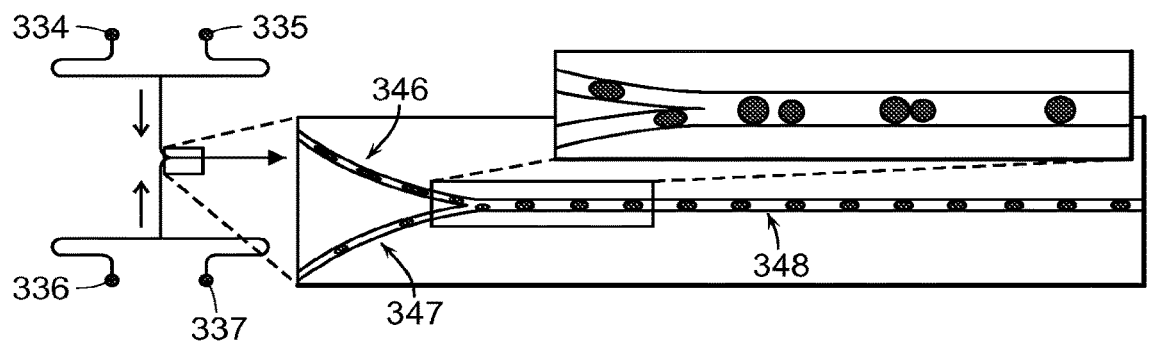
Figure 33C:
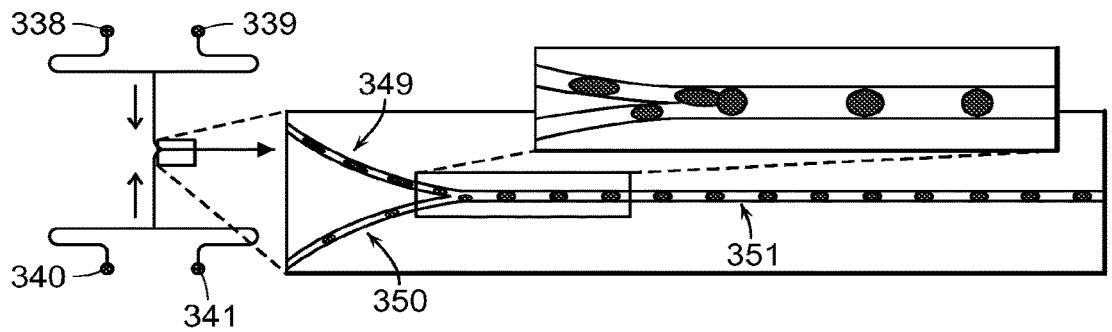
Figure 33D:
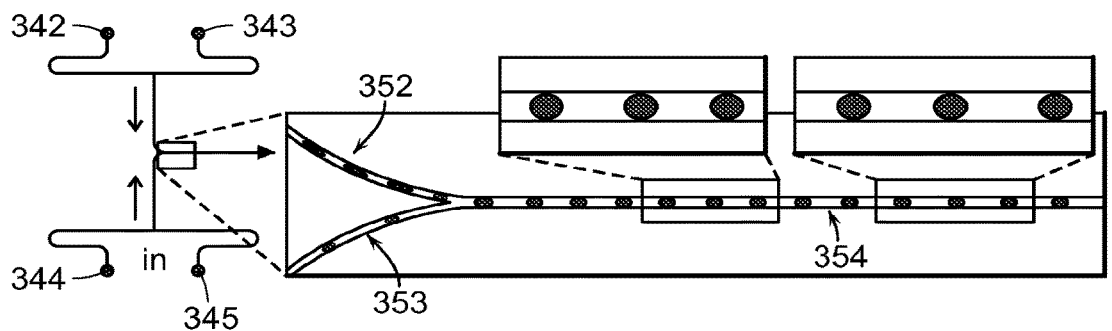

FIGS. 33A, 33B, 33C, and 33D (left side) are top views of microfluidic networks (left side) and photographs (right side) that comprise channels having either uniform or non-uniform dimension. FIG. 33A shows that merging of the plugs occurs infrequently in the T-shaped channel shown in the photographs. FIG. 33B illustrates plug merging occurring between plugs arriving at different times at the Y-shaped junction (magnified view shown). FIG. 33C depicts in-phase merging, i.e., plug merging upon simultaneous arrival of at least two plugs at a junction, of plugs of different sizes generated using different oil/water ratios at the two pairs of inlets. FIG. 33D illustrates defects (i.e., plugs that fail to undergo merging when they would normally merge under typical or ideal conditions) produced by fluctuations in the relative velocity of the two incoming streams of plugs.

Figure 34A:
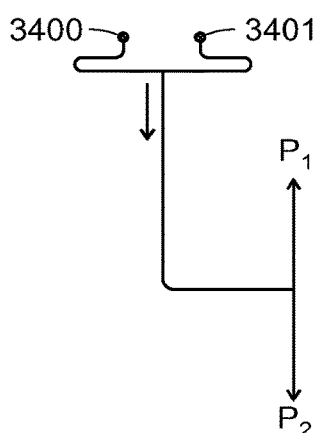
Figure 34B:
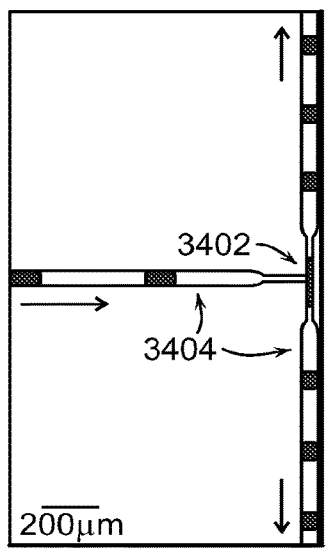
Figure 34C:
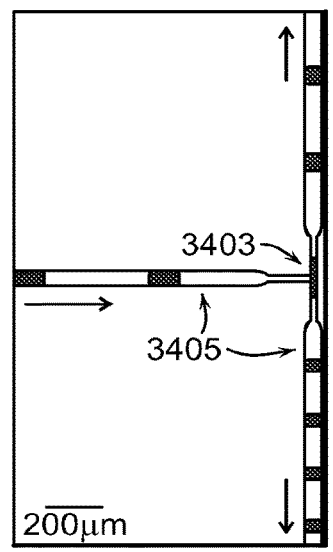

FIGS. 34A, 34B, and 34C show a schematic diagram (a, left side) and photographs (b, c) each of which depicts a channel network viewed from the top. FIG. 34A is a schematic diagram of the channel network used in the experiment. FIG. 34B is a photograph showing the splitting of plugs into plugs of approximately one-half the size of the initial plugs. FIG. 34C is a photograph showing the asymmetric splitting of plugs which occurred when P1<P2.

Figure 35:
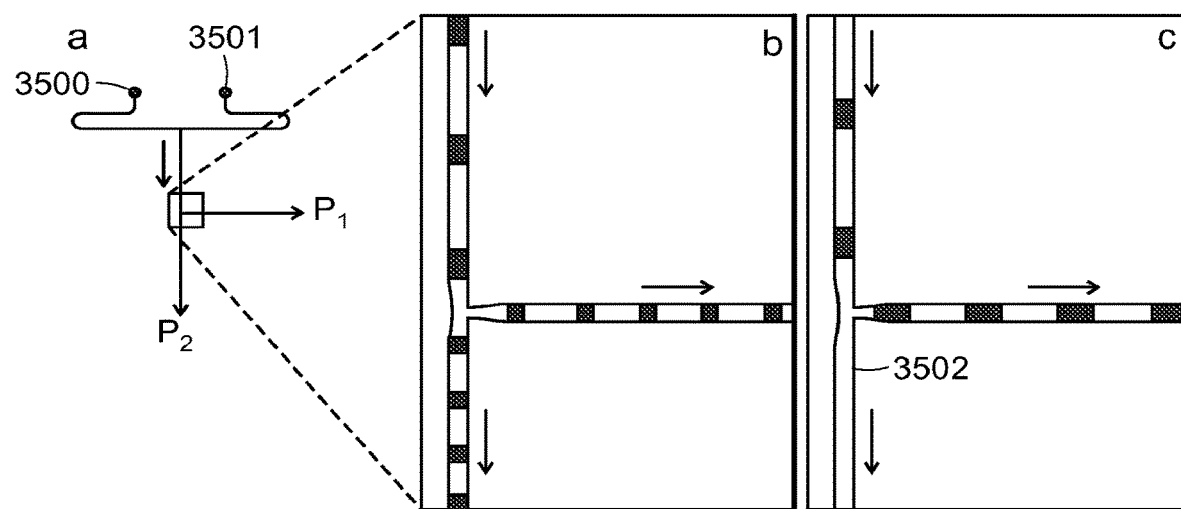

FIG. 35 shows a schematic diagram (a, left side) and photographs (b, c) that depicts the splitting of plugs using microfluidic networks without constrictions near the junction.

Figure 36:
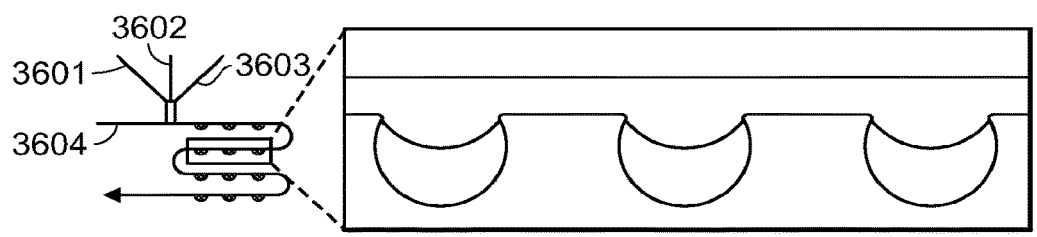

FIG. 36 shows a photograph (right side) of lysozyme crystals grown in water plugs in the wells of the microfluidic channel, as well as a diagram (left side) of the microfluidic network used in the crystallization.

Figure 37:
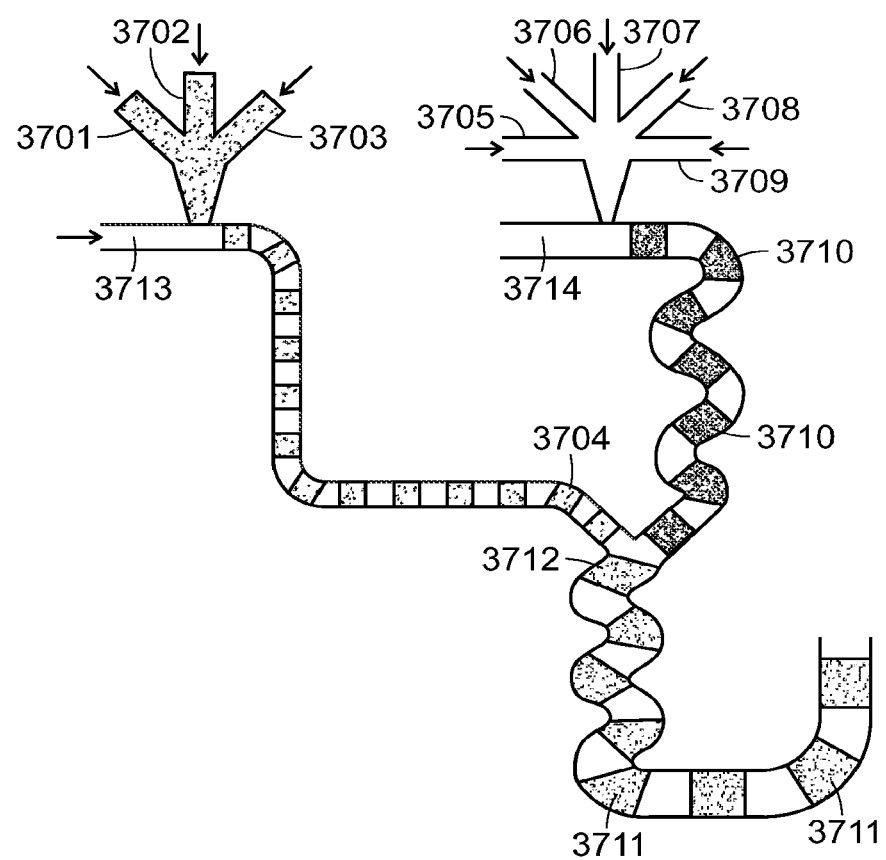

FIG. 37 is a schematic diagram that depicts a microfluidic device according to the invention that can be used to amplify a small chemical signal using an autocatalytic (and possibly unstable) reaction mixture.

Figure 38:
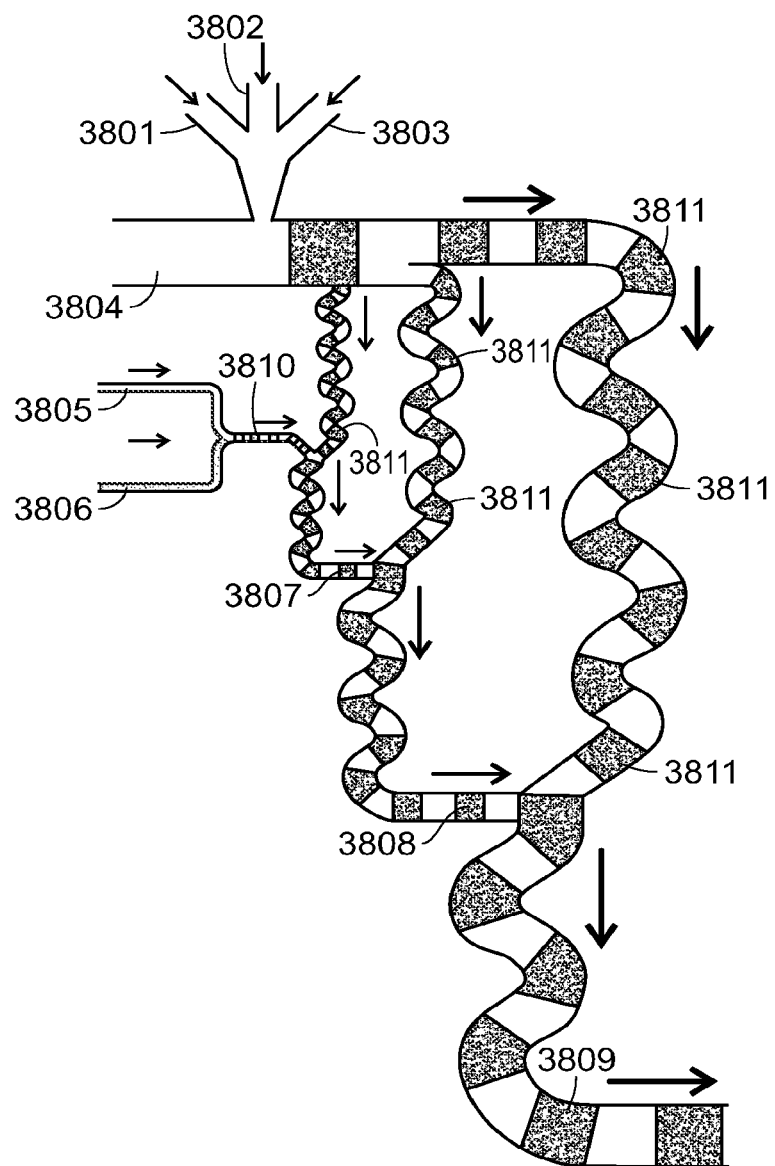

FIG. 38 is a schematic diagram that illustrates a method for a multi-stage chemical amplification which can be used to detect as few as a single molecule.

Figure 39:
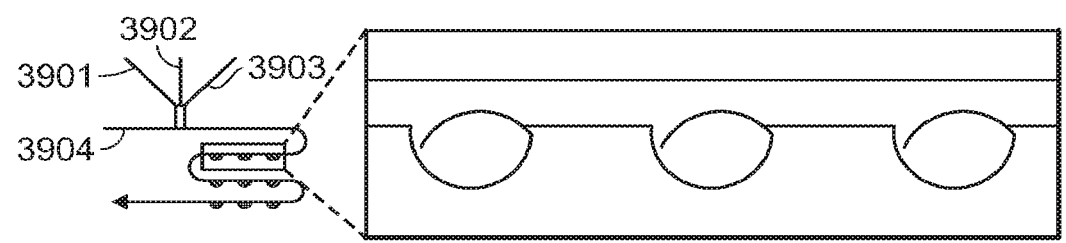

FIG. 39 shows a diagram (left side) of the microfluidic network and a photograph (right side) of water plugs attached to the PDMS wall.

Figure 40A:
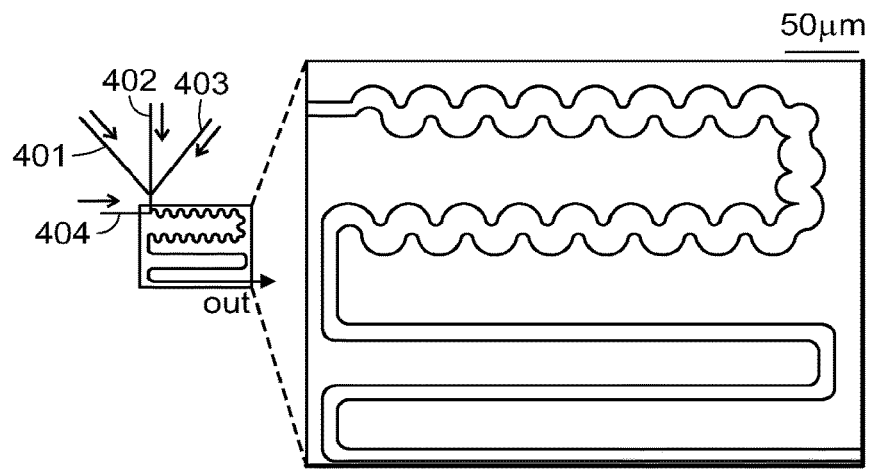
Figure 40B:
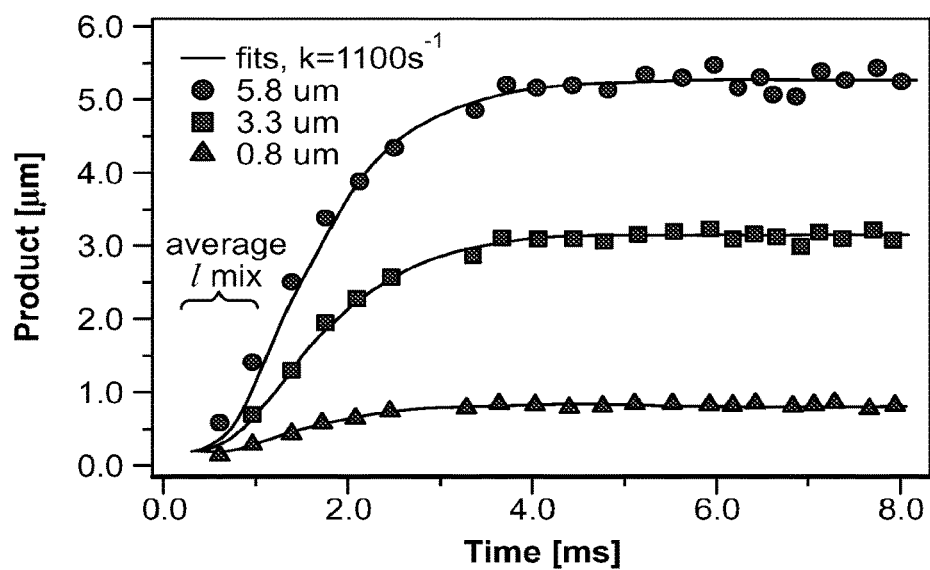

FIGS. 40A and 40B are schematic representations (left side) of a microfluidic network used to measure kinetics data for the reaction of RNase A using a fluorogenic substrate (on-chip enzyme kinetics), and plots that shows the kinetic data for the reaction between RNase A and a fluorogenic substrate.

Figures 41A, 41B, 41C:
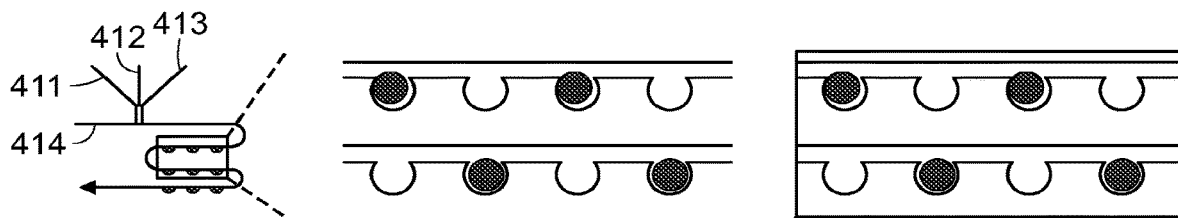

FIGS. 41A, 41B, and 41C show a photograph (FIGS. 41B and 41C) of the water droplet region of the microfluidic network (T stands for time), as well as a diagram of the microfluidic network (FIG. 41A).

Figure 42:
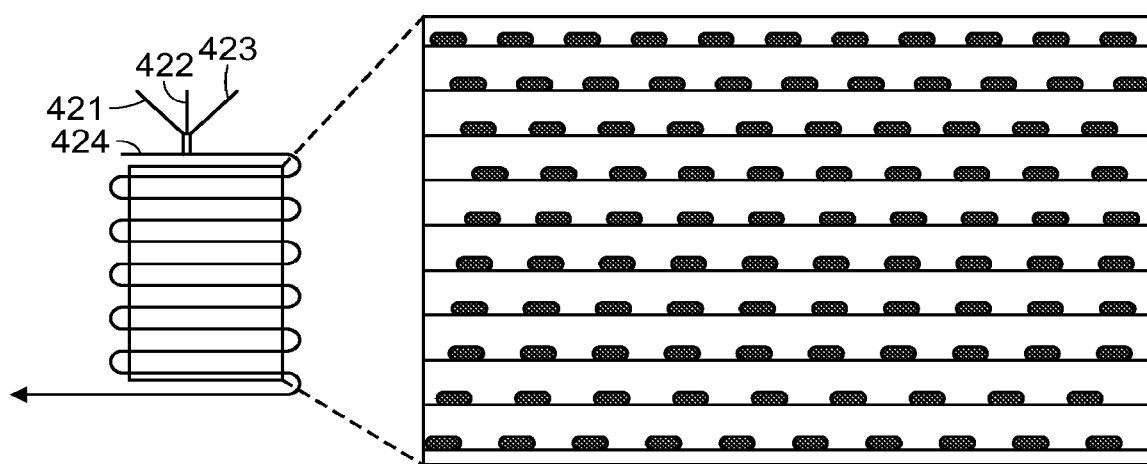

FIG. 42 shows a schematic diagram (left side) of a microfluidic network and a photograph (right side) of the ink plug region of the microfluidic network in which the gradients were formed by varying the flow rates.

Figure 43:
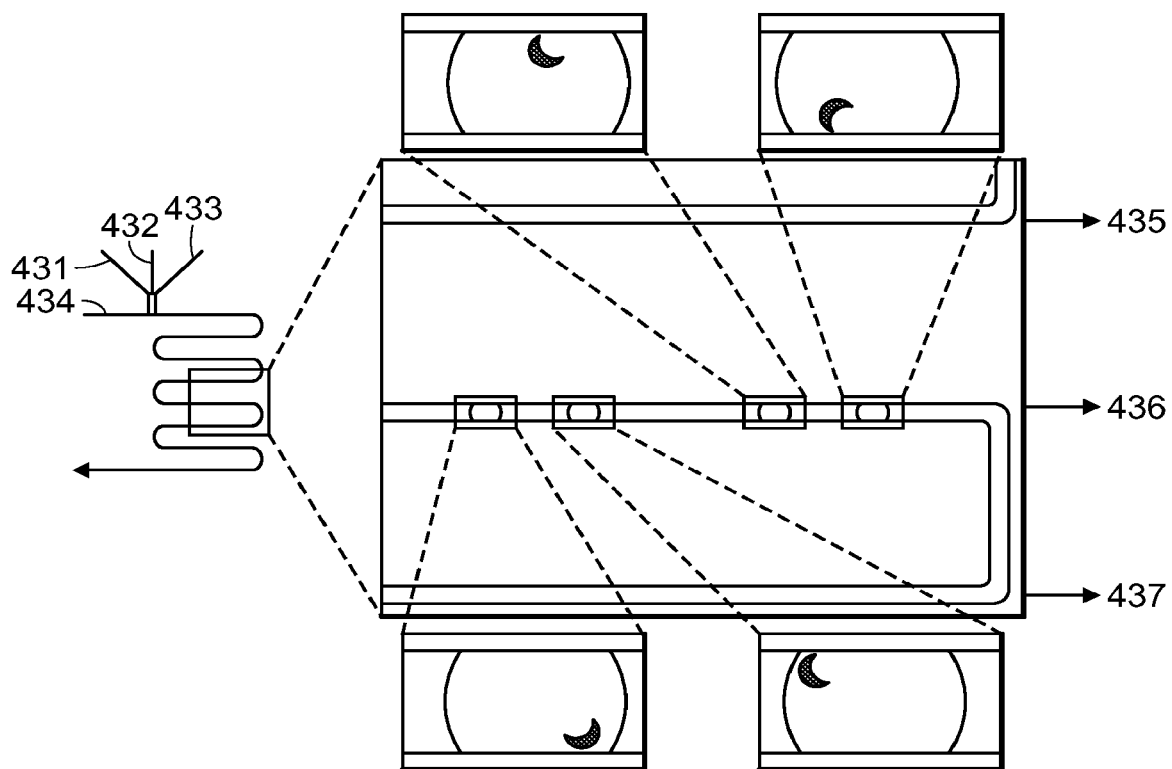
Figure 44A:
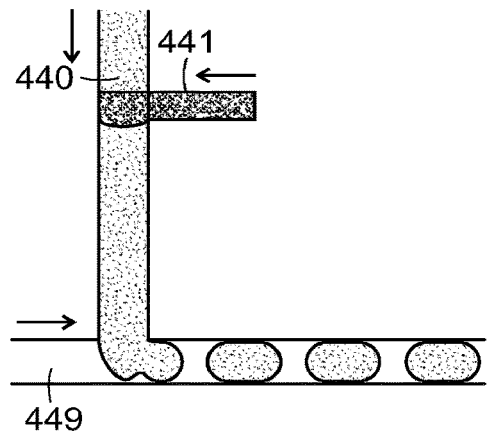
Figure 44B:
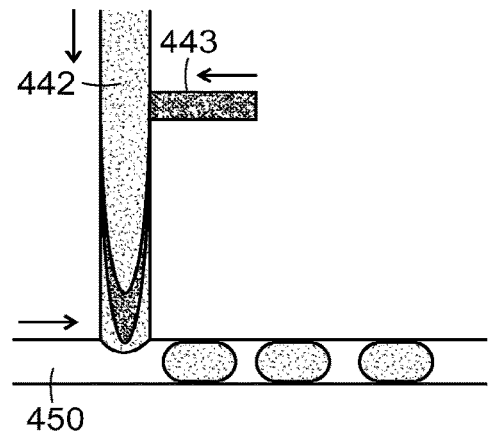
Figure 44C:
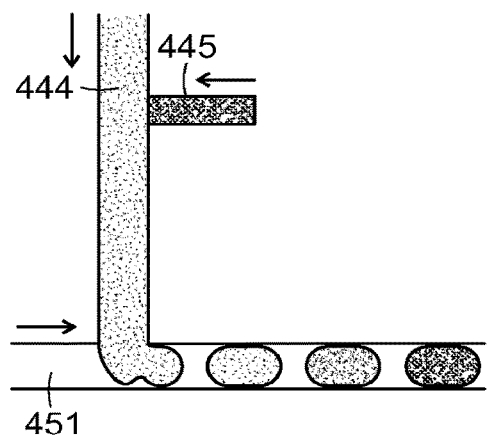
Figure 44D:
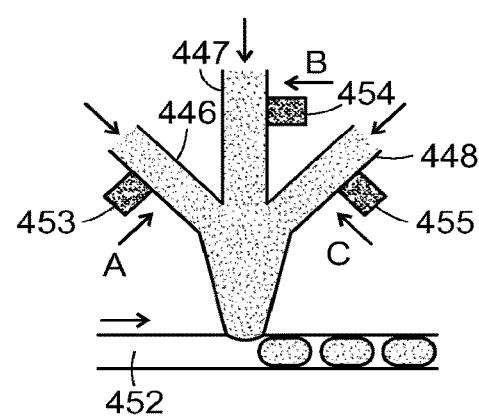

FIG. 43 shows a schematic diagram (left side) of a microfluidic network and a photograph (right side) of lysozyme crystals formed in the microfluidic network using gradients.

FIGS. 44A, 44B, 44C, and 44D are schematic illustrations showing how an initial gradient may be created by injecting a discrete aqueous sample of a reagent B into a flowing stream of water.

Figure 45A:
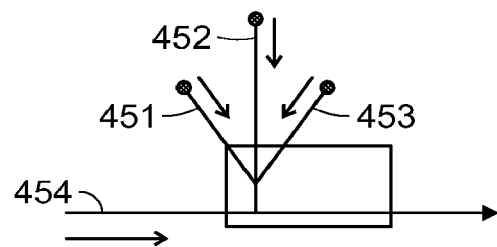
Figure 45B:
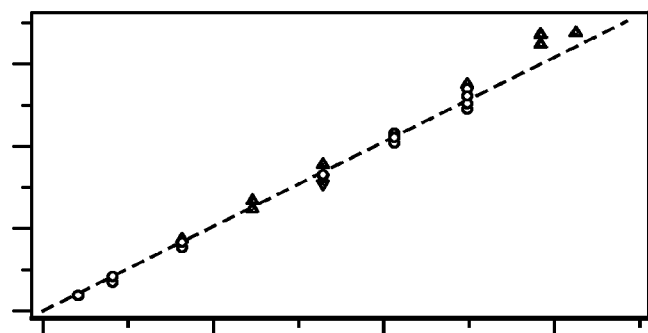

FIG. 45A shows a schematic of the microfluidic network used to demonstrate that on-chip dilutions can be accomplished by varying the flow rates of the reagents. The blue rectangle outlines the field of view for images shown in FIGS. 45C and 45D. FIG. 45B shows a graph quantifying this dilution method by measuring fluorescence of a solution of fluorescein diluted in plugs in the microchannel.

Figure 46:
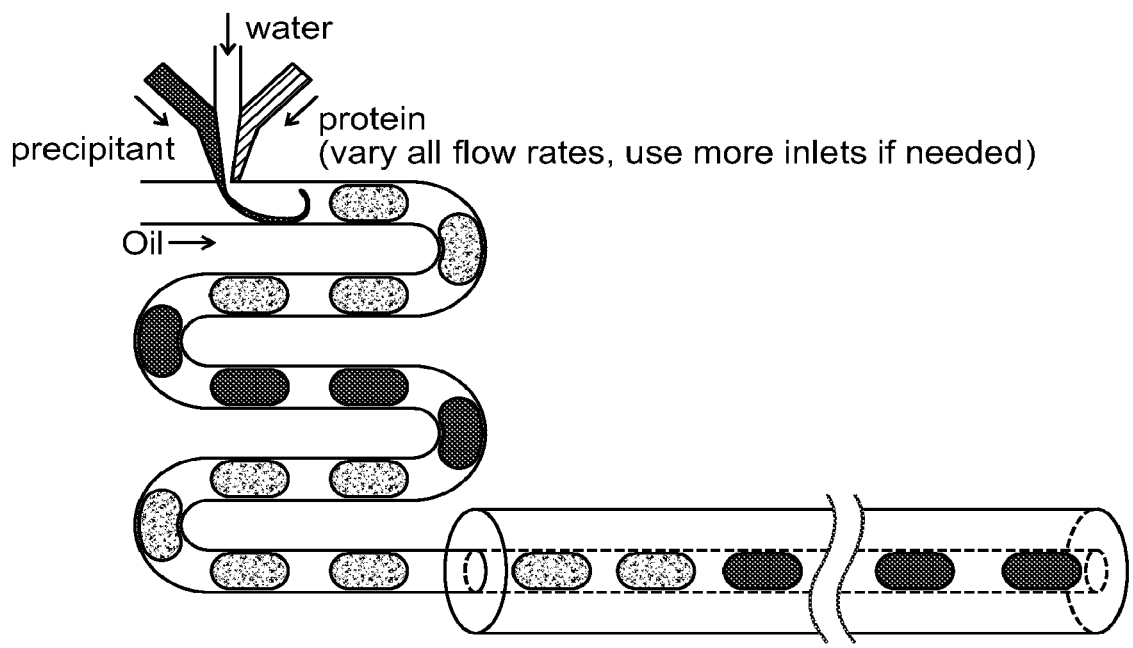

FIG. 46 shows a microbatch protein crystallization analogue scheme using a with a substrate that includes capillary tubing.

Figure 47A:
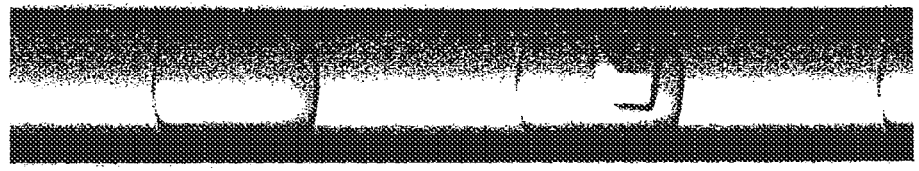

FIG. 47A shows a lysozyme crystal grown attached to a capillary tube wall.

Figure 47B:

FIG. 47B shows a thaumatin crystal grown at the interface of protein solution and oil.

FIG. 48A shows a schematic illustration of a process for direct screening of crystals in a capillary tube by x-ray diffraction.

FIG. 48B shows an x-ray diffraction pattern from a thaumatin crystal grown inside a capillary tube using a microbatch analogue method (no evaporation).

Figure 49:
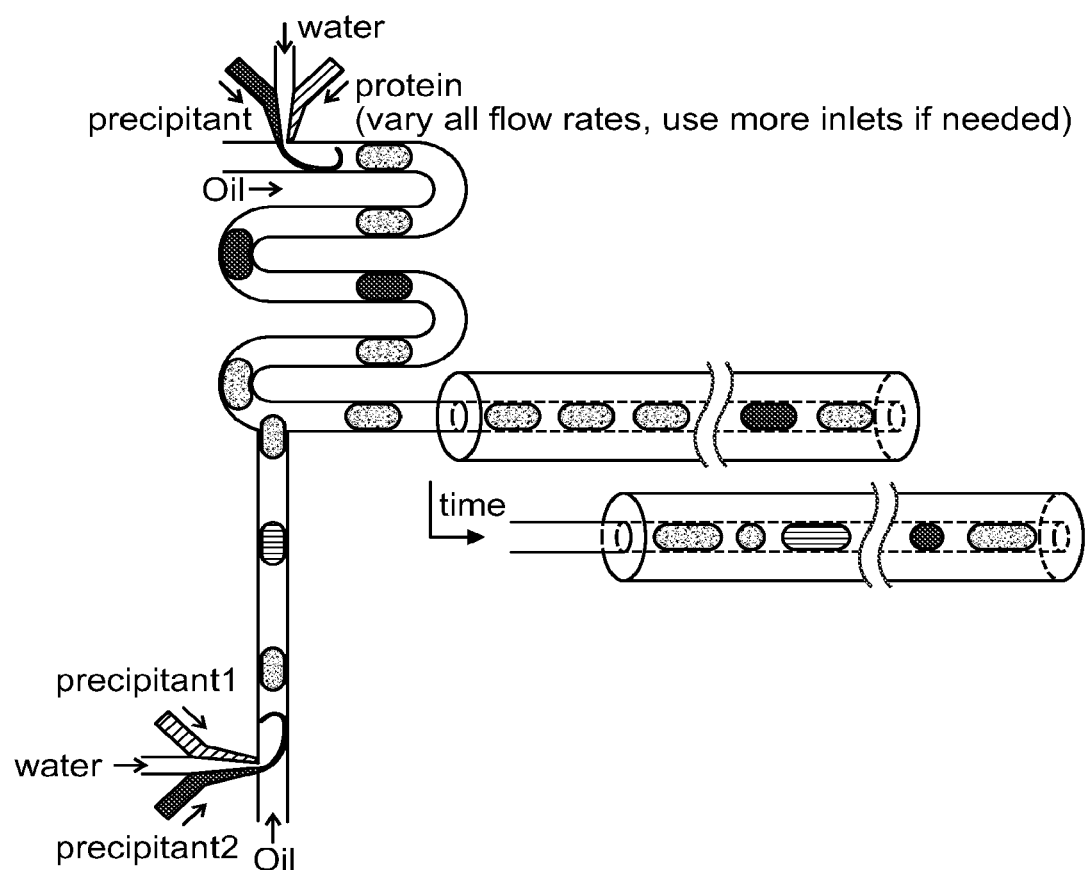

FIG. 49 shows a vapor-diffusion protein crystallization analogue scheme with a substrate that includes capillary tubing.

Figure 50A:

FIG. 50A shows vapor diffusion in droplets surrounded by FMS-121 inside a capillary right after the flow was stopped and the capillary was sealed.

Figure 50B:

FIG. 50B shows vapor diffusion in droplets surrounded by FMS-121 inside a capillary 5 days after the flow was stopped and the capillary was sealed.

Figure 51A:
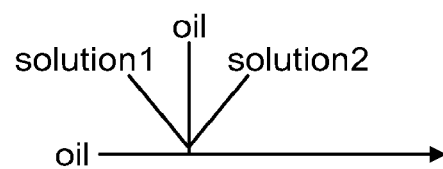

FIG. 51A shows a schematic drawing of an experimental setup to form alternating droplets.

Figure 51B:
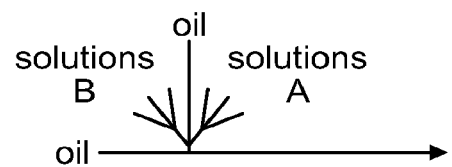

FIG. 51B shows a schematic drawing of an experimental setup to form alternating droplets where instead of single solutions 1 and 2, a set of multiple solutions A and B can be used in a similar system.

Figure 51C:
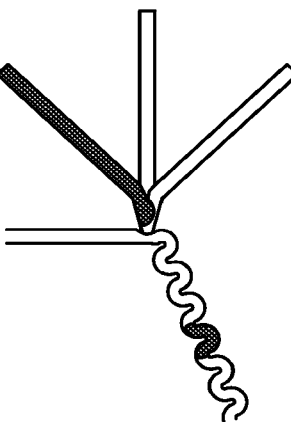

FIG. 51C shows a microphotograph illustrating the formation of alternating NaCl—Fe(SCN)3-NaCl droplets.

Figure 52A:
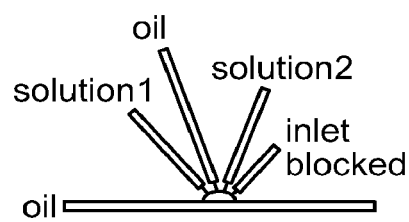

FIG. 52A shows another example of generating alternating droplets from two different aqueous solutions.

Figure 52B:
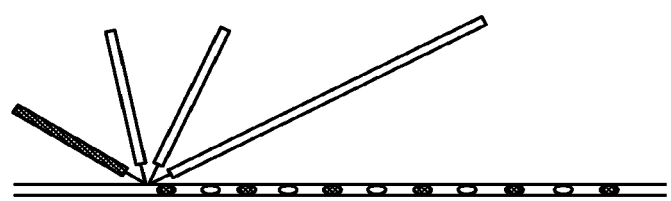

FIG. 52B shows a microphotograph illustrating the formation of alternating NaCl—Fe(SCN)3-NaCl droplets.

Figure 53A:
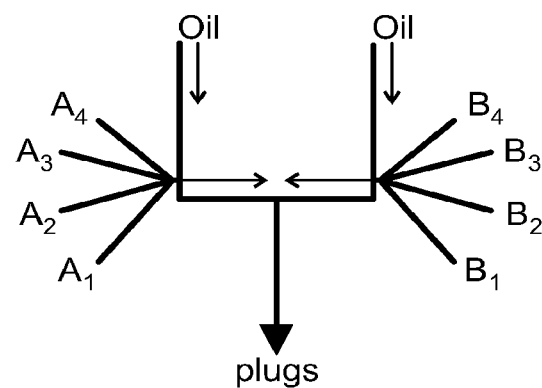
Figure 53B:
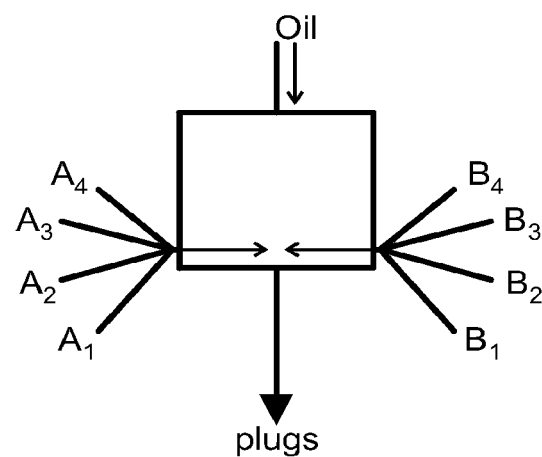
Figure 53C:
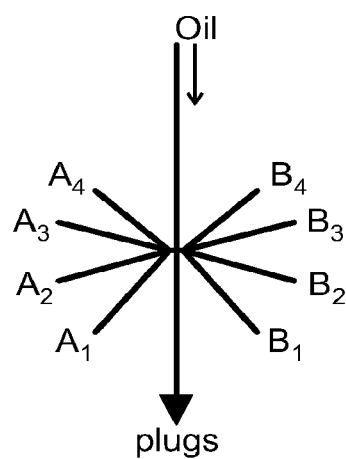

FIGS. 53A, 53B, and 53C show several representative geometries in which alternating plugs may be formed.

Figure 54A:
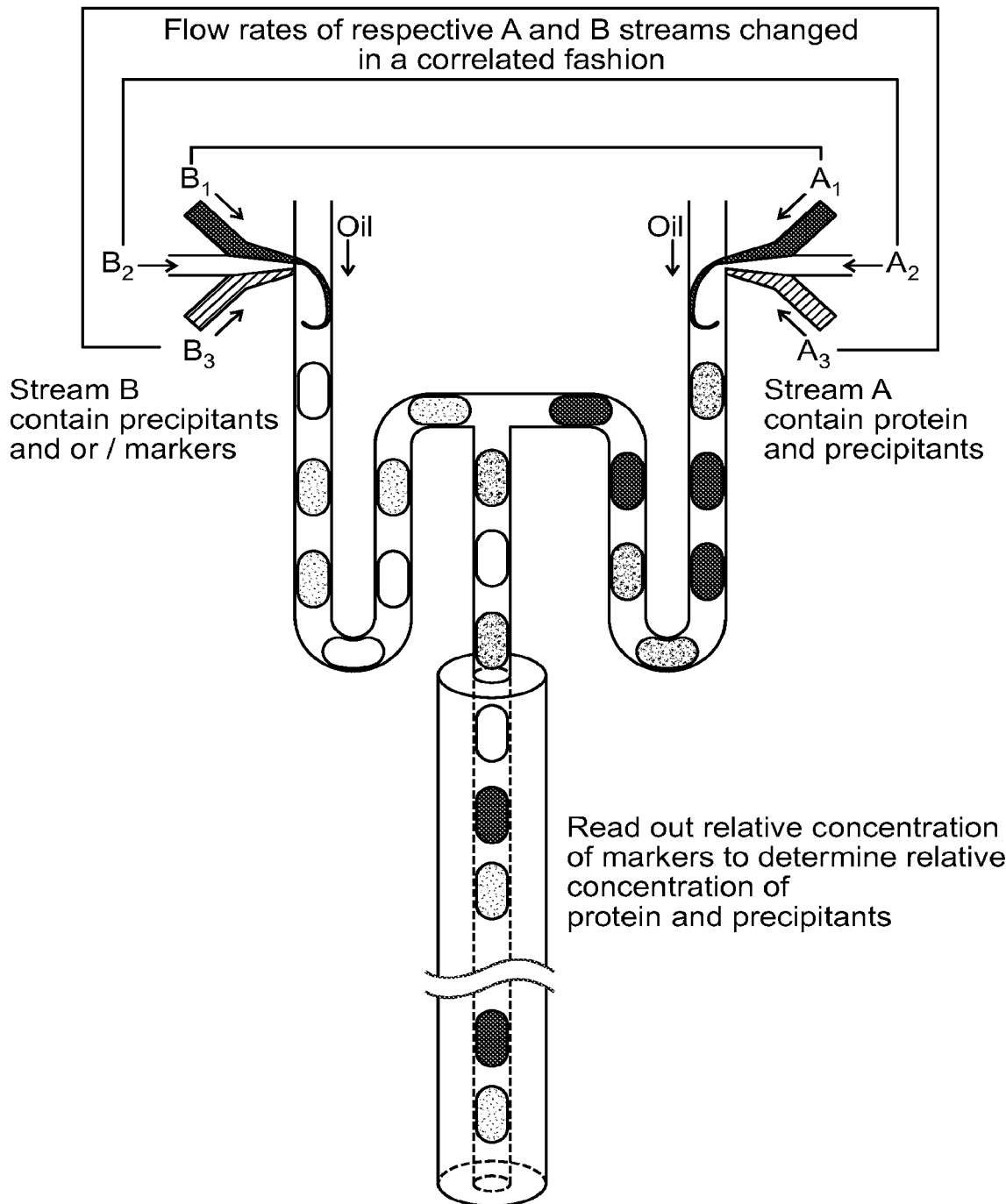
Figure 54B:
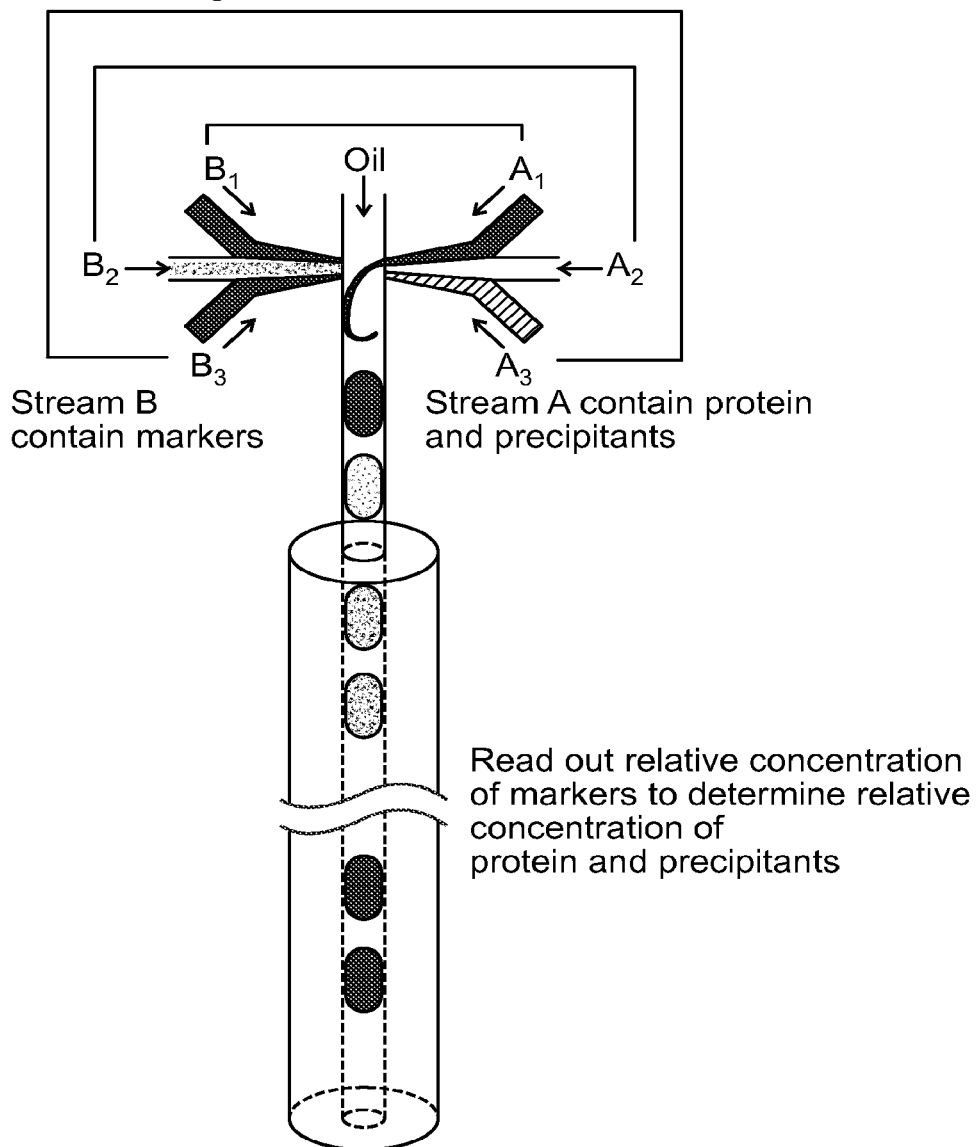

FIGS. 54A and 54B illustrate two representative geometries for indexing a component in a plug using markers.

DETAILED DESCRIPTION ACCORDING TO THE INVENTION

The term "analysis" generally refers to a process or step involving physical, chemical, biochemical, or biological analysis that includes characterization, testing, measurement, optimization, separation, synthesis, addition, filtration, dissolution, or mixing.

The term "analysis unit" refers to a part of or a location in a substrate or channel wherein a chemical undergoes one or more types of analyses.

The term "capillary tube" refers to a hollow, tube-shaped structure with a bore. The cross-sections of the tube and bore can be round, square or rectangular. The corners of the tube or bore can also be rounded. The bore diameters can range in size from 1µ to several millimeters; the outer diameters can be between about 60 µm up to several millimeters. The tube can be made using any material suitable for x-ray diffraction analysis (e.g., silica, plastic, etc.), and can additionally include coatings (e.g. polyimide) suitable for use under variable (e.g, high) temperatures or for UV transparency.

The term "carrier-fluid" refers to a fluid that is immiscible with a plug-fluid. The carrier-fluid may comprise a substance having both polar and non-polar groups or moieties.

The term "channel" refers to a conduit that is typically enclosed, although it may be at least partially open, and that allows the passage through it of one or more types of substances or mixtures, which may be homogeneous or heterogeneous, including compounds, solvents, solutions, emulsions, or dispersions, any one of which may be in the solid, liquid, or gaseous phase. A channel can assume any form or shape such as tubular or cylindrical, a uniform or variable (e.g., tapered) diameter along its length, and one or more cross-sectional shapes along its length such as rectangular, circular, or triangular. A channel is typically made of a suitable material such as a polymer, metal, glass, composite, or other relatively inert materials. As used herein, the term "channel" includes microchannels that are of dimensions suitable for use in devices. A network of channels refers to a multiplicity of channels that are typically connected or in communication with each other. A channel may be connected to at least one other channel through another type of conduit such as a valve.

The term "chemical" refers to a substance, compound, mixture, solution, emulsion, dispersion, molecule, ion, dimer, macromolecule such as a polymer or protein, biomolecule, precipitate, crystal, chemical moiety or group, particle, nanoparticle, reagent, reaction product, solvent, or fluid any one of which may exist in the solid, liquid, or gaseous state, and which is typically the subject of an analysis.

The term "detection region" refers to a part of or a location in a substrate or channel wherein a chemical is identified, measured, or sorted based on a predetermined property or characteristic.

The term "device" refers to a device fabricated or manufactured using techniques such as wet or dry etching and/or conventional lithographic techniques or a micromachining technology such as soft lithography. As used herein, the term "devices" includes those that are called, known, or classified as microfabricated devices. A device according to the invention may have dimensions between about 0.3 cm to about 15 (for 6 inch wafer) cm per side and between about 1 micrometer to about 1 cm thick, but the dimensions of the device may also lie outside these ranges.

The term "discrimination region" refers to a part of or a location in a substrate or channel wherein the flow of a fluid can change direction to enter at least one other channel such as a branch channel.

The term "downstream" refers to a position relative to an initial position which is reached after the fluid flows past the initial point. In a circulating flow device, downstream refers to a position farther along the flow path of the fluid before it crosses the initial point again. "Upstream" refers to a point in the flow path of a fluid that the fluid reaches or passes before it reaches or passes a given initial point in a substrate or device.

The term "flow" means any movement of a solid or a fluid such as a liquid. For example, the movement of plug-fluid, carrier-fluid, or a plug in a substrate, or component of a substrate according to the invention, or in a substrate or component of a substrate involving a method according to the invention, e.g., through channels of a microfluidic substrate according to the invention, comprises a flow. The application of any force may be used to provide a flow, including without limitation: pressure, capillary action, electro-osmosis, electrophoresis, dielectrophoresis, optical tweezers, and combinations thereof, without regard for any particular theory or mechanism of action.

The term "immiscible" refers to the resistance to mixing of at least two phases or fluids under a given condition or set of conditions (e.g., temperature and/or pressure) such that the at least two phases or fluids persist or remain at least partially separated even after the phases have undergone some type of mechanical or physical agitation. Phases or fluids that are immiscible are typically physically and/or chemically discernible, or they may be separated at least to a certain extent.

The term "inlet port" refers to an area of a substrate that receives plug-fluids. The inlet port may contain an inlet channel, a well or reservoir, an opening, and other features that facilitate the entry of chemicals into the substrate. A substrate may contain more than one inlet port if desired. The inlet port can be in fluid communication with a channel or separated from the channel by a valve.

The term "nanoparticles" refers to atomic, molecular or macromolecular particles typically in the length scale of approximately 1-100 nanometer range. Typically, the novel and differentiating properties and functions of nanoparticles are observed or developed at a critical length scale of matter typically under 100 nm. Nanoparticles may be used in constructing nanoscale structures and they may be integrated into larger material components, systems and architectures. In some particular cases, the critical length scale for novel properties and phenomena involving nanoparticles may be under 1 nm (e.g., manipulation of atoms at approximately 0.1 nm) or it may be larger than 100 nm (e.g., nanoparticle reinforced polymers have the unique feature at approximately 200-300 nm as a function of the local bridges or bonds between the nanoparticles and the polymer).

The term "nucleation composition" refers to a substance or mixture that includes one or more nuclei capable of growing into a crystal under conditions suitable for crystal formation. A nucleation composition may, for example, be induced to undergo crystallization by evaporation, changes in reagent concentration, adding a substance such as a precipitant, seeding with a solid material, mechanical agitation, or scratching of a surface in contact with the nucleation composition.

The term "outlet port" refers to an area of a substrate that collects or dispenses the plug-fluid, carrier-fluid, plugs or reaction product. A substrate may contain more than one outlet port if desired.

The term "particles" means any discrete form or unit of matter. The term "particle" or "particles" includes atoms, molecules, ions, dimers, polymers, or biomolecules.

The term "particulate" refers to a cluster or agglomeration of particles such as atoms, molecules, ions, dimers, polymers, or biomolecules. Particulates may comprise solid matter or be substantially solid, but they may also be porous or partially hollow. They may contain a liquid or gas. In addition, particulates may be homogeneous or heterogeneous, that is, they may comprise one or more substances or materials.

"Plugs" in accordance with the present invention are formed in a substrate when a stream of at least one plug-fluid is introduced into the flow of a carrier-fluid in which it is substantially immiscible. The flow of the fluids in the device is induced by a driving force or stimulus that arises, directly or indirectly, from the presence or application of, for example, pressure, radiation, heat, vibration, sound waves, an electric field, or a magnetic field. Plugs in accordance with the present invention may vary in size but when formed, their cross-section should be substantially similar to the cross-section of the channels in which they are formed. When plugs merge or get trapped inside plug traps, the cross-section of the plugs may change. For example, when a plug enters a wider channel, its cross-section typically increases.

Further, plugs in accordance with the present invention may vary in shape, and for example may be spherical or non-spherical. The shape of the plug may be independent of the shape of the channel (e.g., a plug may be a deformed sphere traveling in a rectangular channel). The plugs may be in the form of plugs comprising an aqueous plug-fluid containing one or more reagents and/or one or more products formed from a reaction of the reagents, wherein the aqueous plug-fluid is surrounded by a non-polar or hydrophobic fluid such as an oil. The plugs may also be in the form of plugs comprising mainly a non-polar or hydrophobic fluid which is surrounded by an aqueous fluid. The plugs may be encased by one or more layers of molecules that comprise both hydrophobic and hydrophilic groups or moieties. The term "plugs" also includes plugs comprising one or more smaller plugs, that is, plugs-within-plugs. The relative amounts of reagents and reaction products contained in the plugs at any given time depend on factors such as the extent of a reaction occurring within the plugs. Preferably, plugs contain a mixture of at least two plug fluids.

The term "plug-forming region" refers to a junction between an inlet port and the first channel of a substrate according to the invention. Preferably, the fluid introduced into the inlet port is "incompatible" (i.e., immiscible) with the fluid in the first channel so that plugs of the fluid formed in the plug-forming region are entrained into the stream of fluid from the first channel.

The term "plug-fluid" refers to a fluid wherein or using which a reaction or precipitation can occur. Typically, the plug-fluid contains a solvent and a reagent although in some embodiments at least one plug-fluid may not contain a reagent. The reagent may be soluble or insoluble in the solvent. The plug-fluid may contain a surfactant. At least two different plug-fluids are used in the present invention. When both plug-fluids contain reagents, the fluids are typically miscible, but can also be partially immiscible, so long as the reagents within each plug-fluid can react to form at least one product or intermediate.

The term "polymer" means any substance or compound that is composed of two or more building blocks ('mers') that are repetitively linked to each other. For example, a "dimer" is a compound in which two building blocks have been joined together. Polymers include both condensation and addition polymers. Typical examples of condensation polymers include polyamide, polyester, protein, wool, silk, polyurethane, cellulose, and polysiloxane. Examples of addition polymers are polyethylene, polyisobutylene, polyacrylonitrile, poly(vinyl chloride), and polystyrene. Other examples include polymers having enhanced electrical or optical properties (e.g., a nonlinear optical property) such as electroconductive or photorefractive polymers. Polymers include both linear and branched polymers.

The term "protein" generally refers to a set of amino acids linked together usually in a specific sequence. A protein can be either naturally-occurring or man-made. As used herein, the term "protein" includes amino acid sequences that have been modified to contain moieties or groups such as sugars, polymers, metalloorganic groups, fluorescent or light-emitting groups, moieties or groups that enhance or participate in a process such as intramolecular or intermolecular electron transfer, moieties or groups that facilitate or induce a protein into assuming a particular conformation or series of conformations, moieties or groups that hinder or inhibit a protein from assuming a particular conformation or series of conformations, moieties or groups that induce, enhance, or inhibit protein folding, or other moieties or groups that are incorporated into the amino acid sequence and that are intended to modify the sequence's chemical, biochemical, or biological properties. As used herein, a protein includes, but is not limited to, enzymes, structural elements, antibodies, hormones, electron carriers, and other macromolecules that are involved in processes such as cellular processes or activities. Proteins typically have up to four structural levels that include primary, secondary, tertiary, and quaternary structures.

The term "reaction" refers to a physical, chemical, biochemical, or biological transformation that involves at least one chemical, e.g., reactant, reagent, phase, carrier-fluid, or plug-fluid and that generally involves (in the case of chemical, biochemical, and biological transformations) the breaking or formation of one or more bonds such as covalent, noncovalent, van der Waals, hydrogen, or ionic bonds. The term includes typical chemical reactions such as synthesis reactions, neutralization reactions, decomposition reactions, displacement reactions, reduction-oxidation reactions, precipitation, crystallization, combustion reactions, and polymerization reactions, as well as covalent and noncovalent binding, phase change, color change, phase formation, crystallization, dissolution, light emission, changes of light absorption or emissive properties, temperature change or heat absorption or emission, conformational change, and folding or unfolding of a macromolecule such as a protein.

The term "reagent" refers to a component of a plug-fluid that undergoes or participates (e.g., by influencing the rate of a reaction or position of equilibrium) in at least one type of reaction with one or more components of other plug-fluids or a reagent-containing carrier-fluid in the substrate to produce one or more reaction products or intermediates which may undergo a further reaction or series of reactions.

A reagent contained in a plug-fluid may undergo a reaction in which a stimulus such as radiation, heat, temperature or pressure change, ultrasonic wave, or a catalyst induces a reaction to give rise to a transformation of the reagent to another reagent, intermediate, or product. A reagent may also undergo a reaction such as a phase change (e.g., precipitation) upon interaction with one or more components of other plug-fluids or a reagent-containing carrier-fluid.

The term "substrate" refers to a layer or piece of material from which devices or chips are prepared or manufactured. As used herein, the term "substrate" includes any substrate fabricated using any traditional or known microfabrication techniques. The term "substrate" also refers either to an entire device or chip or to a portion, area, or section of a device or chip which may or may not be removable or detachable from the main body of the device or chip. The substrate may be prepared from one or more materials such as glass, silicon, silicone elastomer, and polymers including, but not limited to, polypropylene or polyethylene.

The discussion below provides a detailed description of various devices and methods according to the invention for forming plugs, generating gradients in a series of plugs, varying the concentration of reagents inside plugs, rapid mixing in plugs, and scaling of mixing times. In particular, a detailed description of methods for merging, splitting and/or sorting plugs using channels, which form the bases for various applications ranging from the manufacture and analysis of various products to applications in electronics, medicine, diagnostics, and pharmaceuticals, to name a few, is discussed. Methods of detection and measurement of, among others, plugs and processes occurring within plugs are also described.

Among the various applications involving the devices and methods according to the invention are particle separation/sorting, synthesis, investigation of nonlinear and stochastic systems, nonlinear amplification using unstable autocatalytic mixtures, use of stochastic chemical systems for chemical amplification, kinetic measurements, time control of processes, increasing the dynamic range of kinetic measurements, ultrafast measurements, crystallization of proteins, and dynamic control of surface chemistry.

In addition, the devices and methods according to the invention offer a wide-range of other applications. For example, the devices and methods according to the invention provide for effective, rapid, and precise manipulation and monitoring of solutions or reactions over a range of time scales (e.g., from tens of microseconds, to hours or weeks in case of, for example, crystallization) and over a range of solution volumes (e.g., from femtoliters to hundreds of nanoliters).

In one aspect of the invention, the various devices and methods according to the invention are used to overcome one or more of the following problems involving microfluidics. First, the substantial dispersion of solutes in microfluidic channels increases reagent consumption and makes experiments or measurements over long time scales (e.g., minutes to hours) difficult to perform. Various devices and methods according to the invention are intended to overcome this problem by localizing reagents inside plugs that are encapsulated by an immiscible carrier-fluid.

Second, slow mixing of solutions renders experiments, tests, or reactions involving very short time scales (e.g., tens of milliseconds and below) either difficult or impossible to perform with existing technologies. In addition, turbulence-based mixing techniques prohibitively increase sample consumption. In accordance with the present invention, this problem is preferably addressed by conducting the mixing process inside plugs. Rather than relying on turbulence, the various devices and methods according to the invention preferably rely on chaotic advection to accelerate the mixing process. An advantage provided by chaotic advection is that it is expected to operate efficiently in both small and large channels.

Third, achieving control over the chemistry of internal surfaces of devices can be very important at small scales. Thus, being able to control surface chemistry in small devices for example is highly desirable. In accordance with the devices and methods according to the invention, the surface chemistry to which solutions are exposed is preferably controlled through a careful selection of surfactants that are preferably designed to assemble at the interface between the plugs and the immiscible fluid that surrounds them.

Devices and methods of the invention are also provided for use in traditional areas of microfluidics where, for example, miniaturization and speed are important. Thus, the devices and methods according to the invention may be used to develop various tools such as those for high-throughput chemical or biophysical measurements, chemical synthesis, particle formation, and protein crystallization. They may also be used in high-throughput screening, combinatorial synthesis, analysis, and diagnostics, either as a self-contained platform, or in combination with existing technologies particularly those that rely on the use of immiscible fluid flows.

Importantly, the devices of the invention can be adapted to work with automation and robotic technology. They may be used, for example, as a basis for ultra-high throughput automated systems for structural and functional characterization of biological molecules. Thus, the various devices and methods according to the invention provide rapid, economical, and accessible means of synthesis, analysis, and measurements in the fields of biology, chemistry, biophysics, bioengineering, and medicine (e.g., for diagnostics).

The devices and methods of the invention have numerous other possible applications. For example, chaotic mixing at low values of Reynolds number can be exploited as an important tool for controlling unstable chemical reactions. In addition, the systems and devices of the invention may be used for controlling and/or monitoring reactions that generate highly unstable (or explosive) intermediates. They can also be valuable for controlling or monitoring reactions or processes involving autocatalytic reactions. For example, pure hydrogen peroxide ($H_2O_2$) is an inexpensive and highly effective oxidant, but its autocatalytic decomposition often leads to explosions upon storage and handling. In the microfluidic systems of the invention, $H_2O_2$ is preferably generated in-situ, stabilized by the chaotic flow, and used to destroy chemical and biological warfare agents. Because the unstable mixtures in these systems are localized inside plugs formed in accordance with the invention, occasional autocatalytic decomposition in one or more plugs is kept localized within those plugs thereby preventing a catastrophic reaction involving the whole system. In addition, large arrays of microfluidic reactors may be operated in parallel to provide substantial throughput.

It is also possible to couple multiple autocatalytic reactions in a single network using the devices and methods according to the invention. For example, a sample plug could be split into many smaller plugs and forwarded to individual amplification cascades. Because the contents of the cascades' outflows exhibit patterns that correspond to the patterns of analytes present in these systems, these patterns could be analyzed using artificial neural network (ANN) (Jackson, R. B. a. T. *Neural Computing: An Introduction*, Hilger, N.Y., 1991; Zornetzer et al., *An Introduction to Neural and Electronic Networks*, Academic Press, San Diego, Calif., 1990.) algorithms. For example, patterns that arise in blood or saliva analysis may correspond to certain normal or abnormal (e.g., disease, fatigue, infection, poisoning) conditions involving, for example, human and animals.

Moreover, it may be possible to create intelligent microfluidic systems in accordance with the invention, where the nonlinear chemical reactions perform not only detection, but also analysis using ANN algorithms. For example, after amplification, the channels of the present invention typically will contain sufficient amounts of material to operate hydrogel-based valves (Liu et al., "Fabrication and characterization of hydrogel-based microvalves," J. Microelectromech. Syst. 2002, vol. 1, pp. 45-53; Yu et al., "Responsive biomimetic hydrogel valve for microfluidics," Appl. Phys. Lett. 2001, vol. 78, pp. 2589-2591; Beebe et al., "Functional hydrogel structures for autonomous flow control inside microfluidic channels," Nature, 2000, vol. 404, 588.). These valves can be used to control flows inside the system as a function of the sample plug composition. Feedforward and even feedback (e.g., by using the hydrogel valves to control the flow of the input streams) networks may thus be created and used for analysis. Such nonlinear networks may be used not only to recognize patterns pre-programmed by the connectivity of the channels (Hjelmfelt et al., "Pattern-Recognition in Coupled Chemical Kinetic Systems," Science, 1993, 260, 335-337.) but also to learn patterns by reconfiguring themselves (Jackson, R. B. a. T. Neural Computing: An Introduction, Hilger, N.Y., 1991; Zornetzer et al., An Introduction to Neural and Electronic Networks, Academic Press, San Diego, Calif., 1990.). Such intelligent microfluidic devices could have unprecedented capabilities for fully autonomous detection, analysis, and signal processing, perhaps surpassing those of biological and current man-made systems.

The devices and methods of the invention are also useful in genomics and proteomics, which are used to identify thousands of new biomolecules that need to be characterized, or are available only in minute quantities. In particular, the success of genomics and proteomics has increased the demand for efficient, high-throughput mechanisms for protein crystallization. X-ray structure determination remains the predominant method of structural characterization of proteins. However, despite significant efforts to understand the process of crystallization, macromolecular crystallization largely remains an empirical field, with no general theory to guide a rational approach. As a result, empirical screening has remained the most widely used method for crystallizing proteins.

The following areas also provide applications of the devices and methods according to the invention. For example, a number of problems still beset high-throughput kinetics and protein crystallization. When it comes to determining protein structure and quantitatively ascertaining protein interactions, there are at least two technological challenges: (1) most robotic technology still only automate existing methods and are often too expensive for a small research laboratory; and (2) there remains the need for conceptually new methods that provide greater degree of control over the crystallization process. In addition, setting up and monitoring crystallization trials typically involve handling of sub-microliter volumes of fluids over periods ranging from seconds to days.

Thus, various devices and methods according to the present invention are designed to provide novel and efficient means for high-throughput crystallization of soluble and membrane proteins. In addition to being a simple and economical method of setting up thousands of crystallization trials in a matter of minutes, a system according to the invention will enable unique time control of processes such as the mixing and nucleation steps leading to crystallization. A system according to the present invention may also be used to control protein crystallization by controlling not only short time-scale events such as nucleation but also long time-scale events such as crystal growth.

Further, the devices and methods of the present invention may be used in high-throughput, kinetic, and biophysical measurements spanning the $10^{-5}$-$10^7$ second time regime. Preferably, the various devices and methods according to the present invention require only between about a few nanoliters to about a few microliters of each solution. Applications of such devices and methods include studies of enzyme kinetics and RNA folding, and nanoparticle characterization and synthesis, which are discussed in detail below.

Channels and Devices

In one aspect of the invention, a device is provided that includes one or more substrates comprising a first channel comprising an inlet separated from an outlet; optionally, one or more secondary channels (or branch channels) in fluid communication with the first channel, at least one carrier-fluid reservoir in fluid communication with the first channel, at least two plug-fluid reservoirs in fluid communication with the first channel, and a means for applying continuous pressure to a fluid within the substrate.

A device according to the invention preferably comprises at least one substrate.

A substrate may include one or more expansions or areas along a channel wherein plugs can be trapped. The substrates of the present invention may comprise an array of connected channels.

The device may have one or more outlet ports or inlet ports. Each of the outlet and inlet ports may also communicate with a well or reservoir. The inlet and outlet ports may be in fluid communication with the channels or reservoirs that they are connecting or may contain one or more valves. Fluid can be introduced into the channels via the inlet by any means. Typically, a syringe pump is used, wherein the flow rate of the fluid into the inlet can be controlled.

A plug-forming region generally comprises a junction between a plug-fluid inlet and a channel containing the carrier-fluid such that plugs form which are substantially similar in size to each other and which have cross-sections which are substantially similar in size to the cross-section of the channel in the plug-forming region. In one embodiment, the substrate may contain a plurality of plug-forming regions.

The different plug-forming regions may each be connected to the same or different channels of the substrate. Preferably, the sample inlet intersects a first channel such that the pressurized plug fluid is introduced into the first channel at an angle to a stream of carrier-fluid passing through the first channel. For example, in preferred embodiments, the sample inlet and first channel intercept at a T-shaped junction; i.e., such that the sample inlet is perpendicular (i.e. at an angle of 90°) to the first channel. However, the sample inlet may intercept the first channel at any angle.

A first channel may in turn communicate with two or more branch channels at another junction or "branch point", forming, for example, a T-shape or a Y-shape. Other shapes and channel geometries may be used as desired. In exemplary embodiments the angle between intersecting channels is in the range of from about 60° to about 120°. Particular exemplary angles are 45°, 60°, 90°, and 120°. Precise boundaries for the discrimination region are not required, but are preferred.

The first and branch channels of the present invention can, each independently, be straight or have one or more bends. The angle of a bend, relative to the substrate, can be greater than about 10°, preferably greater than about 135°, 180°, 270°, or 360°.

In one embodiment of the invention, a substrate comprises at least one inlet port in communication with a first channel at or near a plug-forming region, a detection region within or coincident with all or a portion of the first channel or plug-forming region, and a detector associated with the detection region. In certain embodiments the device may have two or more plug-forming regions. For example, embodiments are provided in which the analysis unit has a first inlet port in communication with the first channel at a first plug-forming region, a second inlet port in communication with the first channel at a second plug-forming region (preferably downstream from the first plug-forming region), and so forth.

In another embodiment, a substrate according to the invention may comprise a first channel through which a pressurized stream or flow of a carrier-fluid is passed, and two or more inlet channels which intersect the first channel at plug-forming regions and through which a pressurized stream or flow of plug fluids pass. Preferably, these inlet channels are parallel to each other and each intercept the first channel at a right angle. In specific embodiments wherein the plugs introduced through the different plug forming regions are mixed, the inlet channels are preferably close together along the first channel. For example, the first channel may have a diameter of 60 μm that tapers to 30 μm at or near the plug-forming regions. The inlet channels then also preferably have a diameter of about 30 μm and, in embodiments where plug mixing is preferred, are separated by a distance along the first channel approximately equal to the diameter of the inlet channel (i.e., about 30 μm).

In an embodiment according to the invention, the substrate also has a detection region along a channel. There may be a plurality of detection regions and detectors, working independently or together, e.g., to analyze one or more properties of a chemical such as a reagent.

A detection region is within, communicating, or coincident with a portion of a first channel at or downstream of the plug-forming region and, in sorting embodiments, at or upstream of the discrimination region or branch point. Precise boundaries for the detection region are not required, but are preferred.

A typical substrate according to the invention comprises a carrier-fluid inlet that is part of and feeds or communicates directly with a first channel, along with one or more plug fluid inlets in communication with the first channel at a plug-forming region situated downstream from the main inlet (each different plug-fluid inlet preferably communicates with the first channel at a different plug-forming region).

Plugs formed from different plug-fluids or solutions may be released in any order. For example, an aqueous solution containing a first plug-fluid may be released through a first inlet at a first plug-forming region. Subsequently, plugs of an aqueous second plug-fluid may be released through a second inlet at a second plug-forming region downstream of the first inlet.

Fabrication of Channels, Substrates, and Devices

The substrates and devices according to the invention are fabricated, for example by etching a silicon substrate, chip, or device using conventional photolithography techniques or micromachining technology, including soft lithography. The fabrication of microfluidic devices using polydimethylsiloxane has been previously described. These and other fabrication methods may be used to provide inexpensive miniaturized devices, and in the case of soft lithography, can provide robust devices having beneficial properties such as improved flexibility, stability, and mechanical strength. Preferably, when optical detection is employed, the invention also provides minimal light scatter from, for example, plugs, carrier-fluid, and substrate material. Devices according to the invention are relatively inexpensive and easy to set up.

Machining methods (e.g., micromachining methods) that may be used to fabricate channels, substrates, and devices according to the invention are well known in the art and include film deposition processes, such as spin coating and chemical vapor deposition, laser fabrication or photolithographic techniques, or etching methods, which may be performed either by wet chemical or plasma processes.

Channels may be molded onto optically transparent silicone rubber or polydimethylsiloxane (PDMS), preferably PDMS. This can be done, for example, by casting the channels from a mold by etching the negative image of these channels into the same type of crystalline silicon wafer used in semiconductor fabrication. The same or similar techniques for patterning semiconductor features can be used to form the pattern of the channels. In one method of channel fabrication, an uncured PDMS is poured onto the molds placed in the bottom of, for example, a Petri dish. To accelerate curing, the molds are preferably baked. After curing the PDMS, it is removed from on top of the mold and trimmed. Holes may be cut into the PDMS using, for example, a tool such as a cork borer or a syringe needle. Before use, the PDMS channels may be placed in a hot bath of HCl if it is desired to render the surface hydrophilic. The PDMS channels can then be placed onto a microscope cover slip (or any other suitable flat surface), which can be used to form the base/floor or top of the channels.

A substrate according to the invention is preferably fabricated from materials such as glass, polymers, silicon microchip, or silicone elastomers. The dimensions of the substrate may range, for example, between about 0.3 cm to about 7 cm per side and about 1 micron to about 1 cm in thickness, but other dimensions may be used.

A substrate can be fabricated with a fluid reservoir or well at the inlet port, which is typically in fluid communication with an inlet channel. A reservoir preferably facilitates introduction of fluids into the substrate and into the first channel. An inlet port may have an opening such as in the floor of the substrate to permit entry of the sample into the device. The inlet port may also contain a connector adapted to receive a suitable piece of tubing, such as Teflon® tubing, liquid chromatography or HPLC tubing, through which a fluid may be supplied. Such an arrangement facilitates introducing the fluid under positive pressure in order to achieve a desired pressure at the plug-forming region.

A substrate containing the fabricated flow channels and other components is preferably covered and sealed, preferably with a transparent cover, e.g., thin glass or quartz, although other clear or opaque cover materials may be used. Silicon is a preferred substrate material due to well-developed technology permitting its precise and efficient fabrication, but other materials may be used, including polymers such as polytetrafluoroethylenes. Analytical devices having channels, valves, and other elements can be designed and fabricated from various substrate materials. When external radiation sources or detectors are employed, the detection region is preferably covered with a clear cover material to allow optical access to the fluid flow. For example, anodic bonding of a silicon substrate to a PYREX® cover slip can be accomplished by washing both components in an aqueous $H_2SO_4/H_2O_2$ bath, rinsing in water, and then, for example, heating to about 350° C. while applying a voltage of 450 V.

A variety of channels for sample flow and mixing can be fabricated on the substrate and can be positioned at any location on the substrate, chip, or device as the detection and discrimination or sorting points. Channels can also be designed into the substrate that place the fluid flow at different times/distances into a field of view of a detector. Channels can also be designed to merge or split fluid flows at precise times/distances.

A group of manifolds (a region consisting of several channels that lead to or from a common channel) can be included to facilitate the movement of plugs from different analysis units, through the plurality of branch channels and to the appropriate solution outlet. Manifolds are preferably fabricated into the substrate at different depth levels. Thus, devices according to the invention may have a plurality of analysis units that can collect the solution from associated branch channels of each unit into a manifold, which routes the flow of solution to an outlet. The outlet can be adapted for receiving, for example, a segment of tubing or a sample tube, such as a standard 1.5 ml centrifuge tube. Collection can also be done using micropipettes.

Methods of Forming Plugs

The various channels, substrates, and devices according to the invention are primarily used to form and manipulate plugs.

In a preferred embodiment, plug-fluids do not significantly mix at or before they are introduced into the first channel. The plug-fluids may form distinct laminar streams at or before the inlet. They may be separated by an additional fluid. Alternatively, they may be introduced into the carrier-fluid via inlets of differing size. The concentration of plug-fluids in the plugs may be adjusted by adjusting volumetric flow rates of the plug-fluids. Further, the diameters of the first channel and the branch channel(s) may differ.

Figures 1, 2A:
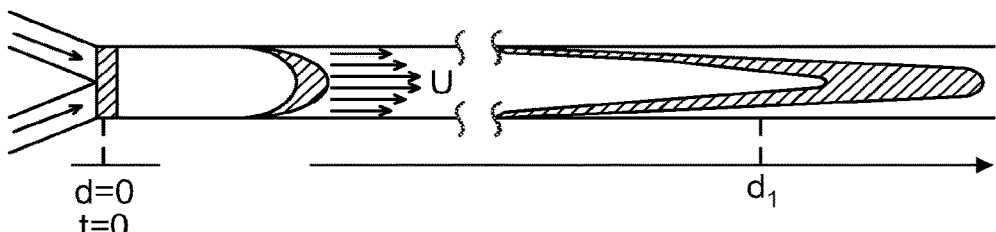
Figures 2, 2A:
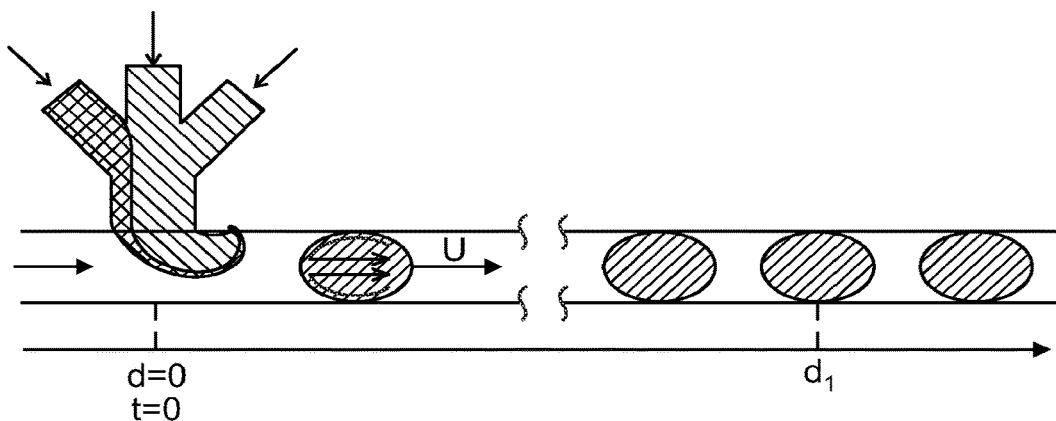

FIG. 2A is a schematic diagrams contrasting laminar flow transport and plug transport in a channel. In the lower figure which depicts the transport of plugs), two aqueous reagents (marked in red and blue) form laminar streams that are separated by a "divider" aqueous stream. The three streams enter a channel with flowing oil, at which point plugs form and plug fluids mix. During plug transport, rapid mixing of the plug-fluids typically occurs within the plugs. In contrast, in laminar flow transport, fluid mixing occurs slowly, and with high dispersion, as shown in the upper figure). In the upper figure, the time t at a given point $d_1$ can be estimated from $t_1 \approx d_1/U$, where dl is the distance from d=0 and U is the flow velocity. In the lower figure, the time t is given by $t_1 = d_1/U$.

Figures 1, 2B:
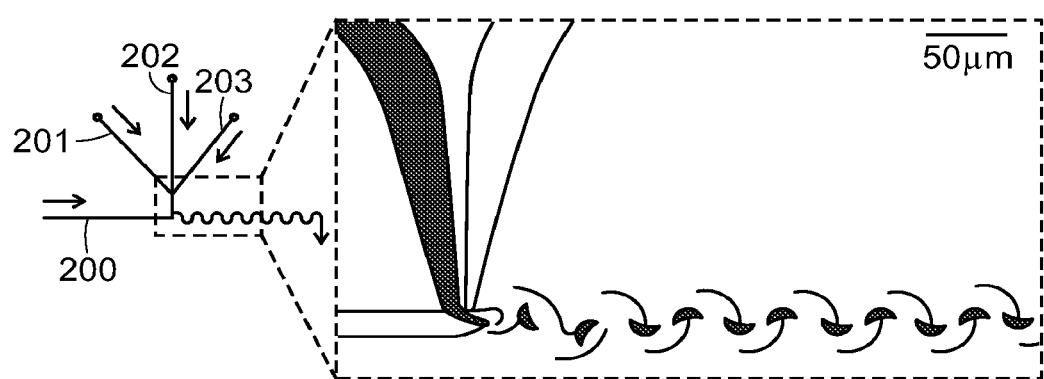
Figures 2, 2B:
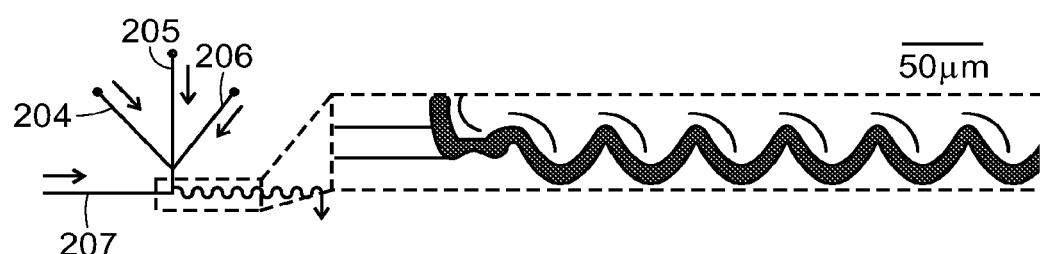
Figure 3A:
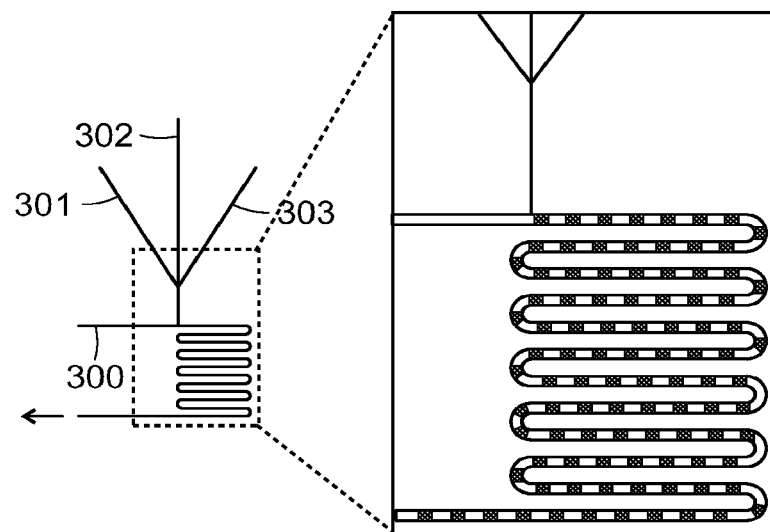
Figure 3B:
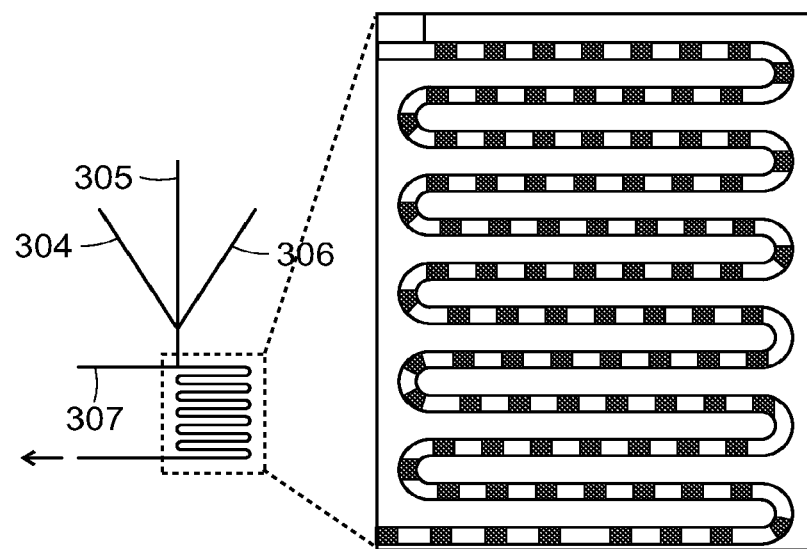
Figure 4:
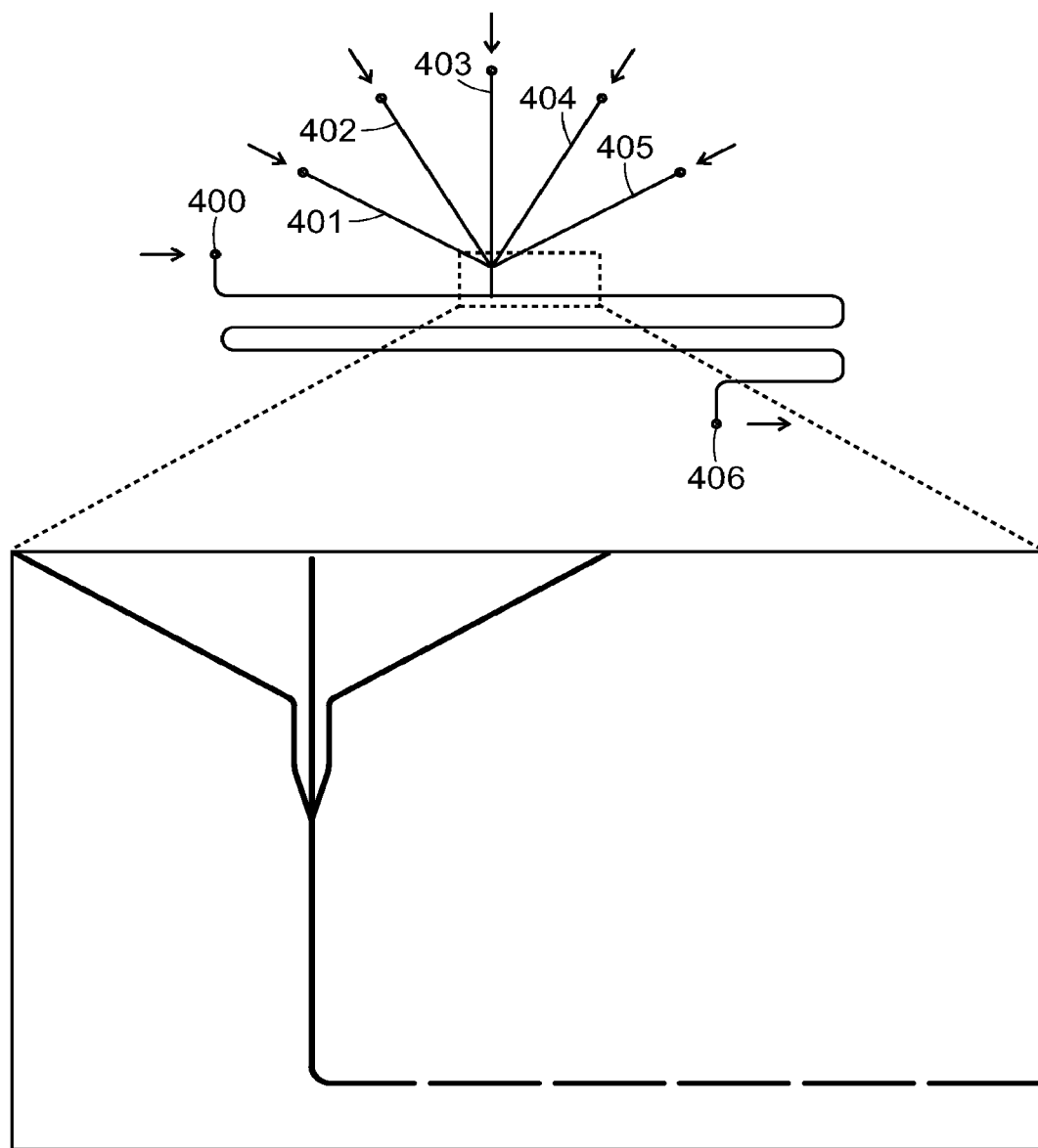

FIG. 2B shows a photograph and a schematic diagram that depict mixing in water/oil plugs (upper schematic and photograph) and in laminar streams (lower schematic and photograph) comprising only aqueous plug-fluids. The oil (carrier-fluid in this case) is introduced into channel 200 of a substrate. Instead of oil, water is introduced into the corresponding channel 207 in the case of mixing using laminar streams. The three aqueous plug-fluids are introduced by inlet ports 201, 202, 203 into the carrier-fluid (and by inlet ports 204, 205, 206 in the case of laminar streams). A preferred scheme is one in which the aqueous plug-fluids initially coflow preferably along a short or minimal distance before coming in contact with the carrier-fluid. In a preferred embodiment, the distance traversed by the coflowing plug-fluids is approximately or substantially equal to the width of the channel.

The middle or second aqueous plug-fluid in the top figure may be plain water, buffer, solvent, or a different plug-fluid. The middle aqueous plug-fluid would preferably initially separate the two other aqueous plug-fluids before the aqueous fluids come into contact with the carrier-fluid. Thus, the intervening aqueous plug-fluid would prevent, delay, or minimize the reaction or mixing of the two outer aqueous plug-fluids before they come in contact with the carrier-fluid. The plugs that form in the plug-forming region can continue along an unbranched channel, can split and enter a channel, can merge with plugs from another channel, or can exit the substrate through an exit port. It can be seen in FIG. 2 that, in the absence of an oil, the aqueous plug-fluids flow in laminar streams without significant mixing or with only partial mixing. In contrast, plug-fluids mix substantially or completely in the plugs.

Figures 1, 1B, 2, 3:
FIGS. 3A and 3B show photographs (right side) and schematic diagrams (left side) that depict a stream of plugs from an aqueous plug-fluid and an oil (carrier-fluid) in curved channels at flow rates of 0.5 µL/min (FIG. 3A) and 1.0 µL/min (FIG. 3B).

FIG. 3 shows photographs and schematic diagrams that depict a stream of plugs from an aqueous plug-fluid and an oil (carrier-fluid) in curved channels at flow rates of 0.5 µL/min (top schematic diagram and photograph) and 1.0 µL/min (bottom schematic diagram and photograph). This scheme allows enhanced mixing of reagents in the elongated plugs flowing along a curved channel with smooth corners or curves. The carrier-fluid is introduced into an inlet port 300, 307 of a substrate while the three aqueous plug-fluids are introduced in separate inlet ports 301-306. As in FIG. 2, a preferred scheme would be one in which the plug-fluids initially coflow preferably along a short or minimal distance before coming in contact with the carrier-fluid. In a preferred embodiment, the distance traversed by the coflowing plug-fluids (e.g., aqueous plug-fluids) is approximately or substantially equal to the width of the channel. The middle or second aqueous plug-fluid may comprise plain water, buffer, solvent, or a plug-fluid, and the middle aqueous plug-fluid preferably initially separates the two other aqueous plug-fluids before the aqueous plug-fluids come into contact with the carrier-fluid which, in this case, is an oil. Thus, the intervening aqueous plug-fluid would prevent, delay, or minimize the reaction or mixing of the two outer aqueous plug-fluids before they come in contact with the oil (or carrier-fluid).

Figures 1, 1B, 2, 3, 4:
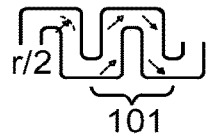
FIG. 4 shows a photograph (lower portion) and a schematic diagram (upper portion) that illustrate plug formation through the injection of oil and multiple plug-fluids.
Figure 5:
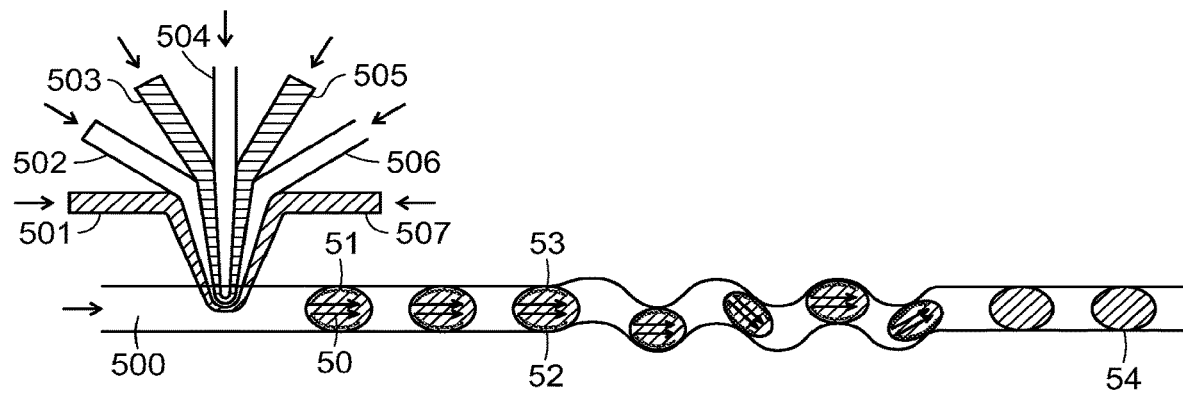
FIG. 5 is a schematic diagram that illustrates a two-step reaction in which plugs are formed through the injection of oil and multiple plug-fluids using a combination of different geometries for controlling reactions and mixing.

FIG. 4 shows a photograph and schematic diagram that illustrate plug formation through the injection of oil and multiple plug-fluids. Although FIG. 4 shows five separate plug-fluids, one may also separately introduce less than or more than five plug-fluids into the substrate. The reagents or solvents comprising the plug-fluids may be different or some of them may be identical or similar. As in FIG. 2, the oil is introduced into an inlet port 400 of a substrate while the aqueous plug-fluid is introduced in separate inlet ports 401-405. The water plugs then flow through exit 406. A preferred scheme is one in which the aqueous plug-fluids would initially coflow preferably along a short or minimal distance before coming in contact with the oil. In a preferred embodiment, the distance traversed by the coflowing plug-fluids is approximately or substantially equal to the width of the channel. One or more of the aqueous plug-fluids may comprise plain water, buffer, solvent, or a plug-fluid, and at least one aqueous plug-fluid would preferably initially separate at least two other aqueous streams before the aqueous plug-fluid comes into contact with the oil. Thus, the at least one intervening aqueous plug-fluid would prevent, delay, or minimize the reaction or mixing of the two outer aqueous streams before the aqueous streams come in contact with the oil. FIG. 5 shows a microfluidic network, which is similar to that shown in FIG. 4, in which several reagents can be introduced into the multiple inlets. In addition, FIG. 5 shows a channel having a winding portion through which the plugs undergo mixing of the four reagents A, B, C, and D. As shown in FIG. 5, the reagents A, B, C, and D are introduced into inlet ports 501, 503, 505, and 507, while aqueous streams are introduced into inlet ports 502, 504, 506. FIG. 5 shows plugs through the various stages of mixing, wherein mixture 50 corresponds to the initial A+B mixture, mixture 51 corresponds to the initial C+D mixture, mixture 52 corresponds to the mixed A+B mixture, mixture 53 corresponds to the mixed C+D mixture, and mixture 54 corresponds to the A+B+C+D mixture.

The formation of the plugs preferentially occurs at low values of the capillary number C.n., which is given by the equation $$C.n. = U\mu/\gamma \qquad \text{Eqn. (1)}$$

where U is the flow velocity, It is the viscosity of the plug fluid or carrier-fluid, and $\gamma$ is the surface tension at the water/surfactant interface.

The plugs may be formed using solvents of differing or substantially identical viscosities. Preferably, the conditions and parameters used in an experiment or reaction are such that the resulting capillary number lies in the range of about $0.001 \leq C.n. \leq$ about 10. Preferably, the values of parameters such as viscosities and velocities are such that plugs can be formed reliably. Without wishing to be bound by theory, it is believed that as long as flow is not stopped, the C.n. is $\leq$ about 0.2, and as long as the surface tension of the plug-fluid/carrier-fluid interface is lower than the surface tension of the solution/wall interface, plug formation will persist. The C.n. number is zero when flow is stopped.

In one embodiment, in which perfluorodecaline was used as the carrier-fluid and the plug-fluid was aqueous, it was found that this system can be operated at values of C.n. up to ~0.1 (at 300 mm s$^{-1}$). In this system, as the value of the C.n. increased above 0.2, the formation of plugs became irregular. The viscosity of perfluorodecaline is $5.10 \times 10^{-3}$ kg m$^{-3}$s$^{-1}$, the surface tension at the interface between the plugs and the carrier-fluid was $13 \times 10^{-3}$ Nm$^{-1}$.

The length of the plugs can be controlled such that their sizes can range from, for example, about 1 to 4 times a cross-sectional dimension (d, where d is a channel cross-sectional dimension) of a channel using techniques such as varying the ratio of the plug-fluids and carrier-fluids or varying the relative volumetric flow rates of the plug-fluid and carrier-fluid streams. Short plugs tend to form when the flow rate of the aqueous stream is lower than that of a carrier-fluid stream. Long plugs tend to form when the flow rate of the plug-fluid stream is higher than that of the carrier stream.

In one approximation, the volume of a plug is taken equal to about $2 \times d^3$, where d is a cross-sectional dimension of a channel. Thus, the plugs can be formed in channels having cross-sectional areas of, for example, from $20 \times 20$ to $200 \times 200$ $\mu m^2$, which correspond to plug volumes of between about 16 picoliters (pL) to 16 nanoliters (nL). The size of channels may be increased to about 500 $\mu m$ (corresponding to a volume of about 250 nL) or more. The channel size can be reduced to, for example, about 1 $\mu m$ (corresponding to a volume of about 1 femtoliter). Larger plugs are particularly useful for certain applications such as protein crystallizations, while the smaller plugs are particularly useful in applications such as ultrafast kinetic measurements.

In one preferred embodiment, plugs conform to the size and shape of the channels while maintaining their respective volumes. Thus, as plugs move from a wider channel to a narrower channel they preferably become longer and thinner, and vice versa.

Plug-fluids may comprise a solvent and optionally, a reactant. Suitable solvents for use in the invention, such as those used in plug-fluids, include organic solvents, aqueous solvents, oils, or mixtures of the same or different types of solvents, e.g. methanol and ethanol, or methanol and water. The solvents according to the invention include polar and non-polar solvents, including those of intermediate polarity relative to polar and non-polar solvents. In a preferred embodiment, the solvent may be an aqueous buffer solution, such as ultrapure water (e.g., 18 M$\Omega$ resistivity, obtained, for example, by column chromatography), 10 mM Tris HCl, and 1 mM EDTA (TE) buffer, phosphate buffer saline or acetate buffer. Other solvents that are compatible with the reagents may also be used.

Suitable reactants for use in the invention include synthetic small molecules, biological molecules (i.e., proteins, DNA, RNA, carbohydrates, sugars, etc.), metals and metal ions, and the like.

The concentration of reagents in a plug can be varied. In one embodiment according to the invention, the reagent concentration may be adjusted to be dilute enough that most of the plugs contain no more than a single molecule or particle, with only a small statistical chance that a plug will contain two or more molecules or particles. In other embodiments, the reagent concentration in the plug-fluid is adjusted to concentrate enough that the amount of reaction product can be maximized.

Suitable carrier-fluids include oils, preferably fluorinated oils. Examples include viscous fluids, such as perfluorodecaline or perfluoroperhydrophenanthrene; nonviscous fluids such as perfluorohexane; and mixtures thereof (which are particularly useful for matching viscosities of the carrier-fluids and plug-fluids). Commercially available fluorinated compounds such as Fluorinert™ liquids (3M, St. Paul, Minn.) can also be used.

The carrier-fluid or plug-fluid, or both may contain additives, such as agents that reduce surface tensions (e.g., surfactants). Other agents that are soluble in a carrier-fluid relative to a plug-fluid can also be used when the presence of a surfactant in the plug fluid is not desirable. Surfactants may be used to facilitate the control and optimization of plug size, flow and uniformity. For example, surfactants can be used to reduce the shear force needed to extrude or inject plugs into an intersecting channel. Surfactants may affect plug volume or periodicity, or the rate or frequency at which plugs break off into an intersecting channel. In addition, surfactants can be used to control the wetting of the channel walls by fluids. In one embodiment according to the invention, at least one of the plug-fluids comprises at least one surfactant.

Preferred surfactants that may be used include, but are not limited to, surfactants such as those that are compatible with the carrier and plug-fluids. Exemplary surfactants include Tween™, Span™, and fluorinated surfactants (such as Zonyl™ (Dupont, Wilmington Del.)). For example, fluorinated surfactants, such as those with a hydrophilic head group, are preferred when the carrier-fluid is a fluorinated fluid and the plug-fluid is an aqueous solution.

However, some surfactants may be less preferable in certain applications. For instance, in those cases where aqueous plugs are used as microreactors for chemical reactions (including biochemical reactions) or are used to analyze and/or sort biomaterials, a water soluble surfactant such as SDS may denature or inactivate the contents of the plug.

The carrier-fluid preferably wets the walls of the channels preferentially over the plugs. If this condition is satisfied, the plug typically does not come in contact with the walls of the channels, and instead remains separated from the walls by a thin layer of the carrier-fluid. Under this condition, the plugs remain stable and do not leave behind any residue as they are transported through the channels. The carrier-fluid's preferential wetting of the channel walls over the plug-fluid is achieved preferably by setting the surface tension by, for example, a suitable choice of surfactant. Preferably, the surface tension at a plug fluid/channel wall interface (e.g., about 38 mN/m surface tension for a water/PDMS interface) is set higher than the surface tension at a plug fluid/carrier-fluid interface (e.g., about 13 mN/m for a water/carrier-fluid interface with a surfactant such as 10% 1H,1H,2H,2H-perfluorooctanol in perfluorodecaline as the carrier-fluid). If this condition is not satisfied, plugs tend to adhere to the channel walls and do not undergo smooth transport (e.g., in the absence of 1H,1H,2H,2H-perfluorooctanol the surface tension at the water/perfluorodecaline interface is about 55 mN/m, which is higher than the surface tension of the water/PDMS interface (e.g., about 38 mN/m)), and plugs adhere to the walls of the PDMS channels. Because the walls of the channels (PDMS, not fluorinated) and the carrier-fluid (fluorinated oil) are substantially different chemically, when a fluorinated surfactant is introduced, the surfactant reduces the surface tension at the oil-water interface preferentially over the wall-water interface. This allows the formation of plugs that do not stick to the channel walls.

The surface tension at an interface may be measured using what is known as a hanging drop method, although one may also use other methods. Preferably, the surface tension is sufficiently high to avoid destruction of the plugs by shear.

The plug-fluids and carrier-fluids may be introduced through one or more inlets. Specifically, fluids may be introduced into the substrate through pneumatically driven syringe reservoirs that contain either the plug-fluid or carrier-fluid. Plugs may be produced in the carrier-fluid stream by modifying the relative pressures such that the plug-fluids contact the carrier-fluid in the plug-forming regions then shear off into discrete plugs.

In the invention, plugs are formed by introducing the plug-fluid, at the plug-forming region, into the flow of carrier-fluid passing through the first channel. The force and direction of flow can be controlled by any desired method for controlling flow, for example, by a pressure differential, or by valve action. This permits the movement of the plugs into one or more desired branch channels or outlet ports.

In preferred embodiments according to the invention, one or more plugs are detected, analyzed, characterized, or sorted dynamically in a flow stream of microscopic dimensions based on the detection or measurement of a physical or chemical characteristic, marker, property, or tag.

The flow stream in the first channel is typically, but not necessarily continuous and may be stopped and started, reversed or changed in speed. Prior to sorting, a non-plug-fluid can be introduced into a sample inlet port (such as an inlet well or channel) and directed through the plug-forming region, e.g., by capillary action, to hydrate and prepare the device for use. Likewise, buffer or oil can also be introduced into a main inlet port that communicates directly with the first channel to purge the substrate (e.g., of "dead" air) and prepare it for use. If desired, the pressure can be adjusted or equalized, for example, by adding buffer or oil to an outlet port.

The pressure at the plug-forming region can also be regulated by adjusting the pressure on the main and sample inlets, for example with pressurized syringes feeding into those inlets. By controlling the difference between the oil and water flow rates at the plug-forming region, the size and periodicity of the plugs generated may be regulated. Alternatively, a valve may be placed at or coincident to either the plug-forming region or the sample inlet connected thereto to control the flow of solution into the plug-forming region, thereby controlling the size and periodicity of the plugs. Periodicity and plug volume may also depend on channel diameter and/or the viscosity of the fluids.

Mixing in Plugs

FIG. 7 (a)-(b) show microphotographs (10 µs exposure) illustrating rapid mixing inside plugs (a) and negligible mixing in a laminar flow (b) moving through winding channels at the same total flow velocity. Aqueous streams were introduced into inlets 700-705 in FIGS. 7(a)-(b). In FIGS. 7(c) and 7(e), Fluo-4 was introduced into inlets 706, 709, buffer was introduced into inlets 707, 710, and $CaCl_2$ was introduced into inlets 708, 711. FIG. 7(c) shows a false-color microphotograph (2 s exposure, individual plugs are invisible) showing time-averaged fluorescence arising from rapid mixing inside plugs of solutions of Fluo-4 (54 µM) and $CaCl_2$ (70 µM) in aqueous sodium morpholine propanesulfonate buffer (20 µM, pH 7.2); this buffer was also used as the middle aqueous stream. FIG. 7(d) shows a plot of the relative normalized intensity (I) of fluorescence obtained from images such as shown in (c) as a function of distance (left) traveled by the plugs and of time required to travel that distance (right) at a given flow rate. The total intensity across the width of the channel was measured. Total PFD/water volumetric flow rates (in µL min$^{-1}$) were 0.6:0.3, 1.0:0.6, 12.3:3.7, 10:6, and 20:6. FIG. 7(e) shows a false-color microphotograph (2 s exposure) of the weak fluorescence arising from negligible mixing in a laminar flow of the solutions used in (c). All channels were 45 µm deep; inlet channels were 50 µm and winding channels 28 µm wide; Re~5.3 (water), ~2.0 (PFD).

FIG. 8 shows photographs and schematics that illustrate fast mixing at flow rates of about 0.5 µL/min (top schematic diagram and photograph) and about 1.0 µL/min (lower schematic diagram and photograph) using 90°-step channels while FIG. 9 illustrates fast mixing at flow rates of about 1.0 µL/min (top schematic diagram and photograph) and about 0.5 µL/min (lower schematic diagram and photograph) using 135°-step channels. Aqueous streams are introduced into inlets 800-805 in FIG. 8 (inlets 900-905 in FIG. 9), while a carrier fluid is introduced into channels 806, 807 (channels 906, 907 in FIG. 9). The plugs that form then flow through exits 808, 809 (FIG. 8) and exits 908, 909 (FIG. 9). As can be seen in FIG. 8 and FIG. 9, the plugs are transported along multi-step channels, instead of channels with smooth curves (as opposed to channels with sharp corners). An advantage of these multi-step configurations of channels is that they may provide further enhanced mixing of the substances within the plugs.

Several approaches may be used to accelerate or improve mixing. These approaches may then be used to design channel geometries that allow control of mixing. Flow can be controlled by perturbing the flow inside a moving plug so that it differs from the symmetric flow inside a plug that moves through a straight channel. For example, flow perturbation can be accomplished by varying the geometry of a channel (e.g., by using winding channels), varying the composition of the plug fluid (e.g., varying the viscosities), varying the composition of the carrier-fluid (e.g., using several laminar streams of carrier-fluids that are different in viscosity or surface tension to form plugs; in this case, mixing is typically affected, and in some cases enhanced), and varying the patterns on the channel walls (e.g., hydrophilic and hydrophobic, or differentially charged, patches would interact with moving plugs and induce time-periodic flow inside them, which should enhance mixing).

Figures 1, 1C:
Figures 1, 1C, 2:
Figures 1, 1C, 2, 3:
Figures 1, 1C, 2, 3, 4:

Various channel designs can be implemented to enhance mixing in plugs. FIG. 1A shows a schematic of a basic channel design, while FIG. 1B shows a series of periodic variations of the basic channel design. FIG. 1C shows a series of aperiodic combinations resulting from a sequence of alternating elements taken from a basic design element shown in FIG. 1A and an element from the periodic variation series shown in FIGS. 1B(1)-(4). When the effects of these periodic variations are visualized, aperiodic combinations of these periodic variations are preferably used to break the symmetries arising from periodic flows (see FIG. 1C). Here, the relevant parameters are channel width, period, radius of curvature, and sequence of turns based on the direction of the turns. The parameters of the basic design are defined such that c is the channel width, l is the period, and r is the radius of curvature. For the basic design, the sequence can be defined as (left, right, left, right), where left and right is relative to a centerline along the path taken by a plug in the channel.

FIGS. 1B(1)-4) show schematic diagrams of a series of periodic variations of the basic design. At least one variable parameter is preferably defined based on the parameters defined in FIG. 1a). In FIG. 1B(1), the channel width is c/2; in FIG. 1B(2), the period is 2 l; and in FIG. 1B(3), and the radius of curvature is 2r. In FIG. 1B(4), the radius of curvature is r/2 and the sequence is (left, left, right, right).

FIGS. 1C(1)-(4) show a schematic diagram of a series of aperiodic combinations formed by combining the basic design element shown in FIG. 1A with an element from the series of periodic variations in FIG. 1B(1)-(4). In FIG. 1C(1), the alternating pattern of a period of the basic design shown in FIG. 1A (here denoted as "a") and a period of the channel in FIG. 1B(1) (here denoted as "b1") is given by a+b1+a+ . . . In FIG. 1C(2), the aperiodic combination is given by a+b2+a. In the channel shown in FIG. 1C(3) (here denoted as "c3"), the aperiodic combination is given by a+c3+a. In the channel shown in FIG. 1C(4) (here denoted as "c4"), a (right, left) sequence is introduced with a kink in the pattern. A repeating (left, right) sequence would normally be observed. By adding this kink, the sequence becomes (left, right, left, right)+(right, left)+(left, right, left, right).

Another approach for accelerating mixing relies on rationally-designed chaotic flows on a microfluidic chip using what is known as the baker's transformation. Reorientation of the fluid is critical for achieving rapid mixing using the baker's transformation. The baker's transformation leads to an exponential decrease of the striation thickness (the distance over which mixing would have to occur by diffusion) of the two components via a sequence of stretching and folding operations. Typically, every stretch-fold pair reduces the striation thickness by a factor of 2, although this factor may have a different value. The striation thickness (ST) can be represented, in an ideal case, by Eqn. (2) below. Thus, in the ideal case, in a sequence of n stretch-fold-reorient operations, the striation thickness undergoes an exponential decrease given by $$ST(t_n)=ST(t_0)\times 2^{-n} \qquad \text{Eqn. (2)}$$

where $ST(t_n)$ represents the striation thickness at time $t_n$, $ST(t_0)$ represents the initial striation thickness at time $t_0$, and n is the number of stretch-fold-reorient operations.

In accordance with the invention, the baker's transformation is preferably implemented by creating channels composed of a sequence of straight regions and sharp turns. FIG. 11 shows a schematic diagram of a channel geometry designed to implement and visualize the baker's transformation of plugs flowing through microfluidic channels. Other designs could also be used. The angles at the channel bends and the lengths of the straight portions are chosen so as to obtain optimal mixing corresponding to the flow patterns shown. Different lengths of straight paths and different turns may be used depending on the particular application or reaction involved.

A plug traveling through every pair of straight part 112 and sharp-turn part 111 of the channel, which is equivalent to one period of a baker's transformation, will experience a series of reorientation, stretching and folding. In a straight part of the channel, a plug will experience the usual recirculating flow. At a sharp turn, a plug normally rolls and reorients due to the much higher pressure gradient across the sharp internal corner and also due to larger travel path along the outside wall. This method of mixing based on the baker's transformation is very efficient and is thus one of the preferred types of mixing. In particular, this type of mixing leads to a rapid reduction of the time required for reagent mixing via diffusion.

It is believed that plug formation can be maintained at about the same flow rate in channels of different sizes because the limit of a flow rate is typically set by the capillary number, C.n., which is independent of the channel size. At a fixed flow rate, the mixing time $t_{mix}$ may decrease as the size of the channel (d) is reduced. First, it is assumed that it takes the same number n of stretch-fold-reorient cycles to mix reagents in both large and small channels. This assumption (e.g., for n~5) is in approximate agreement with previously measured mixing in d=55 and d=20 micrometer (µm) channels. Each cycle requires a plug to travel over a distance of approximately 2 lengths of the plug (approximately 3d). Therefore, mixing time is expected to be approximately equal to the time it takes to travel 15d, and will decrease linearly with the size of the channel, $t_{mix}$~d. A method that provides mixing in about 1 ms in 25-µm channels preferably provides mixing in about 40 µs in 1-µm channels. Achieving microsecond mixing times generally requires the use of small channels. High pressures are normally required to drive a flow through small channels.

Without wishing to be bound by theory, theoretical modeling indicates that the number of cycles it takes for mixing to occur in a channel with diameter d is given approximately by $$n \times 2^{2n} \approx dU/D \qquad \text{Eqn. (3)}$$

where n is the number of cycles, U is the flow velocity, D is the diffusion constant, one cycle is assumed to be equal to 6d, and mixing occurs when convection and diffusion time scales are matched. The mixing time is primarily determined by the number of cycles. This result indicates that mixing will be accelerated more than just in direct proportion to the channel diameter. For example, when d decreases by a factor of 10, mixing time decreases by a factor of d×Log(d)=10× Log(10). With properly designed channels, mixing times in 1-µm channels can be limited to about 20 µs. Even at low flow rates or long channels (such as those involving protein crystallization), however, significant mixing can still occur. In addition, without being bound by theory, it is expected that increasing the flow rate U by a factor of 10 will decrease the mixing time by a factor of Log(U)/U=(Log (10))/10.

To visualize mixing in a channel according to the invention, a colored marker can be used in a single plug-fluid. The initial distribution of the marker in the plug has been observed to depend strongly on the details of plug formation. As the stationary aqueous plug was extruded into the flowing carrier-fluid, shearing interactions between the flow of the carrier-fluid and the plug-fluid induced an eddy that redistributed the solution of the marker to different regions of the plug. The formation of this eddy is referred to here as "twirling" (see FIG. 27b)). Twirling is not a high Reynolds number (Re) phenomenon (see FIG. 30) since it was observed at substantially all values of Re and at substantially all velocities. However, the flow pattern of this eddy appears to be slightly affected by the velocity.

Various characteristics and behavior of twirling were observed. Twirling redistributed the marker by transferring it from one side of the plug to the other, e.g., from the right to the left side of the plug. The most efficient mixing was observed when there was minimal fluctuations in intensity, i.e., when the marker was evenly distributed across the plug. While twirling was present during the formation of plugs of all lengths that were investigated, its significance to the mixing process appears to depend on the length of the plug. For example, the extent of twirling was observed to be significantly greater for short plugs than for long plugs. Twirling was also observed to affect only a small fraction of the long plugs and had a small effect on the distribution of the marker in the plugs. Moreover, twirling occurred only at the tip of the forming plug before the tip made contact with the right wall of the microchannel. Also, the amount of twirling in a plug was observed to be related to the amount of the carrier-fluid that flowed past the tip. The results of experiments involving twirling and its effect on mixing show that twirling is one of the most important factors, if not the most important factor, in determining the ideal conditions for mixing occurring within plugs moving through straight channels. By inducing twirling, one may stimulate mixing; by preventing twirling, one may suppress complete mixing. Suppressing mixing may be important in some of the reaction schemes, for example those shown in FIG. 5 and FIG. 6. In these reaction schemes, selective mixing of reagents A with reagent B, and also reagent C with reagent D, can occur without mixing of all four reagents. Mixing of all four reagents occurs later as plugs move through, for example, the winding part of the channel. This approach allows several reactions to occur separated in time. In addition, suppressing mixing may be important when interfaces between plug fluids have to be created, for example interfaces required for some methods of protein crystallization (FIG. 20).

The eddy at the tip of a developing plug may complicate visualization and analysis of mixing. This eddy is normally significant in short plugs, but only has a minor effect on long plugs. For applications involving visualization of mixing, the substrate is designed to include a narrow channel in the plug-forming region is designed such that narrow, elongated plugs form. Immediately downstream from the plug-forming region, the channel dimension is preferably expanded. In the expanded region of the channel(s), plugs will expand and become short and rounded under the force of surface tension; this preserves the distribution of the marker inside the plugs. This approach affords a relatively straightforward way of visualizing the mixing inside plugs of various sizes. Video microscopy may be used to observe the distribution of colored markers inside the drops. A confocal microscope may also be used to visualize the average three-dimensional distribution of a fluorescent marker. Visualization can be complemented or confirmed using a $Ca^{2+}/Fluo-4^{-4}$ reaction. At millimolar concentrations, this reaction is expected to occur with a half-life of about 1 µs. Thus, it can be used to measure mixing that occurs on time scales of about 10 µs and longer.

The following discussion describes at least one method for three-dimensional visualization of flows in plugs. Visualization of chaotic transport in three-dimensions is a challenging task especially on a small scale. Predictions based on two-dimensional systems may be used to gain insight about plugs moving through a three-dimensional microfluidic channel. Experiments and simulations involving a two-dimensional system can aid in the design of channels that ensure chaotic flow in two-dimensional liquid plugs. Confocal microscopy has been used to quantify steady, continuous three-dimensional flows in channels. However, due to instrumental limitations of an optical apparatus such as a confocal microscope, it is possible that the flow cannot be visualized with sufficiently high-resolution to observe, for example, self-similar fractal structures characteristic of chaotic flow. Nonetheless, the overall dynamics of the flow may still be captured and the absence of non-chaotic islands confirmed. Preferably, the channels (periodic or aperiodic) used in the visualization process are fabricated using soft lithography in PDMS. A PDMS replica is preferably sealed using a thin glass cover slip to observe the flow using confocal microscopy.

In one experiment according to the invention, a series of line scans are used to obtain images of a three-dimensional distribution of fluorescent markers within the plugs. FIG. 10a) is a schematic diagram depicting a three-dimensional confocal visualization of chaotic flows in plugs. Plugs are preferably formed from three laminar streams. The middle stream 11 preferably contains fluorescent markers. Preferably, the middle stream 11 is injected into the channel system at a low volumetric flow rate. The volumetric flow rates of the two side streams 10, 12 are preferably adjusted to position the marker stream in a desired section of the channel. Preferably, a confocal microscope such as a Carl Zeiss LSM 510 is used. The LSM 510 is capable of line scans at about 0.38 ms/512 pixel line or approximately 0.2 ms/100 pixel line. Fluorescent microspheres, preferably about 0.2 µm, and fluorescently labeled high-molecular weight polymers are preferably used to visualize the flow with minimal interference from diffusion. A channel such as one with 100 µm wide and 100 µm deep channel may be used. The line scan technique may be applied to various sequences such as one that has about 200-µm long plugs separated by about 800-µm long oil stream.

A beam is preferably fixed in the x and z-directions and scanned repeatedly back and forth along the y-direction. The movement of the plug in the x-direction preferably provides resolution along the x-direction. Line scan with 100 pixels across a 100 µm-wide channel will provide a resolution of about 1 µm/pixel in the y-direction. Approximately 200 line scans per plug are preferably used to give a resolution of about 1 µm/pixel in the x-direction. For a 200 µm plug moving at about 2000 µm/s, about 200 line scans are preferably obtained over a period of about (200 µm)/(2000 µm/s)=0.1 s, or about 0.5 ms per line.

The sequence shown in FIG. 10b) is preferably used for visualization of a three dimensional chaotic flow. Each line scan preferably takes about 0.2 ms with about 0.3 ms lag between the scans to allow the plug to move by about 500 µm. Some optical distortions may result during the approximately 0.2 ms scan as the plug is translated along the x-direction by about 0.2 µm. However, these distortions are believed to be comparable to the resolution of the method. For a given position along the x-direction, a series of line scans are preferably obtained for about 10 seconds for each point along the z-direction to obtain an x-y cross-sections of ten plugs. Scans along the z-direction are preferably taken in 1 µm increments to obtain a full three-dimensional image of the distribution of the fluorescent marker in the plug. This procedure is preferably repeated at different positions along the x-direction to provide information such as changes in the three-dimensional distribution of the fluorescent marker inside the plug as the plug moves along the channels.

In case of periodic perturbations, the fluorescent cross-sections of the plug in the y-z plane recovered from the above procedure represent Poincaré sections corresponding to the evolution of the initial thin sheet of dye. The twirling of the aqueous phase upon formation of the small plugs could distribute the dye excessively throughout the plug and could make visualization less conclusive. This twirling is prevented preferably by designing a small neck in the plug-forming region, and then beginning the first turn in a downward direction. This approach has been successfully applied to flow visualization, and may be useful for conducting reactions.

Merging Plugs

The invention also provides a method of merging of plugs within a substrate (see upper portion of FIG. 12). Plugs are formed as described above. Plugs containing different reagents can be formed by separately introducing different plug-fluids into a channel. The plugs containing different reagents may be substantially similar in viscosity or may differ. The plugs containing different reagents may be substantially similar in size or they may differ in size. Provided that the relative velocities of the plugs containing different reagents differ, the plugs will merge in the channels. The location of merging can be controlled in a variety of ways, for example by varying the location of plug-fluid inlet ports, by varying the location of channel junctions (if one of the plug forming fluids is introduced into a secondary channel), varying the size of the plugs, adjusting the speed at which different sets of plugs are transported varying the viscosity or surface tension of plugs having substantially the same size, etc.

As shown in FIG. 12 (top photograph), plugs may be merged by directing or allowing the plugs 120, 121 to pass through a T-shaped channel or a T-shaped region of a channel. The resulting merged plugs 122 flow in separate channels or channel branches which may be perpendicular, as shown in FIG. 12, or nonperpendicular (FIG. 33). The merged plugs 122 may undergo further merging or undergo splitting, or they may be directed to other channels, channel branches, area, or region of the substrate where they may undergo one or more reactions or "treatments" such as one or more types of characterizations, measurements, detection, sorting, or analysis.

In one embodiment, large and small plugs flow along separate channels or channel branches towards a common channel where they merge. In a case where a large and a small plug do not converge at the same point at the same time, they eventually form a merged plug as the larger plug, which moves faster than the smaller plug, catches up with the small plug and merges with it. In the case where the larger and smaller plugs meet head on at the same point or region, they immediately combine to form a merged plug. The merged plugs may undergo splitting, described below, or further merging in other channels or channel regions, or they may be directed to other channels, channel branches, area, or region of the substrate where they may undergo one or more types of characterizations, measurements, detection, sorting, or analysis.

In another embodiment, plugs can be merged by controlling the arrival time of the plugs flowing in opposite directions towards a common point, area, or region of the channel so that each pair of plugs arrive at the common point, area, or region of the channel at around the same time to form a single plug.

In another embodiment, an arched, semi-circular, or circular channel provides a means for increasing the efficiency of plug merging. Thus, for example, a greater frequency of merging would occur within a more compact area or region of the substrate. Using this scheme, plugs flowing along separate channels towards a common channel may merge within a shorter distance or a shorter period of time because the arched, semi-circular, or circular channel or channel branch converts or assists in converting initially out-of-phase plug pairs to in-phase plug pairs. Specifically, the arched, semi-circular, or circular channel or channel branch would allow a lagging plug to catch up and merge with a plug ahead of it, thereby increasing the number of merged plugs in a given period or a given area or region of a substrate.

Splitting and/or Sorting Plugs

The present invention also provides a method for splitting of plugs within a substrate. Plugs can be split by passing a first portion of a plug into a second channel through an opening, wherein the second channel is downstream of where the plug is formed. Alternatively, plugs may be split at a "Y" intersection in a channel. In both embodiment, the initial plug splits into a first portion and a second portion and thereafter each portion passes into separate channel (or outlet). Either initially formed plugs can be split or, alternatively, merged plugs can be split. FIG. 6 shows a schematic diagram illustrating part of a microfluidic network that uses multiple inlets (inlets 601, 603, 605, 607 for reagents A, B, C, and D; inlets 602, 604, 606 for aqueous streams) and that allows for both splitting and merging of plugs. This schematic diagram shows two reactions that are conducted simultaneously. A third reaction (between the first two reaction mixtures) is conducted using precise time delay. Plugs can be split before or after a reaction has occurred. In addition, FIG. 6 shows plugs at various stages of mixing from the initial mixture 60 (A+B) and initial mixture 61 (C+D) through the mixed solutions 62 (A+B), 63 (C+D), and the 4-component mixture 64 (A+B+C+D).

As shown in FIG. 12 (lower photograph), plugs may be split by directing or allowing the plugs 123, 124 to pass through a T-shaped channel or a T-shaped region of a channel. In a preferred embodiment, the area or junction at which the plugs undergo splitting may be narrower or somewhat constricted relative to the diameter of the plugs a certain distance away from the junction. The resulting split plugs 125 flow in separate channels or channel branches which may be perpendicular, as shown in FIG. 12, or nonperpendicular (FIG. 33). The split 125 plugs may undergo merging or further splitting, or they may be directed to other channels, channel branches, area, or region of the substrate where they may undergo one or more reactions or "treatments" such as one or more types of characterizations, measurements, detection, sorting, or analysis.

In another embodiment, aqueous plugs can be split or sorted from an oil carrier fluid by using divergent hydrophilic and hydrophobic channels. The channels are rendered hydrophilic or hydrophobic by pretreating a channel or region of a channel such that a channel or channel surface becomes predominantly hydrophilic or hydrophobic. As discussed in more detail below, substrates with hydrophilic channel surfaces may be fabricated using methods such as rapid prototyping in polydimethylsiloxane. The channel surface can be rendered hydrophobic either by silanization or heat treatment. For example, (tridecafluoro-1,1,2,2-tetrahydrooctyl)-1-trichloro silane (United Chemical Technologies, Inc.) vapor may be applied to the inlets of the substrate with dry nitrogen as a carrier gas to silanize the channel surface.

Once plugs have been split into separate channels, further reactions can be performed by merging the split plugs with other plugs containing further reactants.

Manipulation of plugs and reagents/products contained therein can also be accomplished in a fluid flow using methods or techniques such as dielectrophoresis. Dielectrophoresis is believed to produce movement of dielectric objects, which have no net charge, but have regions that are positively or negatively charged in relation to each other. Alternating, nonhomogeneous electric fields in the presence of plugs and/or particles, cause the plugs and/or particles to become electrically polarized and thus to experience dielectrophoretic forces. Depending on the dielectric polarizability of the particles and the suspending medium, dielectric particles will move either toward the regions of high field strength or low field strength. Using conventional semiconductor technologies, electrodes can be fabricated onto a substrate to control the force fields in a micro fabricated device. Dielectrophoresis is particularly suitable for moving objects that are electrical conductors. The use of AC current is preferred, to prevent permanent alignment of ions. Megahertz frequencies are suitable to provide a net alignment, attractive force, and motion over relatively long distances.

Radiation pressure can also be used in the invention to deflect and move plugs and reagents/products contained therein with focused beams of light such as lasers. Flow can also be obtained and controlled by providing a thermal or pressure differential or gradient between one or more channels of a substrate or in a method according to the invention.

Preferably, both the fluid comprising the plugs and the carrier fluid have a relatively low Reynolds Number, for example $10^{-2}$. The Reynolds Number represents an inverse relationship between the density and velocity of a fluid and its viscosity in a channel of given cross-sectional dimension. More viscous, less dense, slower moving fluids will have a lower Reynolds Number, and are easier to divert, stop, start, or reverse without turbulence. Because of the small sizes and slow velocities, fabricated fluid systems are often in a low Reynolds number regime ($R_e \ll 1$). In this regime, inertial effects, which cause turbulence and secondary flows, are negligible and viscous effects dominate the dynamics. These conditions are advantageous for analysis, and are provided by devices according to the invention. Accordingly the devices according to the invention are preferably operated at a Reynolds number of less than 100, typically less than 50, preferably less than 10, more preferably less than 5, most preferably less than 1.

Detection and Measurement

The systems of the present invention are well suited for performing optical measurements using an apparatus such as a standard microscope. For example, PDMS is transparent in the visible region. When it is used to construct a substrate, a glass or quartz cover slip can be used to cover or seal a PDMS network, thereby constructing a set of channels that can be characterized using visible, UV, or infrared light. Preferably, fluorescent measurements are performed, instead of absorption measurements, since the former has a higher sensitivity than the latter. When the plugs are being monitored by optical measurements, the refractive index of the carrier-fluid and the plug-fluids are preferably substantially similar, but they can be different in certain cases.

In a plug-based system according to the invention, the relative concentrations (or changes in concentrations) can be typically measured in a straightforward fashion. In some instances, the use of plugs to perform quantitative optical measurements of, for example, absolute concentrations is complicated by the presence of non-horizontal oil/water interfaces surrounding the plugs. These curved interfaces act as lenses, and may lead to losses of emitted light or optical distortions. Such distortions may adversely affect or prevent visual observation of growing protein crystals, for example. Exact modeling of these losses is usually difficult because of the complicated shape that this interface may adopt at the front and back of a plug moving in a non-trivial pressure gradient.

This problem can be overcome or minimized in accordance with the invention by using a technique such as refractive index matching. The losses and distortions depend on the difference between the refractive index ($\eta_D$) of the aqueous phase and the refractive index of the immiscible carrier-fluid. Preferably, the carrier-fluid used in an analysis have refractive indices that are substantially similar to those of water and aqueous buffers (TABLE 1), e.g., fluorinated oils having refractive indices near that of water close to the sodium D line at 589 nm.

Preferably, for applications involving detection or measurement, the carrier-fluids used are those having refractive indices that match those of commonly used aqueous solutions at the wavelengths used for observation. To calibrate a system for quantitative fluorescence measurements, the plugs preferably contain known concentrations of fluorescein. Preferably, the fluorescence originating from the plugs are measured and then compared with the fluorescence arising from the same solution of fluorescein in the channel in the absence of oil. It is believed that when the refractive indexes are matched, the intensity (I) of fluorescence arising from the plugs will be substantially similar or equal to the intensity of the fluorescence from the aqueous solutions after making adjustments for the fraction of the aqueous stream:

$$I_{plug}=I_{solution}*V_{water}/(V_{water}+V_{oil})$$ Eqn. (3)

where V is the volumetric flow rate of the fluid streams. It is expected that smaller plugs with a higher proportion of curved interfaces will show larger deviations from ideal plug behavior, i.e., those smaller plugs will tend to cause greater optical distortion. If necessary, measurements are performed partly to determine the errors associated with refractive index mismatch. Information from these measurements is useful when unknown fluids are analyzed, or when a compromise between matching the refractive index and matching the viscosities of the two fluids is required.

TABLE 1

Physical properties of some fluids used in certain embodiments of the microfluidic devices.

| Fluid | Refractive index, $\eta D$ | Viscosity, $\mu$ [mPa-s] |
| --- | --- | --- |
| water | 1.3330 | 1.00 |
| aqueous PBS buffer, 1% | 1.3343 | 1.02 |
| aqueous PBS buffer, 10% | 1.3460 | 1.25 |
| perfluorohexane | 1.251 | 0.66 |
| perfluoro(methylcyclohexane) | 1.30 | 1.56 |
| perfluoro(1,3-dimethylcyclohexane) | 1.2895 | 1.92 |
| perfluorodecaline | 1.314 | 5.10 |
| perfluoroperhydrofluorene | 1.3289 | 9.58 |
| perfluoroperhydrophenanthrene | 1.3348 | 28.4 |
| perfluorotoluene | 1.3680 | N/A |
| hexafluorobenzene | 1.3770 | N/A |

The detector can be any device or method for evaluating a physical characteristic of a fluid as it passes through the detection region. Examples of suitable detectors include CCD detectors. A preferred detector is an optical detector, such as a microscope, which may be coupled with a computer and/or other image processing or enhancement devices to process images or information produced by the microscope using known techniques. For example, molecules can be analyzed and/or sorted by size or molecular weight. Reactions can be monitored by measuring the concentration of a product produced or the concentration of a reactant remaining at a given time. Enzymes can be analyzed and/or sorted by the extent to which they catalyze a chemical reaction of an enzyme's substrate (conversely, an enzyme's substrate can be analyzed (e.g., sorted) based on the level of chemical reactivity catalyzed by an enzyme). Biological particles or molecules such as cells and virions can be sorted according to whether they contain or produce a particular protein, by using an optical detector to examine each cell or virion for an optical indication of the presence or amount of that protein. A chemical itself may be detectable, for example by a characteristic fluorescence, or it may be labeled or associated with a tag that produces a detectable signal when, for example, a desired protein is present, or is present in at least a threshold amount.

Practically any characteristic of a chemical can be identified or measured using the techniques according to the invention, provided that the characteristic or characteristics of interest for analysis can be sufficiently identified and detected or measured to distinguish chemicals having the desired characteristic(s) from those which do not. For example, particulate size, hydrophobicity of the reagent versus carrier-fluids, etc. can be used as a basis for analyzing (e.g., by sorting) plug-fluids, reaction products or plugs.

In a preferred embodiment, the plugs are analyzed based on the intensity of a signal from an optically detectable group, moiety, or compound (referred to here as "tag") associated with them as they pass through a detection window or detection region in the device. Plugs having an amount or level of the tag at a selected threshold or within a selected range can be directed into a predetermined outlet or branch channel of the substrate. The tag signal may be collected by a microscope and measured by a detector such as a photomultiplier tube (PMT). A computer is preferably used to digitize the PMT signal and to control the flow through methods such as those based on valve action. Alternatively, the signal can be recorded or quantified as a measure of the tag and/or its corresponding characteristic or marker, e.g., for the purpose of evaluation and without necessarily proceeding to, for example, sort the plugs.

In one embodiment according to the invention, a detector such as a photodiode is larger in diameter than the width of the channel, forming a detection region that is longer (along the length of channel) than it is wide. The volume of such a detection region is approximately equal to the cross sectional area of the channel above the diode multiplied by the diameter of the diode.

To detect a chemical or tag, or to determine whether a chemical or tag has a desired characteristic, the detection region may include an apparatus (e.g., a light source such as a laser, laser diode, high intensity lamp such as mercury lamp) for stimulating a chemical or tag for that characteristic to, for example, emit measurable light energy. In embodiments where a lamp is used, the channels are preferably shielded from light in all regions except the detection region. In embodiments where a laser is used, the laser can be set to scan across a set of detection regions. In addition, laser diodes may be fabricated into the same substrate that contains the analysis units. Alternatively, laser diodes may be incorporated into a second substrate (i.e., a laser diode chip) that is placed adjacent to the analysis or sorter substrate such that the laser light from the diodes shines on the detection region(s).

In preferred embodiments, an integrated semiconductor laser and/or an integrated photodiode detector are included on the silicon wafer in the device according to the invention. This design provides the advantages of compactness and a shorter optical path for exciting and/or emitted radiation, thus minimizing, for example, optical distortion.

As each plug passes into the detection region, it may be examined for a characteristic or property, e.g., a corresponding signal produced by the plug, or the chemicals contained in the plugs, may be detected and measured to determine whether or not a given characteristic or property is present. The signal may correspond to a characteristic qualitatively or quantitatively. Typically, the amount of signal corresponds to the degree to which a characteristic is present. For example, the strength of the signal may indicate the size of a molecule, the amount of products(s) formed in a reaction, the amount of reactant(s) remaining, the potency or amount of an enzyme expressed by a cell, a positive or negative reaction such as binding or hybridization of one molecule to another, or a chemical reaction of a substrate catalyzed by an enzyme. In response to the signal, data can be collected and/or a flow control can be activated, for example, to direct a plug from one channel to another. Thus, for example, chemicals present in a plug at a detection region may be sorted into an appropriate branch channel according to a signal produced by the corresponding examination at a detection region. Optical detection of molecular characteristics or the tag associated with a characteristic or property that is chosen for sorting, for example, may be used. However, other detection techniques, for instance electrochemistry, or nuclear magnetic resonance, may also be employed.

In one embodiment according to the invention, a portion of a channel corresponds to an analysis unit or detection region and includes a detector such as a photodiode preferably located in the floor or base of the channel. The detection region preferably encompasses a receive field of the photodiode in the channel, which receive field has a circular shape. The volume of the detection region is preferably the same as, or substantially similar, to the volume of a cylinder with a diameter equal to the receive field of the photodiode and a height equal to the depth of the channel above the photodiode.

The signals from the photodiodes may be transmitted to a processor via one or more lines representing any form of electrical communication (including e.g. wires, conductive lines etched in the substrate, etc.). The processor preferably acts on the signals, for example by processing them into values for comparison with a predetermined set of values for analyzing the chemicals. In one embodiment, a value corresponds to an amount (e.g., intensity) of optically detectable signal emitted from a chemical which is indicative of a particular type or characteristic of a chemical giving rise to the signal. The processor preferably uses this information (i.e., the values) to control active elements in a discrimination region, for example to determine how to sort the chemicals (e.g., valve action).

When more than one detection region is used, detectors such as photodiodes in a laser diode substrate are preferably spaced apart relative to the spacing of the detection regions in the analysis unit. That is, for more accurate detection, the detectors are placed apart at the same spacing as the spacing of the detection region.

A processor can be integrated into the same substrate that contains at least one analysis unit, or it can be separate, e.g., an independent microchip connected to the analysis unit containing substrate via electronic leads that connect to the detection region(s) and/or to the discrimination region(s), such as by a photodiode. The processor can be a computer or microprocessor, and is typically connected to a data storage unit, such as computer memory, hard disk, or the like, and/or a data output unit, such as a display monitor, printer and/or plotter.

The types and numbers of chemicals based on the detection of, for example, a tag associated with or bound to the chemical passing through the detection region, can be calculated or determined, and the data obtained can be stored in the data storage unit. This information can then be further processed or routed to a data outlet unit for presentation, e.g. histograms representing, for example, levels of a protein, saccharide, or some other characteristic of a cell surface in the sample. The data can also be presented in real time as the sample flows through a channel.

If desired, a substrate may contain a plurality of analysis units, i.e., more than one detection region, and a plurality of branch channels that are in fluid communication with and that branch out from the discrimination regions. It will be appreciated that the position and fate of the reagents in the discrimination region can be monitored by additional detection regions installed, for example, immediately upstream of the discrimination region and/or within the branch channels immediately downstream of the branch point. The information obtained by the additional detection regions can be used by a processor to continuously revise estimates of the velocity of the reagents in the channels and to confirm that molecules, particles, and substances having a selected characteristic enter the desired branch channel.

In one embodiment, plugs are detected by running a continuous flow through a channel, taking a spatially resolved image with a CCD camera, and converting the relevant distance traversed by the plugs into time.

In another embodiment, plugs are detected following their exit through a channel point leading to a mass spectrometer (MS), e.g., an electrospray MS. In this embodiment, time-resolved information (e.g., mass spectrum) can be obtained when the flow rate and the distance traversed by the plugs are known. This embodiment is preferable when one wants to avoid using a label.

Varying the Concentration of Reagents Inside Plugs

The various devices and methods according to the invention allow the control and manipulation of plug composition and properties. For example, they allow the variation of reagent concentration inside plugs. In one aspect according to the invention, the concentrations of the reagents in the plugs are varied by changing the relative flow rates of the plug-fluids. This is possible in conventional systems, but is complicated by problems of slow mixing and dispersion. Methods according to the invention are convenient for simultaneously testing a large number of experimental conditions ("screening") because the concentrations can be changed within a single setup. Thus, for example, syringes do not have to be disconnected or reconnected, and the inlets of a system according to the invention do not have to be refilled when using the above technique for varying the reagent concentrations in plugs.

The concentration of aqueous solutions inside plugs can be varied by changing the flow rates of the plug-fluid streams (see FIG. 25, discussed in detail in Example 11). In FIG. 25, water is introduced into inlets 251-258 at various flow rates while perfluorodecaline flows through channels 259-261. In aqueous laminar flows, the ratio of flow rates of laminar streams in a microfluidic channel may be varied from about 1000:1 and 1:1000, preferably 100:1 to 1:100, more preferably 1:20 to 20:1.

The actual relative concentrations may be quantified using a solution of known concentration of fluorescein. In this example, the intensity of a fluorescein stream can be used as a reference point to check for fluctuations of the intensity of the excitation lamp.

To illustrate an advantage offered by the invention over other techniques, consider the following example. The method(s) described in this example may be modified or incorporated for use in various types of applications, measurements, or experiments. Two or more reagents, such as reagents A, B, C, are to be screened for the effects of different concentrations of reagents on some process, and the conditions under which an inhibitor can terminate the reaction of the enzyme with a substrate at various enzyme and substrate concentrations is of interest. If A is an enzyme, B a substrate, and C an inhibitor, a substrate with 5 inlets such as A/water/B/water/C inlets can be used, and the flow rates at which A, B and C are pumped into the substrate can be varied. Preferably, the size of the plug is kept constant by keeping the total flow rate of all plug-fluids constant. Because different amounts of A, B, C are introduced, the concentrations of A, B, C in the plugs will vary. The concentrations of the starting solutions need not be changed and one can rapidly screen all combinations of concentrations, as long as an enzymatic reaction or other reactions being screened can be detected or monitored. Because the solutions are flowing and the transport is linear, one can determine not only the presence or absence of an interaction or reaction, but also measure the rate at which a reaction occurs. Thus, both qualitative and quantitative data can be obtained. In accordance with the invention, the substrate typically need not be cleaned between runs since most, if not all, reagents are contained inside the plugs and leave little or no residue.

To extend the range over which concentrations can be varied, one may use a combination of, say, reagents A, B, C, D, E and prepare a micromolar solution of A, a mM solution of B, and a M solution of C, and so on. This technique may be easier than controlling the flow rate over a factor of, say, more than 106. Using other known methods is likely to be more difficult in this particular example because changing the ratio of reagents inside the plug requires changing the size of the plugs, which makes merging complicated.

In another example, one may monitor RNA folding in a solution in the presence of different concentrations of $Mg^{2+}$ and $H^+$. Previously, this was done using a stopped-flow technique, which is time consuming and requires a relatively large amount of RNA. Using a method according to the invention, an entire phase space can be covered in a relatively short period of time (e.g., approximately 15 minutes) using only µL/minute runs instead of the usual ml/shot runs.

These particular examples highlight the usefulness according to the invention in, for example, the study of protein/protein interaction mediation by small molecules, protein/RNA/DNA interaction mediation by small molecules, or binding events involving a protein and several small molecules. Other interactions involving several components at different concentrations may also be studied using the method according to the invention.

Generating Gradients in a Series of Plugs

In one aspect according to the invention, dispersion in a pressure-driven flow is used to generate a gradient in a continuous stream of plug-fluid. By forming plugs, the gradient is "fixed", i.e., the plugs stop the dispersion responsible for the formation of the gradient. Although the stream does not have to be aqueous, an aqueous stream is used as a non-limiting example below.

FIG. 44 illustrates how an initial gradient may be created by injecting a discrete aqueous sample of a reagent B into a flowing stream of water. In FIG. 44a), the water+B mixture flowed through channel 441. Channels 443 and 445 contain substantially non-flowing water+B mixture. Water streams were introduced into inlets 440, 442, 444, 446-448 while oil streams flowed through channels 449-452. FIG. 44d) shows a multiple-inlet system through which reagents A, B, and C are introduced through inlets 453, 454, and 455. A pressure-driven flow is allowed to disperse the reagent along the channel, thus creating a gradient of B along the channel. The gradient can be controlled by suitable adjustments or control of the channel dimensions, flow rates, injection volume, or frequency of sample or reagent addition in the case of multiple injections. This gradient is then "fixed" by the formation of plugs. Several of these channels are preferably combined into a single plug-forming region or section. In addition, complex gradients with several components may be created by controlling the streams. This technique may be used for various types of analysis and synthesis. For example, this technique can be used to generate plugs for protein or lysozome crystallization. FIG. 42 shows an experiment involving the formation of gradients by varying the flow rates (the experimental details are described in Example 17). FIG. 43 illustrates the use of gradients to form lysozyme crystals (the experimental details are described in Example 18).

Formation and Isolation of Unstable Intermediates

The devices and methods according to the present invention may also be used for synthesizing and isolating unstable intermediates. The unstable intermediates that are formed using a device according to the invention are preferably made to undergo further reaction and/or analysis or directed to other parts of the device where they may undergo further reaction and/or analysis. In one aspect, at least two different plug-fluids, which together react to form an unstable intermediate, are used. As the unstable intermediates form along the flow path of the substrate, information regarding, for example, the reaction kinetics can be obtained. Such unstable intermediates can be further reacted with another reagent by merging plugs containing the unstable intermediate with another plug-fluid. Examples of unstable intermediates include, but are not limited to, free radicals, organic ions, living ionic polymer chains, living organometallic polymer chains, living free radical polymer chains, partially folded proteins or other macromolecules, strained molecules, crystallization nuclei, seeds for composite nanoparticles, etc.

One application of devices according to the invention that involves the formation of unstable intermediates is high-throughput, biomolecular structural characterization. It can be used in both a time-resolved mode and a non-time resolved mode. Unstable (and/or reactive) intermediates (for example hydroxyl radicals (OH)) can be generated in one microfluidic stream (for example using a known reaction of metal ions with peroxides). These reactive species can be injected into another stream containing biomolecules, to induce reaction with the biomolecules. The sites on the biomolecule where the reaction takes place correlate with how accessible the sites are. This can be used to identify the sites exposed to the solvent or buried in the interior of the biomolecule, or identify sites protected by another biomolecule bound to the first one. This method could be applied to understanding structure in a range of biological problems. Examples include but are not limited to protein folding, protein-protein interaction (protein footprinting), protein-RNA interaction, protein-DNA interactions, and formation of protein-protein complexes in the presence of a ligand or ligands (such as a small molecule or another biomolecule). Interfacing such a system to a mass-spectrometer may provide a powerful method of analysis.

Experiments involving complex chemical systems can also be performed in accordance with the invention. For example, several unstable intermediates can be prepared in separate plugs, such as partially folded forms of proteins or RNA. The reactivity of the unstable intermediates can then be investigated when, for example, the plugs merge.

Dynamic Control of Surface Chemistry

Control of surface chemistry is particularly important in microfluidic devices because the surface-to-volume ratio increases as the dimensions of the systems are reduced. In particular, surfaces that are generally inert to the adsorption of proteins and cells are invaluable in microfluidics. Polyethylene glycols (PEG) and oligoethylene glycols (OEG) are known to reduce non-specific adsorption of proteins on surfaces. Self-assembled monolayers of OEG-terminated alkane thiols on gold have been used as model substrates to demonstrate and carefully characterize resistance to protein adsorption. Surface chemistry to which the solutions are exposed can be controlled by creating self-assembled monolayers on surfaces of silicone or grafting PEG-containing polymers on PDMS and other materials used for fabrication of microfluidic devices. However, such surfaces may be difficult to mass-produce, and they may become unstable after fabrication, e.g., during storage or use.

In one aspect according to the invention, the reagents inside aqueous plugs are exposed to the carrier-fluid/plug-fluid interface, rather than to the device/plug-fluid interface. Using perfluorocarbons as carrier-fluids in surface studies are attractive because they are in some cases more biocompatible than hydrocarbons or silicones. This is exemplified by the use of emulsified perfluorocarbons as blood substitutes in humans during surgeries. Controlling and modifying surface chemistry to which the reagents are exposed can be achieved simply by introducing appropriate surfactants into the fluorinated PFD phase.

In addition, the use of surfactants can be advantageous in problems involving unwanted adsorption of substances or particles, for example, on the channel walls. Under certain circumstances or conditions, a reaction may occur in one or more channels or regions of the substrate that give rise to particulates that then adhere to the walls of the channels. When they collect in sufficient number, the adhering particulates may thus lead or contribute to channel clogging or constriction. Using methods according to the invention, such as using one or more suitable surfactants, would prevent or minimize adhesion or adsorption of unwanted substances or particles to the channel walls thereby eliminating or minimizing, for example, channel clogging or constriction.

Encapsulated particulates may be more effectively prevented from interfering with desired reactions in one or more channels of the substrate since the particulates would be prevented from directly coming into contact with reagents outside the plugs containing the particulates.

Fluorosurfactants terminated with OEG-groups have been shown to demonstrate biocompatibility in blood substitutes and other biomedical applications. Preferably, oil-soluble fluorosurfactants terminated with oligoethylene groups are used to create interfaces in the microfluidic devices in certain applications. Surfactants with well-defined composition may be synthesized. This is preferably followed by the characterization of the formation of aqueous plugs in the presence of those surfactants. Their inertness towards non-specific protein adsorption will also be characterized. FIG. 24 shows examples of fluorinated surfactants that form monolayers that are: resistant to protein adsorption; positively charged; and negatively charged. For OEG-terminated surfactants, high values of n ($\geq$16) are preferred for making these surfactants oil-soluble and preventing them from entering the aqueous phase. In FIG. 24, compounds that have between about 3 to 6 EG units attached to a thiol are sufficient to prevent the adsorption of proteins to a monolayer of thiols on gold, and are thus preferred for inertness. In addition, surfactants that have been shown to be biocompatible in fluorocarbon blood substitutes may also be used as additives to fluorinated carrier fluids.

Applications: Kinetic Measurements and Assays

The devices and methods of the invention can be also used for performing experiments typically done in, for example, a microtiter plate where a few reagents are mixed at many concentrations and then monitored and/or analyzed. This can be done, for example, by forming plugs with variable composition, stopping the flow if needed, and then monitoring the plugs. The assays may be positionally encoded, that is, the composition of the plug may be deduced from the position of the plug in the channel. The devices and methods of the invention may be used to perform high-throughput screening and assays useful, for example, in diagnostics and drug discovery. In particular, the devices and methods of the invention can be used to perform relatively fast kinetic measurements.

The ability to perform fast measurements has revolutionized the field of biological dynamics. Examples include studies of protein C folding and cytochrome C folding. These measurements are performed using fast kinetics instruments that rely on turbulence to mix solutions rapidly. To achieve turbulence, the channels and the flow rates normally have to be large, which require large sample volumes. Commercially available instruments for performing rapid kinetics studies can access times on the order of 1 ms. The improved on-chip version of a capillary glass-ball mixer gives a dead time of about 45 µs with a flow rate of more than about 0.35 mL/sec. The miniaturization of these existing methods is generally limited by the requirement of high flow rate to generate turbulence. Miniaturization afforded by devices and methods according to the invention is advantageous because it allows, for example, quantitative characterization, from genetic manipulation and tissue isolation, of a much wider range of biomolecules including those available only in minute quantities, e.g., microgram quantities. In addition, these new techniques and instruments afford a wide range of accessible time scales for measurements.

Time control is important in many chemical and biochemical processes. Typically, stopped-flow type instruments are used to measure reaction kinetics. These types of instruments typically rely on turbulent flow to mix the reagents and transport them while minimizing dispersion. Because turbulent flow occurs in tubes with relatively large diameters and at high flow rates, stopped-flow instruments tend to use large volumes of reagents (e.g., on the order of ml/s). A microfluidic analog of a stopped-flow instrument that consumes small volumes of reagents, e.g., on the order of µL/min, would be useful in various applications such as diagnostics. Thus far, microfluidic devices have not been able to compete with stopped-flow instruments because EOF is usually too slow (although it has less dispersion), and pressure-driven flows tend to suffer from dispersion. In addition, mixing is usually very slow in both systems.

Stopped-flow instruments typically have sub-millisecond mixing, and could be useful for experiments where such fast mixing is required. The devices and methods of the invention allow sub-millisecond measurements as well. In particular, the present invention can be advantageous for reactions that occur on a sub-second but slower than about 1 or about 10 millisecond (ms) time scale or where the primary concern is the solute volume required to perform a measurement.

Further, if a plug is generated with two reactive components, it can serve as a microreactor as the plug is transported down a channel. A plug's property, such as its optical property, can then be measured or monitored as a function of distance from a given point or region of a channel or substrate. When the plugs are transported at a constant flow rate, a reaction time can be directly determined from a given distance. To probe the composition of the plug as it exits a channel, the contents of the plugs may be injected into a mass spectrometer (e.g., an electrospray mass spectrometer) from an end of the channel. The time corresponding to the end of the channel may be varied by changing the flow rate. Multiple outlets may be designed along the channels to probe, for example, the plug contents using a mass spectrometer at multiple distance and time points.

An advantage of the devices and methods of the invention is that when plugs are formed continuously, intrinsically slow methods of observation can be used. For example, plugs flowing at a flow rate of about 10 cm/s through a distance of about 1 mm from a point of origin would be about 10 ms old. In this case, the invention is particularly advantageous because it allows the use of a relatively slow detection method to repeatedly perform a measurement of, for example, 10 ms-old plugs for virtually unlimited time. In contrast, to observe a reaction in a stopped-flow experiment at a time, say, between about 9 and 11 ms, one only has about 2 ms to take data. Moreover, the present invention allows one to obtain information involving complex reactions at several times, simultaneously, simply by observing the channels at different distances from the point of origin.

The reaction time can be monitored at various points along a channel—each point will correspond to a different reaction or mixing time. Given a constant fluid flow rate u, one may determine a reaction time corresponding to the various times $t_1, t_2, t_3, \ldots t_n$ along the channel. Thus, if the distance between each pair of points n and n-1, which correspond to time tn and $t_{n4}$, are the same for a given value of n, then the reaction time corresponding to point n along the channel may be calculated from $t_n=nl/u$. Thus, one can conveniently and repeatedly monitor a reaction at any given time $t_n$. In principle, the substrate of the present invention allows one to cover a greater time period for monitoring a reaction by simply extending the length of the channel that is to be monitored at a given flow rate or by decreasing the flow rate over a given channel distance (see, for example, FIG. 22). In FIG. 22, the following can be introduced into the following inlets: enzyme into inlets 2201, 2205, 2210, 2215; buffer into inlets 2202, 2206, 2211, 2216; substrate into inlets 2203, 2207, 2212, 2217; buffer into inlets 2204, 2208, 2213, 2218; inhibitor into inlets 2228, 2209, 2214, 2219. In FIG. 22, a carrier fluid flows through the channel portions 2220, 2221, 2222, 2223 from left to right. The channel portions enclosed by the dotted square 2224, 2225, 2226, 2227 represent fields of view for the purpose of monitoring a reaction at various points along the channel.

The same principle applies to an alternate embodiment of the present invention, where the distance corresponding to a point n from a common point of origin along the channel differs from that corresponding to another channel by a power or multiples of 2. This can be seen more clearly from the following discussion. Given a constant fluid flow rate u, one may determine a reaction time corresponding to the various times $t_1, t_2, t_3, \ldots t_n$ along the channel. Thus, if the distance between each pair of points n and n-1, which correspond to time $t_n$ and $t_{n-1}$, are the same for a given value of n, then the reaction time corresponding to point n along the channel may be calculated from $t_n=nl/u$. In a relatively more complex channel geometry such as the one shown in FIG. 22(c), the corresponding equation is given by $t_n=2^{(n-1)}l/u$, which shows that the reaction times at various points n varies as a power or multiples of 2.

In one aspect, channels according to the invention are used that place into a field of view different regions that correspond to different time points of a reaction. The channels according to the invention allow various measurements such as those of a complete reaction profile, a series of linearly separated time points (such as those required for the determination of an initial reaction velocity in enzymology), and a series of exponentially separated time points (e.g., first-order kinetic measurements or other exponential analysis). Time scales in an image frame can be varied from microseconds to seconds by, for example, changing the total flow rate and channel length.

FIG. 22A-D show various examples of geometries of microfluidic channels according to the invention for obtaining kinetic information from single optical images. The illustrated channel systems are suitable for studies such as measurements of enzyme kinetics in the presence of inhibitors. The device shown in FIG. 22D has multiple outlets that can be closed or opened. In the device shown in FIG. 22D, preferably only one outlet is open at a time. At the fastest flow rates, the top outlet is preferably open, providing reduced pressure for flow through a short fluid path 1. As flow rates are reduced, other outlets are preferably opened to provide a longer path and a larger dynamic range for measurements at the same total pressure.

In FIG. 22, n is the number of segments for a given channel length 1 traveled by the reaction mixture in time to (see p. 73, second full paragraph for a related discussion of reaction times and channel lengths). These systems allow the control of the ratio of reagents by varying the flow rates. The systems also allow a quick quantification of enzyme inhibition.

For example, ribonuclease A can be used with known inhibitors such as nucleoside complexes of vanadium and oxovanadium ions and other small molecules such as 5'-diphosphoadenosine 3'-phosphate and 5'-diphosphoadenosine 2'-phosphate. The kinetics may be characterized by obtaining data and making Lineweaver-Burk, Eadie-Hofstee, or Hanes-Wolfe plots in an experiment. The experiment can be accomplished using only a few microliters of the protein and inhibitor solutions. This capability is particularly useful for characterizing new proteins and inhibitors that are available in only minute quantities, e.g., microgram quantities.

Kinetic measurements of reactions producing a fluorescent signal can be performed according to the invention by analyzing a single image obtained using, for example, an optical microscope. Long exposures (i.e., about 2 seconds) have been used to measure fast (i.e., about 2 milliseconds) kinetics. This was possible because in a continuous flow system, time is simply equal to the distance divided by the flow rate. In the continuous flow regime in accordance with the invention, the accessible time scales can be as slow as about 400 seconds, which can be extended to days or weeks if the flow is substantially slowed down or stopped. Typically, the time scale depends on the length of the channel (e.g., up to about 1 meter on a 3-inch diameter chip) at a low flow rate of about 1 mm/s, which is generally limited by the stability of the syringe pumps, but may be improved using pressure pumping. The fastest time scale is typically limited by the mixing time, but it may be reduced to about 20 μs in the present invention. Mixing time is generally limited by two main factors: (1) the mixing distance (e.g., approximately 10-15 times the width of the channel); and (2) the flow rates (e.g., approximately 400 mm/s, depending on the capillary number and the pressure drop required to drive the flow). Mixing distance is normally almost independent of the flow rate. By using suitable designs of microfluidic channels, or networks of microfluidic channels, a wide range of kinetic experiments can be performed.

Reducing the channel size generally reduces the mixing time but it also increases the pressure required to drive a flow. The equation below describes the pressure drop, ΔP (in units of Pa), for a single-phase flow in a rectangular capillary:

$$\Delta P = 28.42\ U \mu l/ab \qquad \text{Eqn. (9)}$$

where U (m/s) is the velocity of the flow, μ (kilogram/meter-second, kg m$^{-1}$ s$^{-1}$) is the viscosity of the fluid, l (m) is the length of the capillary, a (m) is the height of the capillary, and b (m) is the width of the capillary. There is generally a physical limitation on how much pressure a microfluidic device can withstand, e.g., about 3 atm for PDMS and about 5 atm for glass and Si. This limitation becomes crucial for very small channels and restricts the total length of the channel and thus the dynamic range (the total distance through which this flow rate can be maintained at a maximum pressure divided by the mixing distance) of the measurement.

FIG. 23 depicts a microfluidic network according to the invention with channel heights of 15 and 2 μm. The channel design shown in FIG. 23 illustrates how a dynamic range of about 100 can be achieved by changing the cross-section of the channels. Under these conditions, mixing time in the winding channel is estimated to be about 25 μs and observation time in the serpentine channels are estimated to be about 3 ms.

As FIG. 23 shows, rapid mixing occurs in the 2 μm×1 μm (height×width) channels and measurements are taken in the 2 μm×3 μm) channels. The table in FIG. 23 shows the distribution of the pressure drop, flow velocity, and flow time as a function of the channel cross-section dimensions. A transition from a 1-μm wide to 3-μm wide channels should occur smoothly, with plugs maintaining their stability and decreasing their velocity when they move from a 20-μm wide into a 50 μm wide channel. Changing the width of the channel can be easily done and easily incorporated into a mask design. The height of the channel can be changed by, for example, using photoresist layers having two different heights that are sequentially spun on, for example, a silicon wafer. A two-step exposure method may then be used to obtain a microfluidic network having the desired cross-section dimensions.

In another example of the application of the devices and methods of the present invention, the folding of RNase P catalytic domain (P RNA C-domain) of *Bacillus subtilis* ribozyme can be investigated using channels according to the invention. RNA folding is an important problem that remains largely unsolved due to limitations in existing technology. Understanding the rate-limiting step in tertiary RNA folding is important in the design, modification, and elucidation of the evolutionary relationship of functional RNA structures.

The folding of P RNA C-domain is known to involve three populated species: unfolded (U), intermediate (I), and native (N, folded) states. Within the first millisecond, the native secondary structure and some of the tertiary structure would have already folded (the RNA is compacted to about 90% of the native dimension) but this time regime cannot be resolved using conventional techniques such as stopped-flow. Using channels and substrates according to the invention, the time-dependence of the P RNA folding kinetics upon the addition of Mg$^{2+}$ can be studied.

Various types of assays (e.g., protein assays) known in the art, including absorbance assays, Lowry assays, Hartree-Lowry assays, Biuret assays, Bradford assays, BCA assays, etc., can be used, or suitably adapted for use, in conjunction with the devices and methods of the invention. Proteins in solution absorb ultraviolet light with absorbance maxima at about 280 and 200 nm. Amino acids with aromatic rings are the primary reason for the absorbance peak at 280 nm. Peptide bonds are primarily responsible for the peak at 200 nm. Absorbance assays offer several advantages. Absorbance assays are fast and convenient since no additional reagents or incubations are required. No protein standard need be prepared. The assay does not consume the protein and the relationship of absorbance to protein concentration is linear. Further, the assay can be performed using only a UV spectrophotometer.

The Lowry assay is an often-cited general use protein assay. It was the method of choice for accurate protein determination for cell fractions, chromatography fractions, enzyme preparations, and so on. The bicinchoninic acid (BCA) assay is based on the same principle, but it can be done in one step. However, the modified Lowry is done entirely at room temperature. The Hartree version of the Lowry assay, a more recent modification that uses fewer reagents, improves the sensitivity with some proteins, is less likely to be incompatible with some salt solutions, provides a more linear response, and is less likely to become saturated.

In the Hartree-Lowry assay, the divalent copper ion forms a complex with peptide bonds under alkaline conditions in which it is reduced to a monovalent ion. Monovalent copper ion and the radical groups of tyrosine, tryptophan, and cysteine react with Folin reagent to produce an unstable product that becomes reduced to molybdenum/tungsten blue. In addition to standard liquid handling supplies, the assay only requires a spectrophotometer with infrared lamp and filter. Glass or inexpensive polystyrene cuvettes may be used.

The Biuret assay is similar in principle to that of the Lowry, however it involves a single incubation of 20 minutes. In the Biuret assay, under alkaline conditions, substances containing two or more peptide bonds form a purple complex with copper salts in the reagent. The Biuret assay offer advantages in that there are very few interfering agents (ammonium salts being one such agent), and there were fewer reported deviations than with the Lowry or ultraviolet absorption methods. However, the Biuret consumes much more material. The Biuret is a good general protein assay for batches of material for which yield is not a problem. In addition to standard liquid handling supplies, a visible light spectrophotometer is needed, with maximum transmission in the region of 450 nm. Glass or inexpensive polystyrene cuvettes may be used.

The Bradford assay is very fast and uses about the same amount of protein as the Lowry assay. It is fairly accurate and samples that are out of range can be retested within minutes. The Bradford is recommended for general use, especially for determining protein content of cell fractions and assessing protein concentrations for gel electrophoresis. Assay materials including color reagent, protein standard, and instruction booklet are available from Bio-Rad Corporation. The assay is based on the observation that the absorbance maximum for an acidic solution of Coomassie Brilliant Blue G-250 shifts from 465 nm to 595 nm when binding to protein occurs. Both hydrophobic and ionic interactions stabilize the anionic form of the dye, causing a visible color change. The assay is useful since the extinction coefficient of a dye-albumin complex solution is constant over a 10-fold concentration range. In addition to standard liquid handling supplies, a visible light spectrophotometer is needed, with maximum transmission in the region of 595 nm, on the border of the visible spectrum (no special lamp or filter usually needed). Glass or polystyrene cuvettes may be used, but the color reagent stains both. Disposable cuvettes are recommended.

The bicinchoninic acid (BCA) assay is available in kit form from Pierce (Rockford, Ill.). This procedure is quite applicable to microtiter plate methods. The BCA is used for the same reasons the Lowry is used. The BCA assay is advantageous in that it requires a single step, and the color reagent is stable under alkaline conditions. BCA reduces divalent copper ion to the monovalent ion under alkaline conditions, as is accomplished by the Folin reagent in the Lowry assay. The advantage of BCA is that the reagent is fairly stable under alkaline condition, and can be included in the copper solution to allow a one step procedure. A molybdenum/tungsten blue product is produced as with the Lowry. In addition to standard liquid handling supplies, a visible light spectrophotometer is needed with transmission set to 562 nm. Glass or inexpensive polystyrene cuvettes may be used.

The range of concentrations that can be measured using the above assays range from about 20 micrograms to 3 mg for absorbance at 280, between about 1-100 micrograms for absorbance at 205 nm, between about 2-100 micrograms for the Modified Lowry assay, between about 1-10 mg for the Biuret assay, between about 1-20 micrograms for the Bradford assay, and between about 0.2-50 micrograms for BCA assay. Many assays based on fluorescence or changes in fluorescence have been developed and could be performed using methods and devices of the invention.

A detailed description of various physical and chemical assays is provided in Remington: The Science and Practice of Pharmacy, A. R. Gennaro (ed.), Mack Publishing Company, chap. 29, "Analysis of Medicinals," pp. 437-490 (1995) and in references cited therein while chapter 30 of the same reference provides a detailed description of various biological assays. The assays described include titrimetric assays based on acid-base reactions, precipitation reactions, redox reactions, and complexation reactions, spectrometric methods, electrochemical methods, chromatographic methods, and other methods such as gasometric assays, assays involving volumetric measurements and measurements of optical rotation, specific gravity, and radioactivity. Other assays described include assays of enzyme-containing substances, proximate assays, alkaloidal drug assays, and biological tests such as pyrogen test, bacterial endotoxin test, depressor substances test, and biological reactivity tests (in-vivo and in-vitro)

In addition, *Remington: The Science and Practice of Pharmacy*, A. R. Gennaro (ed.), Mack Publishing Company, chap. 31, "Clinical Analysis," pp. 501-533 (1995) and references cited therein provide a detailed description of various methods of characterizations and quantitation of blood and other body fluids. In particular, the reference includes a detailed description of various tests and assays involving various body fluid components such as erythrocytes, hemoglobin, thrombocyte, reticulocytes, blood glucose, nonprotein nitrogen compounds, enzymes, electrolytes, blood-volume and erythropoeitic mechanisms, and blood coagulation.

Nonlinear and Stochastic Sensing

Stochastic behavior has been observed in many important chemical reactions, e.g., autocatalytic reactions such as inorganic chemical reactions, combustion and explosions, and in polymerization of sickle-cell hemoglobin that leads to sickle-cell anemia. Crystallization may also be considered an autocatalytic process. Several theoretical treatments of these reactions have been developed. These reactions tend to be highly sensitive to mixing.

Consider the extensively studied stochastic autocatalytic chemical reaction between $NaClO_2$ and $Na_2S_2O_3$ (chlorite-thiosulfate reaction). The mechanism of this reaction can be described by reactions (1) and (2),

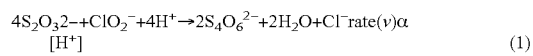

$$4S_2O_3^{2-}+ClO_2^-+4H^+ \rightarrow 2S_4O_6^{2-}+2H_2O+Cl^- \text{ rate}(v) \alpha [H^+] \qquad (1)$$

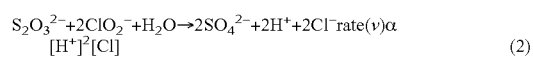

$$S_2O_3^{2-}+2ClO_2^-+H_2O \rightarrow 2SO_4^{2-}+2H^++2Cl^- \text{ rate}(v)\alpha [H^+]^2[Cl^-] \qquad (2)$$

where [H$^+$] stands for the concentration of H. At a slightly basic pH=7.5, the slow reaction (1) dominates and maintains a basic pH of the reaction mixture (since the rate of this reaction v is directly proportional [H$^+$], this reaction consumes H$^+$ and is auto-inhibitory). Reaction (2) dominates at acidic pH (since the rate of this reaction varies in proportion to [H$^+$]2[Cl$^-$], this reaction produces both H$^+$ and Cl$^-$ and is superautocatalytic). FIG. 21 shows the reaction diagram for two reactions corresponding to the curves 211, 212. The rates of the two reactions (referred to here as reaction 211 and reaction 212) are equal at an unstable critical point at a certain pH. The lifetime of the reaction mixtures of NaClO$_2$ and NaS$_2$O$_3$ at this critical point crucially depends on stirring. In the absence of stirring, stochastic fluctuations of [H$^+$] in solution generate a localized increase in [H$^+$]. This increase in [H$^+$] marginally increases the rate of reaction 212, but it has a much stronger accelerating effect on reaction 211 because of the higher-order dependence on [H$^+$] of this reaction. Therefore, in the region where local fluctuations increase local [H$^+$], reaction 211 becomes dominant, and more H$^+$ is produced (which rapidly diffuses out of the region of the initial fluctuation). The initiated chemical wave then triggers the rapid reaction of the entire solution. Unstirred mixtures of NaClO$_2$ and NaS$_2$O$_3$ are stable only for a few seconds, and these fluctuations arise even in the presence of stirring.

FIG. 21 depicts a reaction diagram illustrating an unstable point in the chlorite-thiosulfate reaction. At [H$^+$] values below the critical point, the slow reaction (1) dominates. At [H$^+$] values above the critical point, the autocatalytic reaction (2) dominates. The reaction mixture at the [H$^+$] value equal to the critical point is metastable in the absence of fluctuations. Under perfect mixing, the effects of small fluctuations average out and the system remains in a metastable state. Under imperfect mixing, fluctuations that reduce [H$^+$] grow more slowly than those that increase [H$^+$] due to the autocatalytic nature of reaction (2), and the reaction mixture thus rapidly becomes acidic.

It is known that chaotic flows should have a strong effect on diffusive transport within the fluid ("anomalous diffusion"). It is also known that chaotic dynamics can lead to non-Gaussian transport properties ("strange kinetics"). In one aspect according to the invention, these highly unstable mixtures are stabilized in the presence of chaotic mixing using channels according to the invention because this mixing can effectively suppress fluctuations. This invention can be used to understand the effects of mixing on the stochastic behavior of such systems, including for example, the chlorite thiosulfate system.

In a laminar flow, the flow profile in the middle of the channel is flat and there is virtually no convective mixing. Fluctuations involving [$H^+$] that arise in the middle of the channel can grow and cause complete decomposition of the reaction mixture. Slow mixing reduces the probability of fluctuations in plugs moving through straight channels. When fluctuations that occur in the centers of vortices are not efficiently mixed away, one or more spontaneous reactions involving some of the plugs can take place. In the present invention, chaotic mixing in plugs moving through winding channels efficiently mix out fluctuations, and thus substantially fewer or no spontaneous reactions are expected to occur.

In a simple laminar flow, there is normally very little or no velocity gradient and substantially no mixing at the center of the channel. Thus, fluctuations that arise in the chlorite-thiosulfate reaction mixture prepared at the critical [$H^+$] are able to grow and lead to rapid decomposition of the reaction mixture. Propagation of chemical fronts in autocatalytic reactions occurring in laminar flows has been described with numerical simulations, and back-propagation has been predicted (that is, a reaction front traveling upstream of the direction of the laminar flow). Using the method of the present invention, this back-propagation involving the reaction between $NaClO_2$ and $NaS_2O_3$ under laminar flow conditions was observed.

In accordance with the invention, chaotic flow within plugs that flow through winding channels suppresses fluctuations and gives rise to stable reaction mixtures. There exists, of course, a finite probability that fluctuations can arise even in a chaotically stirred plug. In one aspect according to the invention, the details of the evolution of these reactions are monitored using a high-speed digital camera. The plugs are preferably separated by the oil and are not in communication with each other, so the reaction of one plug will not affect the behavior of the neighboring plug. Statistics covering the behavior of thousands of plugs can be obtained quickly under substantially identical experimental conditions.

Whether a fluctuation would be able to trigger an autocatalytic reaction depends on factors such as the magnitude of a fluctuation and its lifetime. The lifetime of a fluctuation is typically limited by the mixing time in the system. In an unstirred solution, mixing is by diffusion and quite slow, and fluctuations may persist and lead to autocatalytic reactions. In a stirred solution, the lifetime of a fluctuation is relatively short, and only large fluctuations have sufficient time to cause an autocatalytic reaction.

Mixing time and the lifetime of fluctuations typically depend on the size of the plugs. As plug size decreases, mixing is accelerated and fluctuations are suppressed. However, very small plugs (e.g., about 1 $\mu m^3$ or $10^{-15}$ L) in a solution containing about $10^{-8}$ mole/liter concentration of $H^+$ (pH=8) will contain only a few $H^+$ ions per plug (about $10^{-23}$ moles or about $6H^+$ ions). When such small plugs are formed, the number of $H^+$ ions in them will have a Poisson distribution.

An important experimental challenge is to establish that the stochastic behavior in these systems is due mainly to internal fluctuations of concentrations. Other factors that may act as sources of noise and instability are: (1) temporal fluctuations in the flow rates of the incoming reagent streams, which can lead to the formation of plugs with varying amounts of reagents; (2) temperature fluctuations in solutions in a microfluidic device, which may arise due to, for example, illumination by a microscope; and (3) fluctuations due to impurities in carrier-fluids leading to variations in the surface properties of different plugs.

Microfluidic systems according to the invention may be used to probe various chemical and biochemical processes, such as those that show stochastic behavior in bulk due to their nonlinear kinetics. They can also be used in investigating processes that occur in systems with very small volumes (e.g., about 1 $\mu m^3$, which corresponds to the volume of a bacterial cell). In systems with very small volumes, even simple reactions are expected to exhibit stochastic behavior due to the small number of molecules localized in these volumes.

Autocatalytic reactions present an exciting opportunity for highly sensitive detection of minute amounts of autocatalysts. Several systems are known to operate on this principle, silver-halide photography being the most widely used. In silver-halide photography, the energy of photons of light is used to decompose an emulsion of silver halide AgX into nanometer-sized particles of metallic silver. A film that is embedded with the silver particles is then chemically amplified by the addition of a metastable mixture of a soluble silver(I) salt and a reducing agent (hydroquinone). Metallic silver particles catalyze reduction of silver(I) by hydroquinone, leading to the growth of the initial silver particles. Another example of an autocatalytic reaction is the polymerase-chain reaction (PCR), which is a very effective amplification method that has been widely used in the biological sciences.

However, a dilemma occurs when designing systems with very high sensitivity and amplification. To achieve a very highly sensitive amplification, the system typically has to be made very unstable. On the other hand, an unstable system is very sensitive to noise and has a very short lifetime. Also, in unstable systems, it is difficult to distinguish between spontaneous decomposition and a reaction caused by the analyte. In one aspect, microfluidic devices according to the invention, which allow chaotic mixing and compartmentalization, are used to overcome this problem.

To demonstrate the potential of microfluidic systems according to the present invention, a microfluidic system according to the invention is used to handle unstable mixtures. In one application, a microfluidic system according to the invention is preferably used to control a stochastic reaction between $NaClO_2$ and $NaS_2O_3$. In particular, this reaction is preferably used for a highly sensitive amplification process.

If a plug containing an unstable reaction mixture of $NaClO_2$ and $NaS_2O_3$ is merged with a small plug containing an amount of H+ sufficient to bring the local concentration of H+ above critical, a rapid autocatalytic reactions is generally triggered. This autocatalytic reaction typically leads to the production of large amounts of H. Thus, a weak chemical signal, e.g., a small amount of $H^+$, is rapidly amplified by an unstable reaction mixture. Thus, for example, this approach can be used to investigate biological reactions such as those that involve enzymes, in which small amounts of H+ are produced.

The above autocatalytic system possesses several features that contribute to its novelty and usefulness. In one aspect, an unstable amplifying reaction mixture is prepared in-situ and is used within milliseconds before it has a chance to decompose. Preferably, the system is compartmentalized so a reaction that occurs in one compartment does not affect a reaction in another compartment. This compartmentalization allows thousands of independent experiments to be conducted in seconds using only minute quantities of samples.

Importantly, chaotic mixing in the system reduces fluctuations and stabilizes the reaction mixture.

The applications of controlled autocatalytic amplification in accordance with the invention are not limited to the detection of protons or $Co^{2+}$ ions. For example, the (Co(III)-5-Br-PAPS)/peroxomonosulfate oxidation reaction can also be used indirectly, for example, for a detection of small amounts of peroxidase, which can be used as a labeling enzyme bound to an antibody. The (Co(III)-5-Br-PAPS)/peroxomonosulfate oxidation reaction, which has been characterized analytically, involves the autocatalytic decomposition of violet bis [2-(5-bromo-pyridylazo)-5-(N-propyl-N-sulfopropyl-amino-phenolato]cobaltate, (Co(III)-5-Br-PAPS), upon oxidation with potassium peroxomonosulfate to produce colorless $Co^{2+}$ ions, which serve as the autocatalyst (the order of autocatalysis has not been established for this reaction). (Endo et al., "Kinetic determination of trace cobalt(II) by visual autocatalytic indication," Talanta, 1998, vol. 47, pp. 349-353; Endo et al., "Autocatalytic decomposition of cobalt complexes as an indicator system for the determination of trace amounts of cobalt and effectors," Analyst, 1996, vol. 121, pp. 391-394.)

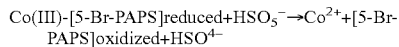

Addition of small amounts of $Co^{2+}$ to the violet mixture of the (Co(III)-5-Br-PAPS and peroxomonosulfate produces an abrupt loss of color to give a colorless solution. The time delay before this decomposition depends on the amount of the $Co^{2+}$ added to the solution. This reaction has been used to detect concentrations of $Co^{2+}$ as low as $1\times 10^{-10}$ mole/L. The reaction shows good selectivity in the presence of other ions (V(V), Cr(III), Cr(VI), Mn(II), Fe(II), Ni(II), Cu(II) and Zn(II)).

The devices and methods according to the invention may be applied to other autocatalytic reactions, some of which have been described in inorganic, organic and biological chemistry. Reactions of transition metal ions such as Cr(III) (B82) $Mn^{2+}$ or colloidal $MnO_2$, and reactions of halides and oxohalides are often autocatalytic. Autocatalysis involving lanthanides ($Eu^{2+}$) and actinides ($U^{4+}$) has also been reported. All of these elements are potential targets for detection and monitoring in chemical waste, drinking water, or biological fluids. Intriguing possibilities arise from using asymmetric autocatalytic reactions to detect minute amounts of optically active, chiral impurities, such as biomolecules.

It is also possible to design new autocatalytic reactions. Autocatalysis is abundant in biology, and many enzymes are autocatalytic (e.g., caspases involved in programmed cell death, kinases involved in regulation and amplification, and other enzymes participating in metabolism, signal transduction, and blood coagulation. Emulsions of perfluorocarbons such as perfluorodecaline (PFD) are used as blood substitutes in humans during surgeries and should be compatible with a variety of biological molecules. Since the feasibility of quantitative measurements of enzyme kinetics has been demonstrated using plugs formed according to the invention, plugs formed according to the invention may also be applied to the detection of biological autocatalysts.

The devices and methods according to the present invention are not limited to the detection of the autocatalyst itself. For example, the labeling of an analyte using an autocatalyst is also within the scope of the present invention. Biomolecules are often labeled with metallic nanoparticles. Such metallic nanoparticles are highly effective autocatalysts for the reduction of metal ions to metals. Preferably, the systems and methods of the present invention are used in the visual detection of a single molecule of DNA, RNA, or protein labeled with nanoparticles via an autocatalytic pathway. In preliminary experiments in accordance with the invention, clean particle formation and transport within plugs were observed.

In addition, the generation of metal (e.g., copper, silver, gold, nickel) deposits and nanoparticles upon chemical reduction also proceed by an autocatalytic mechanism. These reactions are commonly used for electroless deposition of metals and should be useful for the detection of minute amounts of metallic particles. The presence of metallic particles in water can be indicative of the presence of operating mechanical devices. In one aspect according to the invention, devices and methods according to the invention are used to detect the presence of minute or trace quantities of metallic particles.

The devices in accordance with the present invention are simple in design, consume minute amounts of material, and robust. They do not require high voltage sources and can be operated, for example, using gravity or a pocket-sized source of compressed air. In one aspect, the systems according to the invention are used in portable and hand-held devices.

Autocatalytic reactions show a threshold response, that is, there is a very abrupt temporal change from unreacted mixture to reacted mixture. In the case where time is equal to distance, this abrupt transition over a short distance can be observed using the devices and methods of the invention. The time (and distance) is very sensitive to the initial concentration of the catalyst, and thus it should be easy to determine the concentration of the autocatalyst in the sample by noting how far the reaction system traveled before it reacted.

One example of an autocatalytic process is blood coagulation. It is very sensitive to flow and mixing, therefore experimenting with it in the absence of flow gives unreliable results or results that have little relevance to the real function of the coagulation cascade. A typical microfluidic system may be difficult to use with blood because once coagulation occurs, it blocks the channel and stops the flow in the microfluidic device. In addition, coagulated blood serves as an autocatalyst; even small amounts of coagulated blood in the channels can make measurements unreliable.

These problems can be overcome using the devices of the present invention. Using plugs, autocatalytic reactions can be easily controlled, and the formation of solid clots would not be a problem because any solids formed will be transported inside the plugs out of the channel without blocking the channel and without leaving autocatalytic residue. In addition, flow inside plugs can be easily controlled and adjusted to resemble flow under physiological conditions.

To address the sensitivity of blood coagulation to surfaces (the cascade is normally initiated on the surface), microscopic beads containing immobilized tissue factor (the cascade initiator) on the surface may be added to one of the streams and transported inside the plugs. Also, surfactants may be used to control surface chemistry.

Thus, the devices and methods of the invention may be used, for example, to test how well the coagulation cascade functions (e.g., for hemophilia or the tendency to form thrombus) under realistic flow conditions. This test would be particularly valuable in diagnostics. Blood may be injected in one stream, and a known concentration of a molecule known to induce coagulation (e.g., factor VIIa) can be added through another stream prior to plug formation. At a given flow rate, normal blood would coagulate at a certain distance (which corresponds to a given time), which can be observed optically by light scattering or microscopy. Blood of hemophiliac patients would coagulate at a later time. This type of testing would be useful before surgical operations. In particular, this type of testing is important for successful child delivery, especially when hemophilia is suspected. Fetal testing may be performed since only minute amounts of blood are required by systems according to the invention. The blood may be injected directly from the patient or collected in the presence of anticoagulating agent (for example EDTA), and then reconstituted in the plug by adding $Ca^{2+}$. In some cases, the addition of $Ca^{2+}$ may be sufficient to initiate the coagulation cascade.

The devices and methods of the invention may also be used to evaluate the efficacy of anticoagulating agents under realistic flow conditions. Plugs can be formed from normal blood (which may be used directly or reconstituted by adding $Ca^{2+}$ or other agents), an agent known to induce coagulation, and an agent (or several agents that need to be compared) being tested as an anticoagulation agent. The concentrations of these agents can be varied by varying the flow rates. The distance at which coagulation occurs is noted, and the efficacy of various agents to prevent coagulation is compared. The effects of flow conditions and presence of various compounds in the system on the efficacy of anticoagulation agents can be investigated quickly. The same techniques may also be used to evaluate agents that cause, rather prevent, coagulation. These tests could be invaluable in evaluating drug candidates.

Synthesis

In accordance with the present invention, a method of conducting a reaction within a substrate is provided. The reaction is initiated by introducing two or more plug-fluids containing reactants into the substrate of the present invention.

In one aspect, the plug-fluids include a reagent and solvent such that mixing of the plug-fluids results in the formation of a reaction product. In another embodiment, one of the plug-fluids may be reagent free and simply contain fluid. In this embodiment, mixing of the plug-fluids will allow the concentration of the reagent in the plug to be manipulated.

The reaction can be initiated by forming plugs from each plug-fluid and subsequently merging these different plugs.

When plugs are merged to form merged plugs, the first and second set of plugs may be substantially similar or different in size. Further, the first and second set of plugs may have different relative velocities. In one embodiment, large arrays of microfluidic reactors are operated in parallel to provide substantial throughput.

The devices and methods of the invention can be used for synthesizing nanoparticles. Nanoparticles that are monodisperse are important as sensors and electronic components but are difficult to synthesize (Trindade et al., Chem. Mat. 2001, vol. 13, pp. 3843-3858.). In one aspect, monodisperse nanoparticles of semiconductors and noble metals are synthesized under time control using channels according to the invention (Park et al, J. Phys. Chem. B, 2001, vol. 105, pp. 11630-11635.). Fast nucleation is preferably induced by rapid mixing, thereby allowing these nanoparticles to grow for a controlled period of time. Then their growth is preferably quickly terminated by passivating the surfaces of the particles with, for example, a thiol. Nanoparticles of different sizes are preferably obtained by varying the flow rate and therefore the growth time. In addition, devices according to the invention can be used to monitor the synthesis of nanoparticles, and thus obtain nanoparticles with the desired properties. For example, the nanoparticle formation may be monitored by measuring the changes in the color of luminescence or absorption of the nanoparticles. In addition, the growth of nanoparticles may be stopped by introducing a stream of quenching reagent at a certain position along the main channel.

Rapid millisecond mixing generated in channels according to the invention can help ensure the formation of smaller and much more monodisperse nanoparticles than nanoparticles synthesized by conventional mixing of solutions. FIG. 13 shows the UV-VIS spectra of CdS nanoparticles formed by rapid mixing in plugs (lighter shade spectrum with sharp absorption peak) and by conventional mixing of solutions (darker shade spectrum). The sharp absorption peak obtained for synthesis conducted in plugs indicates that the nanoparticles formed are highly monodisperse. In addition, the blue-shift (shift towards shorter wavelengths) of the absorption peak indicates that the particles formed are small.

FIG. 14A-B illustrates the synthesis of CdS nanoparticles performed in PDMS microfluidic channels in single-phase aqueous laminar flow (FIG. 14A) and in aqueous plugs that were surrounded by water-immiscible perfluorodecaline (FIG. 14B). In FIGS. 14A-B, $Cd^{2+}$ was introduced into inlets 1400, 1403, aqueous stream was introduced into inlets 1401, 1404, and $S^{2-}$ was introduced into inlets 1402, 1405. In FIG. 14A, an aqueous stream flowed through channel 1406 while in FIG. 14B, oil flowed through channel 1407. FIG. 14A shows portions of the channels 1408 and 1410 at time t=6 minutes and portions of the channels 1409, 1411 at time t=30 minutes. It can be seen in FIG. 14A that when laminar flow is used in the synthesis, large amounts of CdS precipitate form on the channel walls. When plugs were used for the synthesis, all CdS formed inside the plugs, and no surface contamination was observed. FIG. 15 illustrates a technique for the synthesis of CdS nanoparticles, which is discussed in detail in Example 13 below.

The following methods according to the invention can be used in synthesis involving nanoparticles:

(a) using self-assembled monolayers to nucleate nanoparticles with crystal structures not accessible under homogeneous nucleation conditions (e.g., controlling polymorphism by controlling the surface at which nucleation takes place).

(b) using merging of plugs to create core-shell nanoparticles with a range of core and shell sizes. In a stream of plugs of a first channel, small core nanoparticles such as CdSe particles can be synthesized in a matter of few milliseconds. The CdSe particles can then be used as seeds for mixing with solutions such as those containing $Zn^{+2}$ and $S^{-2}$. The CdSe particles, acting as seeds for the formation of ZnS, thus allow the formation of CdSe(core)/ZnS(shell) nanoparticles. Core-shell particles with more than two layers may be obtained by simply repeating the merging process more than once.

(c) using merging of plugs to create composite nanoparticles. For example, small nanoparticles of CdSe and ZnS can be formed using streams of plugs from two separate channels. Merging of these streams leads to aggregation of these particles to form larger nanoparticles containing CdSe/ZnS composite. The composite nanoparticles that contain only a few of the original nanoparticles can be made non-centrosymmetric, which may have interesting photophysical properties.

(d) using the devices and methods according to the invention to synthesize medically important nanoparticles, such as encapsulated drugs and composite drugs.

(e) combinatorial synthesis of core-shell particles and other complex systems. For example, the luminescence of CdSe/ZnS particles may be monitored and the conditions adjusted to produce particles with various core and shell sizes, various doping impurities in the core and shell, and various ligand composition on the surface of the particles. These can be conducted in real time using a device according to the invention. The entire process can also be automated.

The devices and methods according to the present invention may also be used for synthesizing polymers. Since the invention allows precise control of the timing of a polymerization reaction, one or more properties of a polymer such as molecular weight, polydispersity and blockiness can be readily controlled or adjusted. In addition, use of the substrate of the present invention allows the user to precisely form block copolymers by merging plugs within a device, since the path length of the channel will correspond to a specific duration of the polymerization reaction. Similarly, a living polymer chain can be terminated with a specific end group to yield polymers with a discrete subset of molecular weights.

In addition, combinatorial libraries of drug candidates may be synthesized using similar approaches. The library may be encoded using the position of plugs in a channel. Plugs of variable composition may be created by varying flow rates. Combination of synthesis of the library may be combined with screening and assays performed on the same microfluidic chip according to the present invention. In some embodiments, merging, splitting and sorting of plugs may be used during synthesis, assays, etc.

All of the above synthesis methods of the present invention can be used to form macroscopic quantities of one or more reaction products by running multiple reactions in parallel.

Particle Separation/Sorting Using Plugs

The flow within the moving plugs can be used for separation of polymers and particles. Plugs can be used for separation by first using flow within a moving plug to establish a distribution of the polymers or particles inside the plug (for example, an excess of the polymer inside the front, back, right or left side of the plug) and then using splitting to separate and isolate the part of the plug containing higher concentration of the polymers or particles. When two polymers or particles are present inside the plug and establish different distributions, slitting can be used to separate the polymers or particles. This approach may be useful, for example, in achieving on a microfluidic chip any of, but not limited to, the following: separation, purification, concentration, membrane-less dialysis, and filtration.

Crystallization

The devices and methods of the invention allow fast, inexpensive miniaturization of existing crystallization methods and other methods that can be adapted into, for example, novel protein screening and crystallization techniques. The crystallization methods according to the invention may be applied to various drugs, materials, small molecules, macromolecules, colloidal and nanoparticles, or any of their combinations. Many relevant protein structures remain undetermined due to their resistance to crystallization. Also, many interesting proteins are only available in microgram quantities. Thus, a screening process must permit the use of small amounts protein for analysis. Current crystallization screening technologies generally determine the ideal conditions for protein crystallization on a milligram scale. Devices and methods according to the invention improve current bench-top methodology available to single users, and enables higher throughput automated systems with improved speed, sample economy, and entirely new methods of controlling crystallization.

A microfluidic system according to the invention can be applied to the crystallization of small molecules or macromolecules and their complexes.

For example, systems and methods in accordance with the present invention may include but are not limited to: (1) biological macromolecules (cytosolic proteins, extracellular proteins, membrane proteins, DNA, RNA, and complex combinations thereof); (2) pre- and post-translationally modified biological molecules (including but not limited to, phosphorylated, sulfolated, glycosylated, ubiquitinated, etc. proteins, as well as halogenated, abasic, alkylated, etc. nucleic acids); (3) deliberately derivatized macromolecules, such as heavy-atom labeled DNAs, RNAs, and proteins (and complexes thereof), selenomethionine-labeled proteins and nucleic acids (and complexes thereof), halogenated DNAs, RNAs, and proteins (and complexes thereof); (4) whole viruses or large cellular particles (such as the ribosome, replisome, spliceosome, tubulin filaments, actin filaments, chromosomes, etc.); (5) small-molecule compounds such as drugs, lead compounds, ligands, salts, and organic or metallo-organic compounds; (6) small-molecule/biological macromolecule complexes (e.g., drug/protein complexes, enzyme/substrate complexes, enzyme/product complexes, enzyme/regulator complexes, enzyme/inhibitor complexes, and combinations thereof); (7) colloidal particles; and (8) nanoparticles.

Preferably, a general crystallization technique according to the present invention involves two primary screening steps: a crude screen of crystallization parameters using relatively small channels with a large number of small plugs, and a fine screen using larger channels and larger plugs to obtain diffraction-quality crystals. For example, ten crude screens performed using channels with a $(50\ \mu m)^2$ cross-sectional dimension and with more or less one thousand 150-picoliter (pL) plugs corresponding to 10 mg/mL final concentration of a protein (10,000 trials total) will typically require about 1.5 µL of solution, produce crystals up to about $(10\ \mu m)^3$ in size, and will consume approximately 15 µg of protein. Up to 300 or more of such plugs can be formed in about 1 second in these microfluidic networks. A fine screen around optimal conditions in $(500\ \mu m)^2$ channels is expected to use more or less 50 plugs. Another ~5 µL of solution and another 50 µg of the protein are expected to be consumed. This can produce crystals up to $(100\ \mu m)^3$ in size. Approximately 30 plugs can be formed about every second or so. The throughput of the system will generally be determined by the rate of plug formation, and may be limited by how rapidly the flow rates can be varied. Pressure control methods that operate at frequencies of 100 Hz are available and may be applied to PDMS microfluidic networks (Unger et al., "Monolithic fabricated valves and pumps by multilayer soft lithography," Science 2000, vol. 288, pp. 113-116.).

Crystal properties such as appearance, size, optical quality, and diffractive properties may be characterized and measured under different conditions. For example, a Raxis IIc X-ray detector mounted on a Rigaku RU 200 rotating anode X-ray generator, which is equipped with double focusing mirrors and an MSC cryosystem, may be used for at least some of the characterizations and measurements. A synchrotron beam may be useful for characterization of small crystals. Also, these devices and methods may be used to build microfluidic systems according to the invention that are compatible with structural studies using x-ray beams.

A significant problem involving current crystallization approaches is determining the conditions for forming crystals with optimal diffractive properties. Normally crystals have to be grown, isolated, mounted, and their diffractive properties determined using an x-ray generator or a synchrotron. Microfluidic systems with thin, non-scattering walls would be desirable for determining the diffractive properties of crystals inside a microfluidic system. Preferably, crystallization is carried out inside this system using methods according to the invention, which are described herein. The crystals are exposed to x-ray beams either to determine their structure or diffractive properties (the screening mode). For example, a PDMS membrane defining two side walls of the channels could be sandwiched between two very thin glass plates (defining the top and bottom walls of the channels) that do not significantly scatter X-rays. Thus, the devices of the invention offer a further advantage in that structural characterization could be conducted while the sample is inside the microfluidic device. Thus, the sample can be characterized without the need to take out the sample, e.g., crystal, from the device.

The present system enables higher throughput automated systems with improved speed, sample economy, and entirely new methods of controlling crystallization. Microfluidic versions of microbatch, vapor phase diffusion and FID techniques may be carried out using the present invention, as described below, or using a combination of these techniques or other techniques. In addition, the nucleation and growth phases may be carried out in discrete steps through merging plugs, as described herein.

Screening for protein crystallization involves varying a number of parameters. During crystallization screening, a large number of chemical compounds may be employed. These compounds include salts, small and large molecular weight organic compounds, buffers, ligands, small-molecule agents, detergents, peptides, crosslinking agents, and derivatizing agents. Together, these chemicals can be used to vary the ionic strength, pH, solute concentration, and target concentration in the plug, and can even be used to modify the target. The desired concentration of these chemicals to achieve crystallization is variable, and can range from nanomolar to molar concentrations.

A typical crystallization mix contains set of fixed, but empirically-determined, types and concentrations of precipitation agent, buffers, salts, and other chemical additives (e.g., metal ions, salts, small molecular chemical additives, cryoprotectants, etc.). Water is a key solvent in many crystallization trials of biological targets, as many of these molecules may require hydration to stay active and folded. Precipitation agents act to push targets from a soluble to insoluble state, and may work by volume exclusion, changing the dielectric constant of the solvent, charge shielding, and molecular crowding. Precipitation agents compatible with the PDMS material of certain embodiments according to the invention include, but are not limited to, nonvolatile salts, high molecular weight polymers, polar solvents, aqueous solutions, high molecular weight alcohols, divalent metals.

Precipitation agents, which include large and small molecular weight organics, as well as certain salts, may be used from under 1% to upwards of 40% concentration, or from <0.5M to greater than 4M concentration. Water itself can act in a precipitating manner for samples that require a certain level of ionic strength to stay soluble. Many precipitation agents may also be mixed with one another to increase the chemical diversity of the crystallization screen. Devices according to the invention are readily compatible with a broad range of such compounds.

A nonexclusive list of salts that may be used as precipitation agents is as follows: tartrates (Li, Na, K, Na/K, $NH_4$); phosphates (Li, Na, K, Na/K, $NH_4$); acetates (Li, Na, K, Na/K, Mg, Ca, Zn, $NH_4$); formates (Li, Na, K, Na/K, Mg, $NH_4$); citrates (Li, Na, K, Na/K, $NH_4$); chlorides (Li, Na, K, Na/K, Mg, Ca, Zn, Mn, Cs, Rb, $NH_4$); sulfates (Li, Na, K, Na/K, $NH_4$); maleates (Li, Na, K, Na/K, $NH_4$); glutamates (Li, Na, K, Na/K, $NH_4$).

A nonexclusive list of organic materials that may be used as precipitation agents is as follows: PEG 400; PEG 1000; PEG 1500; PEG 2K; PEG 3350; PEG 4K; PEG 6K; PEG 8K; PEG 10K; PEG 20K; PEG-MME 550; PEG-MME 750; PEG-MME 2K; PEGMME 5K; PEG-DME 2K; dioxane; methanol; ethanol; 2-butanol; n-butanol; t-butanol; jeffamine m-600; isopropanol; 2-methyl-2,4-pentanediol; 1,6 hexanediol.

Solution pH can be varied by the inclusion of buffering agents; typical pH ranges for biological materials lie anywhere between values of 3 and 10.5 and the concentration of buffer generally lies between 0.01 and 0.25 M. The microfluidics devices described in this document are readily compatible with a broad range of pH values, particularly those suited to biological targets.

A nonexclusive list of possible buffers that may be used according to the invention is as follows: Na-acetate; HEPES; Na-cacodylate; Na-citrate; Na-succinate; Na—K-phosphate; TRIS; TRIS-maleate; imidazole-maleate; bistrispropane; CAPSO, CHAPS, MES, and imidazole.

Additives are small molecules that affect the solubility and/or activity behavior of the target. Such compounds can speed up crystallization screening or produce alternate crystal forms or polymorphs of the target. Additives can take nearly any conceivable form of chemical, but are typically mono and polyvalent salts (inorganic or organic), enzyme ligands (substrates, products, allosteric effectors), chemical crosslinking agents, detergents and/or lipids, heavy metals, organometallic compounds, trace amounts of precipitating agents, and small molecular weight organics.

The following is a nonexclusive list of additives that may be used in accordance with the invention: 2-butanol; DMSO; hexanediol; ethanol; methanol; isopropanol; sodium fluoride; potassium fluoride; ammonium fluoride; lithium chloride anhydrous; magnesium chloride hexahydrate; sodium chloride; calcium chloride dihydrate; potassium chloride; ammonium chloride; sodium iodide; potassium iodide; ammonium iodide; sodium thiocyanate; potassium thiocyanate; lithium nitrate; magnesium nitrate hexahydrate; sodium nitrate; potassium nitrate; ammonium nitrate; magnesium formate; sodium formate; potassium formate; ammonium formate; lithium acetate dihydrate; magnesium acetate tetrahydrate; zinc acetate dihydrate; sodium acetate trihydrate; calcium acetate hydrate; potassium acetate; ammonium acetate; lithium sulfate monohydrate; magnesium sulfate heptahydrate; sodium sulfate decahydrate; potassium sulfate; ammonium sulfate; di-sodium tartrate dihydrate; potassium sodium tartrate tetrahydrate; di-ammonium tartrate; sodium dihydrogen phosphate monohydrate; di-sodium hydrogen phosphate dihydrate; potassium dihydrogen phosphate; di-potassium hydrogen phosphate; ammonium dihydrogen phosphate; di-ammonium hydrogen phosphate; tri-lithium citrate tetrahydrate; tri-sodium citrate dihydrate; tri-potassium citrate monohydrate; diammonium hydrogen citrate; barium chloride; cadmium chloride dihydrate; cobaltous chloride dihydrate; cupric chloride dihydrate; strontium chloride hexahydrate; yttrium chloride hexahydrate; ethylene glycol; Glycerol anhydrous; 1,6 hexanediol; MPD; polyethylene glycol 400; trimethylamine HCl; guanidine HCl; urea; 1,2,3-heptanetriol; benzamidine HCl; dioxane; ethanol; iso-propanol; methanol; sodium iodide; L-cysteine; EDTA sodium salt; NAD; ATP disodium salt; D(+)-glucose monohydrate; D(+)-sucrose; xylitol; spermidine; spermine tetra-HCl; 6-aminocaproic acid; 1,5-diaminopentane diHCl; 1,6-diaminohexane; 1,8-diaminooctane; glycine; glycyl-glycyl-glycine; hexaminecobalt trichloride; taurine; betaine monohydrate; polyvinylpyrrolidone K15; non-detergent sulfo-betaine 195; non-detergent sulfo-betaine 201; phenol; DMSO; dextran sulfate sodium salt; Jeffamine M-600; 2,5 Hexanediol; (+/−)-1,3 butanediol; polypropylene glycol P400; 1,4 butanediol; tert-butanol; 1,3 propanediol; acetonitrile; gamma butyrolactone; propanol; ethyl acetate; acetone; dichloromethane; n-butanol; 2,2,2 trifluoroethanol; DTT; TCEP; nonaethylene glycol monododecyl ether, nonaethylene glycol monolauryl ether; polyoxyethylene (9) ether; octaethylene glycol monododecyl ether, octaethylene glycol monolauryl ether; polyoxyethylene (8) lauryl ether; Dodecyl-β-D-maltopyranoside; Lauric acid sucrose ester; Cyclohexyl-pentyl-β-D-maltoside; Nonaethylene glycol octylphenol ether; Cetyltrimethylammonium bromide; N,N-bis(3-D-gluconamidopropyl)-deoxycholamine; Decyl-β-D-maltopyranoside; Lauryldimethylamine oxide; Cyclohexyl-pentyl-β-D-maltoside; n-Dodecylsulfobetaine, 3-(Dodecyldimethylanimonio)propane-1-sulfonate; Nonyl-β-D-glucopyranoside; Octyl-β-D-thioglucopyranoside, OSG; N,N-Dimethyldecylamine-β-oxide; Methyl 0-(N-heptylcarbamoyl)-α-D-glucopyranoside; Sucrose monocaproylate; n-Octanoyl-β-D-fructofuranosyl-α-D-glucopyranoside; Heptyl-β-D-thioglucopyranoside; Octyl-β-D-glucopyranoside, OG; Cyclohexyl-propyl-β-D-maltoside; Cyclohexylbutanoyl-N-hydroxyethylglucamide; n-decylsulfobetaine, 3-(Decyldimethylammonio)propane-1sulfonate; Octanoyl-N-methylglucamide, OMEGA; Hexyl-β-D-glucopyranoside; Brij 35; Brij 58; Triton X-114; Triton X-305; Triton X-405; Tween 20; Tween 80; polyoxyethylene(6)decyl ether; polyoxyethylene(9)decyl ether; polyoxyethylene(10)dodecyl ether; polyoxyethylene(8)tridecyl ether; Decanoyl-N-hydroxyethylglucamide; Pentaethylene glycol monooctyl ether; 3-[(3-cholamidopropyl)-dimethylammonio]-1-propane sulfonate; 3-[(3-Cholamidopropyl)-dimethylammonio]hydroxy-1-propane sulfonate; Cyclohexylpentanoyl-N-hydroxyethylglucamide; Nonanoyl-N-hydroxyethyglucamide; Cyclohexylpropanol-N-hydroxyethylglucamide; Octanoyl-N-hydroxyethylglucamide; Cyclohexylethanoyl-N-hydroxyethylglucamide; Benzyldimethyldodecyl ammonium bromide; n-Hexadecyl-β-D-maltopyranoside; n-Tetradecyl-β-D-maltopyranoside; n-Tridecyl-β-D-maltopyranoside; Dodecylpoly(ethyleneglycoether); n-Tetradecyl-N,N-dimethyl ammonio-1-propanesulfonate; n-Undecyl-β-D-maltopyranoside; n-Decyl D-thiomaltopyranoside; n-dodecylphosphocholine; α-D-glucopyranoside, β-D-fructofuranosyl monodecanoate, sucrose mono-caprate; 1-s-Nonyl-β-D-thioglucopyranoside; n-Nonyl-β-D-thiomaltoyranoside; N-Dodecyl-N,N-(dimethlammonio)butyrate; n-Nonyl-β-D-maltopyranoside; Cyclohexyl-butyl D-maltoside; n-Octyl-β-D-thiomaltopyranoside; n-Decylphosphocholine; n-Nonylphosphocholine; Nonanoyl-N-methylglucamide; 1-s-Heptyl-β-D-thioglucopyranoside; n-Octylphosphocholine; Cyclohexyl-ethyl D-maltoside; n-Octyl-N,N-dimethyl ammonio-1-propanesulfonate; Cyclohexyl-methyl-β-D-maltoside.

Cryosolvents are agents that stabilize a target crystal to flash-cooling in a cryogen such as liquid nitrogen, liquid propane, liquid ethane, or gaseous nitrogen or helium (all at approximately 100-120° K.) such that crystal becomes embedded in a vitreous glass rather than ice. Any number of salts or small molecular weight organic compounds can be used as a cryoprotectant, and typical ones include but are not limited to: MPD, PEG-400 (as well as both PEG derivatives and higher molecular-weight PEG compounds), glycerol, sugars (xylitol, sorbitol, erythritol, sucrose, glucose, etc.), ethylene glycol, alcohols (both short- and long chain, both volatile and nonvolatile), LiOAc, LiCl, LiCHO$_2$, LiNO$_3$, Li2SO$_4$, Mg(OAc)$_2$, NaCl, NaCHO$_2$, NaNO$_3$, etc. Again, materials from which microfluidics devices in accordance with the present invention are fabricated may be compatible with a range of such compounds.

Many of these chemicals can be obtained in predefined screening kits from a variety of vendors, including but not limited to Hampton Research of Laguna Niguel, Calif., Emerald Biostructures of Bainbridge Island, Wash., and Jena BioScience of Jena, Germany, that allow the researcher to perform both sparse matrix and grid screening experiments. Sparse matrix screens attempt to randomly sample as much of precipitant, buffer, and additive chemical space as possible with as few conditions as possible. Grid screens typically consist of systematic variations of two or three parameters against one another (e.g., precipitant concentration vs. pH). Both types of screens have been employed with success in crystallization trials, and the majority of chemicals and chemical combinations used in these screens are compatible with the chip design and matrices in accordance with embodiments of the present invention. Moreover, current and future designs of microfluidic devices may enable flexible combinatorial screening of an array of different chemicals against a particular target or set of targets, a process that is difficult with either robotic or hand screening. This latter aspect is particularly important for optimizing initial successes generated by first-pass screens.

In addition to chemical variability, a host of other parameters can be varied during crystallization screening. Such parameters include but are not limited to: (1) volume of crystallization trial; (2) ratio of target solution to crystallization solution; (3) target concentration; (4) cocrystallization of the target with a secondary small or macromolecule; (5) hydration; (6) incubation time; (7) temperature; (8) pressure; (9) contact surfaces; (10) modifications to target molecules; and (11) gravity.

Although the discussion below refers to proteins, the particular devices or methods described can also be used or suitably adapted for the crystallization of other types of samples such as those mentioned above (e.g., small molecules, other macromolecules, nanoparticles, colloidal particles, etc.). In one aspect of the present invention, protein crystallization is conducted using miniaturized microbatch conditions. The process consists of two steps. First, plugs are preferably formed wherein the concentrations of the protein, precipitant, and additive are adjusted by varying the relative flow rates of these solutions. This step corresponds to a screening step. Once the optimal concentrations have been found, the flow rates can then be kept constant at the optimal conditions. In this step, plugs are preferably transported through the channel as they form. Second, the flow is preferably stopped once the desired number of plugs are formed. The plugs are then preferably allowed to incubate. In some embodiments according to the invention the flow may be continued, rather than stopped. In those embodiments, the flow is maintained sufficiently slow and the channels are made sufficiently long that plugs spend sufficient time in the channels for crystallization to occur (from tens of minutes to weeks, but may be faster or slower).

In one aspect, upon formation of the plugs, they are trapped using expansions in the channels. The expansions act as dead volume elements while the plugs are being formed in the presence of flow. Thus, the expansions do not interfere with the flow of the plugs through the channel. Once the flow is stopped, surface tension drives plugs into the expansions where surface tension is minimized. The expansions may be, but are not limited to, oval, round, square, rectangular, or star-shaped. In particular, a star-shaped expansion may prevent adherence of the plug or of a crystal to the walls of the expansion. The ratio of the size of the expansion opening to the width of the channel may be varied based on empirical results for a particular set of conditions. FIG. 16 is a schematic illustration of a microfluidic device according to the invention that illustrates the trapping of plugs. In experiments, plugs were sustained in perfluorodecaline inside a channel for one day, and did not appear to change during that time (a refractive index mismatch between the fluorinated and aqueous phase was introduced to aid in visualization of plugs).

The method described above allows a high degree of control over protein and precipitant concentrations. It also allows a high degree of control over a range of time scales through the control of plug size and composition. FIG. 17 shows a schematic of a microfluidic method for forming plugs with variable compositions for protein crystallization. Continuously varied flow rates of the incoming streams are preferably used to form plugs with various concentrations of the protein, precipitation agents, and additives. In FIG. 17, for example, the following can be introduced into the various inlets: buffers into inlets 171, 172; PEG into inlet 173; salt into inlet 174; solvent into inlet 175; and protein into inlet 176. These various solutions can enter a channel 177 through which a carrier fluid such as perfluorodecaline flows. For example, a 1-meter long channel with a 200×80 $\mu m^2$ cross section can be used to form approximately two hundred 6 nL (nanoliter) plugs. If each plug contains enough protein to form a 40-$\mu m^3$ crystal, 200 trials will consume only about 1.2 µL of approximately 10 mg/mL protein solution (12 µg of protein). About one minute may be sufficient to form plugs in these trials.

In another aspect according to the invention, after plugs are formed as described above for the microbatch system, slow evaporation through a very thin PDMS membrane (or another membrane with slight water permeability) is preferably used for added control over the crystallization process. A slow decrease in the volume of the plug during evaporation is expected to produce a trajectory of the solution through the crystallization phase space similar to that in a vapor diffusion experiment. Hence, this method, in addition to microbatch methods, can be used to miniaturize and optimize vapor diffusion methods.

In the vapor diffusion method, a drop containing protein, stabilizing buffers, precipitants, and/or crystallization agents is allowed to equilibrate in a closed system with a much larger reservoir. The reservoir usually contains the same chemicals minus the protein but at an over all higher concentration so that water preferentially evaporates from the drop. If conditions are right, this will produce a gradual increase in protein concentration such that a few crystals may form.

Vapor diffusion can be performed in two ways. The one most often used is called Hanging Drop Technique. The drop is placed on a glass coverslip, which is then inverted and used to seal a small reservoir in a Linbro Plate. After a period of several hours to weeks, microscopic crystals may form and continue to grow. The other set up is known as Sitting Drop. In this method a drop (usually >10 uL) is placed in a depression in either a Micro Bridge in a Linbro Plate or a glass plate and again placed in a closed system to equilibrate with a much larger reservoir. One usually uses the sitting drop technique if the drop has very low surface tension, making it hard to turn upside down or if the drops need to be larger than 20 uL. Also, in some cases, crystals will grow better using one technique or the other.

In another embodiment, the plugs are preferably formed and transported such that excessive mixing of the protein with the precipitation agent is minimized or prevented. For example, gentle mixing using spiral channels may be used to achieve this and also to create interfaces between the protein and the precipitation agent. Alternatively, combining two streams of plugs in a T-junction without merging may be used to create plugs that diffuse and combine without significant mixing to establish a free interface after the flow is stopped. Diffusion of the proteins and precipitates through the interface induces crystallization. This is an analogue of the Free-Interface Diffusion method. It may be performed under either the microbatch or vapor diffusion conditions as described above.

Preferably, the spacing between plugs can be increased or the oil composition changed to reduce plug-plug diffusion. For example, a spacing of about 2.5 mm in paraffin oil can be used, which has been shown to be an effective barrier to aqueous diffusion in crystallization trials.

Visually identifying small crystals inside plugs with curved surfaces can be a challenge when performing microbatch experiments. In an aspect according to the invention, a method based on matching the refractive indices of carrier-fluid with that of the plug fluid to enhance visualization is used. Microscopic detection is preferably performed by using shallow channels and by matching the refractive indices of carrier-fluid mixtures to those of the aqueous solutions.

In addition, at least three other novel methods of controlling protein crystallization are described below: (1) using surface chemistry to effect nucleation of protein crystals; (2) using different mixing methods to effect crystallization; and (3) performing protein crystals seeding by separating nucleation and growth phases in space.

Control of nucleation is one of the difficult steps in protein crystallization. Heterogeneous nucleation is statistically a more favorable process than its solution-phase counterpart. Ideal surfaces for heterogeneous nucleation have complementary electrostatic maps with respect to their macromolecular counterparts. Critical nuclei are more stable on such surfaces than in solution. Further, the degree of supersaturation required for heterogeneous nucleation is much less than that required for the formation of solution-phase nuclei. Surfaces such as silicon, crystalline minerals, epoxide surfaces, polystyrene beads, and hair are known to influence the efficiency of protein crystallization. Few studies have been done, but promising results have been shown for protein crystallization at the methyl, imidazole, hydroxyl, and carboxylic acid termini of self-assembled monolayers on gold. Using self-assembled monolayers, proteins were crystallized over a broader range of crystallization conditions and at faster rates than when using the traditional silanized glass.

FIG. 18 is a schematic illustration of a method for controlling heterogeneous nucleation by varying the surface chemistry at the interface of an aqueous plug-fluid and a carrier-fluid. In FIG. 18, plugs are formed in the presence of several solutions of surfactants that possess different functional groups (left side of the diagram). The right side of FIG. 18 shows the aqueous phase region in which a precipitant, solvent, and protein may be introduced into inlets 180, 181, and 182, respectively. The composition of the surfactant monolayer is preferably controlled by varying the flow rates. In another application of the method illustrated in FIG. 18, the surface chemistry can be varied continuously. The manipulation and control of the surface chemistry can be used for screening, assays, crystallizations, and other applications where surface chemistry is important.

In one aspect of the invention, heterogeneous nucleation of proteins is controlled by forming aqueous plugs in a carrier-fluid, preferably containing fluoro-soluble surfactants if the carrier-fluid is a fluorocarbon. Varying the relative flow rates of the surfactant solutions may generate a wide variety of liquid-liquid interface conditions that can lead to the formation of mixed monolayers or mixed phase-separated monolayers. Preferably, several surfactants are used to control the heterogeneous nucleation of protein crystals. Ethylene-glycol monolayers are preferably used to reduce heterogeneous nucleation, and monolayers with electrostatic properties complementary to those of the protein are preferably used to enhance heterogeneous nucleation. These methods for controlling heterogeneous nucleation are designed to induce or enhance the formation of crystals that are normally difficult to obtain. These methods may also be used to induce or enhance the formation of different crystal polymorphs that are relatively more stable or better ordered.

As mentioned above, control of nucleation is highly desired in an advanced crystallization screen. One method that can be used to achieve control of nucleation involves the transfer of nucleating crystals from one concentration to another via dilution. This method, which has been applied in macroscopic systems primarily to vapor diffusion, was intended to allow decoupling of the nucleation and growth phases. This method is difficult to perform using traditional methods of crystallization because nucleation occurs long before the appearance of microcrystals.

FIG. 19 illustrates a method of separating nucleation and growth using a microfluidic network according to the present invention using proteins as a non-limiting example. The left side of FIG. 19 shows plugs that are formed preferably using high concentrations of protein and precipitant. In FIG. 19, the following can be introduced into the various inlets shown: buffer into inlets 191, 196; PEG into inlets 192, 197; precipitant into inlets 193, 198; solvent into inlets 194, 199; and protein into inlets 195, 200. Oil flows through the channels 201, 202 from left to right. The portions 203, 204, and 205 of the channel correspond to regions where fast nucleation occurs (203), no nucleation occurs (204), and where crystal growth occurs (205). The concentrations used are those that correspond to the nucleating region in the phase diagram. Nucleation occurs as the plugs move through the channel to the junction over a certain period. Preferably, these plugs are then merged with plugs containing a protein solution at a point corresponding to a metastable (growth, rather than nucleation) region (right side of FIG. 19). This step ends nucleation and promotes crystal growth. When the combined channel has been filled with merged plugs, the flow is preferably stopped and the nuclei allowed to grow to produce crystals.

Nucleation time can be varied by varying the flow rate along the nucleation channel. The nucleus is preferably used as a seed crystal for a larger plug with solution concentrations that correspond to a metastable region. Existing data indicate the formation of nuclei within less than about 5 minutes.

Fluid mixing is believed to exert an important effect in crystal nucleation and growth. Methods according to the invention are provided that allow a precise and reproducible degree of control over mixing. FIG. 20 illustrates two of these methods. A method of mixing preferably places the solution into a nucleation zone of the phase diagram without causing precipitation. Preferably, gentle mixing (FIG. 20, left side) is used to achieve this by preventing, reducing, or minimizing contact between concentrated solutions of the protein and precipitant. Alternatively, rapid mixing (FIG. 20, right side) is used to achieve this by allowing passage through the precipitation zone sufficiently quickly to cause nucleation but not precipitation. The two methods used as examples involve the use of spiraling channels for gentle mixing and serpentine channels for rapid mixing.

The two methods in accordance with the invention depicted in FIG. 20 can be used to determine the effect of mixing on protein crystallization. In addition, the various methods for controlling mixing described previously (e.g., slow mixing in straight channels, chaotic mixing in non-straight channels, or mixing in which twirling may or may not occur) can be applied to crystallization, among other things.

After obtaining the crystals using any of the above described techniques, the crystals may be removed from the microfluidic device for structure determination. In other systems, the fragile and gelatinous nature of protein crystals makes crystal collection difficult. For example, removing protein crystals from solid surfaces can damage them to the point of uselessness. The present invention offers a solution to this problem by nucleating and growing crystals in liquid environments. In an aspect according to the invention, a thin wetting layer of a carrier-fluid covered with a surfactant is used to enable or facilitate the separation of a growing crystal from a solid surface. When the crystals form, they may be separated from the PDMS layer by using a thin layer of a carrier-fluid.

It will be clear to one skilled in the art that while the above techniques are described in detail for the crystallization of proteins, techniques similar to the ones described above may also be used for the crystallization of other substances, including other biomolecules or synthetic chemicals. In addition, the devices and methods according to the invention may be used to perform co-crystallization. For example, a crystal comprising more than one chemical may be obtained, for example, through the use of at least one stream of protein, a stream of precipitant, and optionally, a stream comprising a third chemical such as an inhibitor, another protein, DNA, etc. One may then vary the conditions to determine those that are optimal for forming a co-crystal.

Particle Separation/Sorting Using Plugs

The flow within the moving plugs can be used for separation of polymers and particles. Plugs can be used for separation by first using flow within a moving plug to establish a distribution of the polymers or particles inside the plug (for example, an excess of the polymer inside the front, back, right or left side of the plug) and then using splitting to separate and isolate the part of the plug containing higher concentration of the polymers or particles. When two polymers or particles are present inside the plug and establish different distributions, splitting can be used to separate the polymers or particles.

The invention is further described below, by way of the following examples. It will be appreciated by persons of ordinary skill in the art that this example is one of many embodiments and is merely illustrative. In particular, the device and method described in this example (including the channel architectures, valves, switching and flow control devices and methods) may be readily adapted, e.g., used in conjunction with one or more devices or methods, so that plugs may be analyzed, characterized, monitored, and/or sorted as desired by a user.

EXAMPLE

Example 1—Fabrication of Microfluidic Devices and a General Experimental Procedure Microfluidic devices with hydrophilic channel surfaces were fabricated using rapid prototyping in polydimethylsiloxane. The channel surfaces were rendered hydrophobic either by silanization or heat treatment. To silanize the surfaces of channels, (tridecafluoro-1,1,2,2-tetrahydrooctyl)-1-trichlorosilane (United Chemical Technologies, Inc.) vapor was applied to the inlets of a device with dry nitrogen as a carrier gas at around 40-60 mm Hg above about 1 atm pressure. Vacuum was simultaneously applied to the outlet of the device at about 650 mm Hg below atmospheric pressure. The silane vapor was applied for a period of between about 1-3 hours. To treat the channels using heat, a device was placed in an oven at approximately 120° C. for about three hours. Alternatively, a device can be heated in a Panasonic "The Genius" 1300 Watt microwave oven at power set to "10" for about ten minutes.

Oils and aqueous solutions were pumped through devices using a kdScientific syringe pump (Model 200) or Harvard Apparatus PhD 2000 pump. Hamilton Company GASTIGHT syringes were used (10-250 µl) and Hamilton Company 30 gauge Teflon® needles were used to attach the syringes to the devices. Oils and aqueous solutions were pumped through devices at volumetric flow rates ranging from about 0.10 µL/min to about 10.0 µL/min.

Aqueous solutions were colored using Crayola Original Formula Markers or Ferroin Indicator (0.025 M, Fisher Scientific). Oils that were used included perfluorodecaline (mixture of cis and trans, 95%, Acros Organics), perfluoroperhydrophenanthrene (tech., Alfa-Aesar), or 1H,1H,2H,2H-perfluorooctanol (98%, Alfa-Aesar). The experiments were typically performed using 10:1 mixtures of perfluorodecaline and 1H,1H,2H,2H-perfluorooctanol.

The experiments were monitored using a Lica MZFLIII stereoscope with Fostec (Schott-Fostec, LLC) Modulamps. Photographs of the experiments were taken with a Spot Insight Color Camera, Model #3.2.0 (Diagnostic Instruments, Inc.). Spot Application version 3.4.0.0 was used to take the photographs with the camera.

Example 2—Varying the Concentration of Aqueous Solutions in Plugs

The left side of each of FIGS. 25A-C shows a schematic diagram of the microfluidic network and the experimental conditions. The right side of each of FIGS. 25A-C shows microphotographs illustrating the formation of plugs using different concentrations of the aqueous streams. Aqueous solutions of food dyes (red/dark and green/light) and water constituted the three streams. The volumetric flow rates of the three solutions (given in µL/min) are indicated. The dark stream is more viscous than the light stream. Therefore, the dark (more viscous) stream moves (measured in mm/s) more slowly and occupies a larger fraction of the channel at a given volumetric flow rate.

Figure 45C:
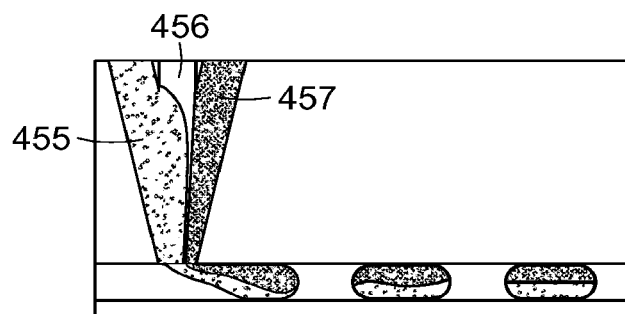
Figure 45D:
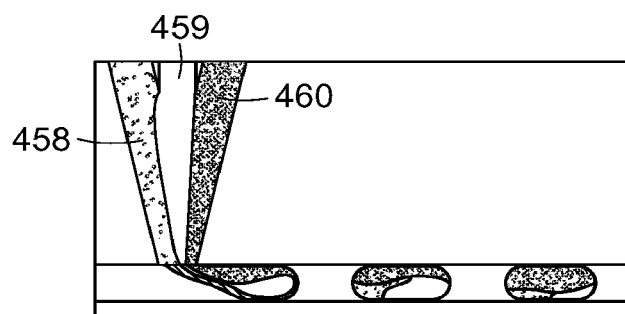

FIG. 45a) shows a schematic of the microfluidic network used to demonstrate that on-chip dilutions can be accomplished by varying the flow rates of the reagents. In FIG. 45a), the reagents are introduced through inlets 451, 453 while the dilution buffer is introduced through inlet 452. An oil stream flows through channel 454. The blue rectangle outlines the field of view for images shown in FIG. 45c)-d).
FIG. 45b) shows a graph quantifying this dilution method by measuring fluorescence of a solution of fluorescein diluted in plugs in the microchannel. Data are shown for 80 experiments in which fluorescein was flowed through one of the three inlets, where $C_{measured}$ and $C_{theoretical}$ [µM] are measured and expected fluorescein concentration. FIG. 45(c) shows photographs illustrating this dilution method with streams of food dyes 455, 456, 457 having flow rates of 45 nL/s, 10 nL/s, and 10 nL/s, respectively. FIG. 45(d) shows photographs illustrating this dilution method with streams of food dyes 458, 459, 460 having flow rates of 10 nL/s, 45 nL/s, and 10 nL/s, respectively. Carrier fluid was flowed at 60 nL/s.

Example 3

Networks of microchannels with rectangular cross-sections were fabricated using rapid prototyping in PDMS. The PDMS used was Dow Corning Sylgard Brand 184 Silicone Elastomer, and devices were sealed using a Plasma Prep II (SPI Supplies). The surfaces of the devices were rendered hydrophobic by baking the devices at 120° C. for 2-4 hours.

In FIG. 26, the red aqueous streams were McCormick® red food coloring (water, propylene glycol, FD&C Red 40 and 3, propylparaben), the green aqueous streams were McCormick® green food coloring (water, propylene glycol, FD&C yellow 5, FD&C blue 1, propylparaben) diluted 1:1 with water, and the colorless streams were water. PFD used was a 10:1 mixture of perfluorodecaline (mixture of cis and trans, 95%, Acros Organics): 1H,1H,2H,2H-perfluorooctanol (Acros Organics). The red aqueous streams were introduced in inlet 260, 265 while the green aqueous streams were introduced in inlets 262, 263 in FIG. 26b). The colorless aqueous stream was introduced in inlets 261, 264. The dark shadings of the streams and plug are due mainly from the red dye while the lighter shadings are due mainly from the green dye.

Aqueous solutions were pumped using 100 µL Hamilton Gastight syringes (1700 series, TLL) or 50 µL SGE gastight syringes. PFD was pumped using 1 mL Hamilton Gastight syringes (1700 series, TLL). The syringes were attached to microfluidic devices by means of Hamilton Teflon needles (30 gauge, 1 hub). Syringe pumps from Harvard Apparatus (PHD 2000 Infusion pumps; specially-ordered bronze bushings were attached to the driving mechanism to stabilize pumping) were used to infuse the aqueous solutions and PFD.

Microphotographs were taken with a Leica MZ12.5 stereomicroscope and a SPOT Insight Color digital camera (Model #3.2.0, Diagnostic Instruments, Inc.). SPOT Advanced software (version 3.4.0 for Windows, Diagnostic Instruments, Inc.) was used to collect the images. Lighting was provided from a Machine Vision Strobe X-Strobe X1200 (20 Hz, 12 µF, 600V, Perkin Elmer Optoelectronics). To obtain an image, the shutter of the camera was opened for 1 second and the strobe light was flashed once with the duration of the flash being about 10 µs.

Images were analyzed using NIH Image software, Image J. Image J was used to measure periods and lengths of plugs from microphotographs such as shown in FIG. 27b). Periods corresponded to the distance from the center of one plug to the center of an adjacent plug, and the length of a plug was the distance from the extreme front to the extreme back of the plug (see FIG. 28 for the definitions of front and back). Measurements were initially made in pixels, but could be converted to absolute measurements by comparing them to a measurement in pixels of the 50 µm width of the channel.

To make measurements of the optical intensity of $Fe(SCN)_x^{(3-x)+}$ complexes in plugs, microphotographs were converted from RGB to CMYK color mode in Adobe Photoshop 6.0. Using the same program, the yellow color channels of the microphotographs were then isolated and converted to grayscale images, and the intensities of the grayscale images were inverted. The yellow color channel was chosen to reduce the intensity of bright reflections at the extremities of the plugs and at the interface between the plugs and the channel. Following the work done in Photoshop, regions of plugs containing high concentrations of $Fe(SCN)_x^{(3-x)+}$ complexes appeared white while regions of low concentration appeared black. Using Image J, the intensity was measured across a thin, rectangular region of the plug, located halfway between the front and back of the plug (white dashed lines in FIG. 27a1)). The camera used to take the microphotographs of the system was not capable of making linear measurements of optical density. Therefore, the measurements of intensity were not quantitative. Several of the plots of intensity versus relative position across the channel (FIG. 27c) were shifted vertically by less than 50 units of intensity to adjust for non-uniform illuminations of different parts of the images. These adjustments were justified because it was the shape of the distribution that was of interest, rather than the absolute concentration.

FIG. 29a)-b) shows plots of the sizes of periods and sizes of plugs as a function of total flow velocity (FIG. 29a)) and water fraction (wf) (FIG. 29b)). Values of capillary number (C.n.) were 0.0014, 0.0036, 0.0072 and 0.011, while values of the Reynolds number ($R_e$) were 1.24, 3.10, 6.21, and 9.31, each of the C.n. and $R_e$ value corresponding to a set of data points with water fractions (wf) 0.20, 0.52, 0.52, and 0.20 (the data points from top to bottom in FIG. 29A)). In turn, each of these sets of data points corresponds to a particular flow velocity as shown in FIG. 29a). Plugs in FIG. 29b) travel at about 50 millimeter/second (mm/s). All measurements of length and size are relative to the width of the channels (50 µm).

FIG. 30 shows microphotographs illustrating weak dependence of periods, length of plugs, and flow patterns inside plugs on total flow velocity. The left side of FIG. 30 shows a diagram of the microfluidic network. Here, the same solutions were used as in the experiment corresponding to FIG. 27. The $Fe(SCN)_x^{(3-x)+}$ solution was introduced into inlet 301 while the colorless aqueous streams were introduced into inlets 302, 303. The same carrier fluid as used in the FIG. 27 experiment was flowed into channel 304. The right side of FIG. 30 shows microphotographs of plugs formed at the same water fraction (0.20), but at different total flow velocities (20, 50, 100, 150 mm/s from top to bottom). Capillary numbers were 0.0014, 0.0036, 0.0072, and 0.011, respectively, from top to bottom. Corresponding Reynolds numbers were 1.24, 3.10, 6.21, and 9.31.

FIG. 31A-C are plots showing the distribution of periods and lengths of plugs where the water fractions were 0.20, 0.40, and 0.73, respectively. The total flow velocity was about 50 mm/s, C.n.=0.0036, $R_e$=3.10 in all cases.

FIG. 27 shows the effects of initial conditions on mixing by recirculating flow inside plugs moving through straight microchannels. FIG. 27a1) shows that recirculating flow (shown by black arrows) efficiently mixed solutions of reagents that were initially localized in the front and back halves of the plug. Notations of front, back, left, and right are the same as that in FIG. 28. FIG. 27a2) shows that recirculating flow (shown by black arrows) did not efficiently mix solutions of reagents that were initially localized in the left and right halves of the plugs. The left side of FIG. 27b) shows a schematic diagram of the microfluidic network. The two colorless aqueous streams were introduced into inlets 271, 272 while a carrier fluid in the form of perfluorodecaline flowed through channel 273. These solutions did not perturb the flow patterns inside plugs.

The right side of FIG. 27b) shows microphotographs of plugs of various lengths near the plug-forming region of the microfluidic network for water fractions of from 0.14 up to 1.00. FIG. 27c1) shows a graph of the relative optical intensity of $Fe(SCN)_x^{(3-x)+}$ complexes in plugs of varying lengths. The intensities were measured from left (x=1.0) to right (x=0.0) across the width of a plug (shown by white dashed lines in FIG. 27a1)-a2)) after the plug had traveled 4.4 times its length through the straight microchannel. The gray shaded areas indicate the walls of the microchannel. FIG. 27c2) is the same as FIG. 27c1) except that each plug had traversed a distance of 1.3 mm. The d/l of each water fraction (wf) were 15.2 (wf 0.14), 13.3 (wf 0.20), 11.7 (wf 0.30), 9.7 (wf 0.40), 6.8 (wf 0.60), 4.6 (wf 0.73), and 2.7 (wf 0.84), where d is the distance traveled by the plug and l is the length of the plug.

Example 4—Merging of Plugs

Experiments were conducted to investigate the merging of plugs using different channel junctions (T- or Y-shaped), cross-sections, and flow rates (see FIG. 33a-d). The figures on the left side of FIGS. 33a-d show top views of microfluidic networks that comprise channels having either uniform or nonuniform dimension (e.g., the same or different channel diameters). The corresponding figures on the right are microphotographs that include a magnified view of two plug streams (from the two separate channels portions of which form the branches of the Y-shaped junction) that merges into a common channel.

In FIG. 33a, the oil-to-water volumetric ratio was 4:1 in each pair of oil and water inlets. The oil streams were introduced into inlets 330, 332, while the aqueous streams were introduced into inlets 331, 333. The flow rates of the combined oil/water stream past the junction where the oil and water meet was 8.6 mm/s. The channels, which were rectangular, had dimensions of 50 (width)×50 (height) µm². As shown in FIG. 33a, plugs that flow in uniform-sized channels typically merged only when they simultaneously arrived at the T-junction. Thus, plug merging in these channels occur infrequently. In addition, lagging plugs were typically not able to catch up with leading plugs along the common channel.

FIG. 33b illustrates plug merging occurring between plugs arriving at different times at the Y-shaped junction (magnified view shown). The oil streams were introduced into inlets 334, 336, while the aqueous streams were introduced into inlets 335, 337. In FIG. 33b, the flow rates for the combined oil/water fluid past the junction where the oil and water meet were 6.9 mm/s for channel 346 (the 50×50 µm² channel) and 8.6 mm/s for channel 347 (the 25×50 µm² channel). The oil-to-water volumetric ratio was 4:1 in each pair of oil and water inlets. The two channels (the branch channels) merged into a common channel 348 that had a 100×50 µm² cross-section. As shown in the figure, the larger plugs from the bigger channel are able to merge with the smaller plugs from the narrower channel even when they do not arrive at the junction at the same time. This is because lagging larger plugs are able to catch up with the leading smaller plugs once the plugs are in the common channel.

FIG. 33c depicts in-phase merging (i.e., plug merging upon simultaneous arrival of at least two plugs at a junction)

of plugs of different sizes generated using different oil/water ratios at the two pairs of inlets. The oil streams were introduced into inlets 338, 340, while the aqueous streams were introduced into inlets 339, 341. The flow rate corresponding to the fluid stream through channel 349 resulting from a 1:1 oil-to-water volumetric ratio was 4.0 mm/s, while that through channel 350 corresponding to the 4:1 oil-to-water volumetric ratio was 6.9 mm/s. Each branch channel of the Y-shaped portion of the network (magnified view shown) had a dimension of 50×50 μm² while the common channel 351 (the channel to which the branch channels merge) was 125×50 μm².

FIG. 33*d* illustrates defects (i.e., plugs that fail to undergo merging when they would normally merge under typical or ideal conditions) produced by fluctuations in the relative velocity of the two incoming streams of plugs. The oil streams were introduced into inlets 342, 344, while the aqueous streams were introduced into inlets 343, 345. In this experiment, the flow rate corresponding to the fluid stream through channel 352 resulting from a 1:1 oil-to-water volumetric ratio was 4.0 mm/s, while that through channel 353 corresponding to the 4:1 oil-to-water volumetric ratio was 6.9 mm/s. Each branch channel that formed one of the two branches of the Y-shaped intersection (magnified view shown) was 50×50 μm² while the common channel 354 (the channel to which the two branch channels merge) is 125×50 μm².

Example 5—Splitting Plugs Using a Constricted Junction

The splitting of plugs was investigated using a channel network with a constricted junction. In this case, the plugs split and flowed past the junction into two separate branch channels (in this case, branch channels are the channels to which a junction branches out) that are at a 180°-angle to each other (see FIGS. 34*a-c* each of which show a channel network viewed from the top). In these experiments, the outlet pressures, $P_1$ and $P_2$, past the constricted junction were varied such that either P1≈P2 (FIG. 34*b*) or $P_1 < P_2$ (FIG. 34*c*). Here, the relative pressures were varied by adjusting the relative heights of the channels that were under pressures $P_1$ and $P_2$. Since longer plugs tend to split more reliably, this branching point (or junction) was made narrower than the channel to elongate the plugs. FIG. 34*a* shows a schematic diagram of the channel network used in the experiment. The oil and water were introduced into inlets 3400 and 3401, respectively. The oil-to-water ratio was 4:1 while the flow rate past the junction where the oil and water meet was 4.3 mm/s.

FIG. 34*b* is a microphotograph showing the splitting of plugs into plugs of approximately one-half the size of the initial plugs. The channels 3404, which were rectangular, had a cross-section that measured 50×50 μm². The constricted section of the channel 3402 right next to the branching point measured 25×50 μm². The outlet pressures, $P_1$ and $P_2$, were about the same in both branch channels. Here, the plugs split into plugs of approximately the same sizes.

FIG. 34*c* is a microphotograph showing the asymmetric splitting of plugs (i.e., the splitting of plugs into plugs of different sizes or lengths) which occurred when $P_1 < P_2$. The microphotograph shows that larger plugs (somewhat rectangular in shape) flowed along the channel with the lower pressure $P_1$; while smaller plugs (spherical in shape) flowed along the channel with the higher pressure $P_2$. As in FIG. 34*b*, each of the channel 3405 cross-section measured 50×50 μm². The constricted section of the channel 3403 at the junction measured 25×50 μm².

Example 6—Splitting Plugs without Using a Constricted Junction

The splitting of plugs was investigated using a channel network without a constriction such as the one shown in FIGS. 35*b-c*. The channel network used was similar to that shown in FIG. 34(*a*) except that here the plugs split and flowed past the junction in two separate channels at a 90°-angle to each other (the plug flow being represented by arrows). The oil and aqueous streams (4:1 oil:aqueous stream ratio) were introduced into inlets 3500 and 3501, respectively. An oil-only stream flowed through channel 3502. All channels had a cross-section of 50×50 μm². The flow rate used was 4.3 mm/s. FIGS. 35*a-c*, which represent top views of a channel network, show that plugs behave differently compared to the plugs in Example 3 when they flow past a junction in the absence of a channel constriction, such as a constriction shown in FIGS. 35*b-c*. As FIG. 35*c* shows, when $P_1 < P_2$, the plugs remained intact after passing through the junction. Further, the plugs traveled along the channel that had the lower pressure ($P_1$ in FIG. 35*c*) while the intervening oil stream split at the junction. The splitting of the oil stream at the junction gives rise to a shorter separation between plugs flowing along the channel with pressure $P_1$ compared to the separation between plugs in the channel upstream of the branching point or junction.

Example 7—Monitoring Autocatalytic Reactions Using a Microfluidic System

FIG. 37 illustrates the design of an experiment involving chemical amplification in microfluidic devices according to the invention that involves an investigation of a stochastic autocatalytic reaction. This example illustrates how the devices of the present invention can be used to study the acid-sensitive autocatalytic reaction between $NaClO_2$ and $NaS_2O_3$. On the left side of the microfluidic network, a three-channel inlet introduces an aqueous stream through channel 3702, an ester through channel 3701, and an esterase through channel 3703. Oil flowed through channels 3713, 3714. The reaction between ester and esterase yield plugs 3704 that contain a small amount of acid. On the right side of the microfluidic network, the five-channel inlet introduces $NaClO_2$ through inlet 3705, an aqueous stream through inlet 3706, a pH indicator through inlet 3707, a second aqueous stream through inlet 3708, and NaS2O3 through channel 3709. A carrier fluid flows through channels 3713, 3714. Unstirred mixtures of $NaClO_2$ and $NaS_2O_3$ are highly unstable and even a slight concentration fluctuation within that mixture leads to rapid decomposition. Thus, the plugs 3710 containing $NaClO_2/NaS_2O_3$ mixture must not only be quickly mixed but also promptly used after formation. In this proposed experiment, the curvy channels promote chaotic mixing. When a slightly acidic plug of the ester-esterase reaction is merged with a plug of an unstable $NaClO_2/NaS_2O_3$ mixture at the contact region 3712, an autocatalytic reaction will generally be triggered. Upon rapid mixing of these two plugs, the resulting plugs 3711 become strongly acidic. The pH indicator introduced in the five-channel inlet is used to visualize this entire amplification process.

Example 8—Using Chemical Reactions as Highly Sensitive Autoamplifying Detection Elements in Microfluidic Devices In one aspect according to the invention, a sequential amplification using controlled autocatalytic systems is used to amplify samples that contain single molecules of autocatalysts into samples containing a sufficiently high concentration of an autocatalyst such that the amplified autocatalyst can be detected with the naked eye can be detected with the naked eye. Although systems displaying stochastic behavior are expected to display high sensitivity and amplification, various autocatalytic systems can be used in accordance with the invention. A sequential amplification using the microfluidic devices according to the invention can be illustrated using a reaction that has been characterized analytically: the autocatalytic decomposition of violet bis[2-(5-bromo-pyridylazo)-5-(N-propyl-N-sulfopropyl-amino-phenolato]cobaltate, (Co(III)-5-Br-PAPS), upon oxidation with potassium peroxomonosulfate to produce colorless $Co^{2+}$ ions. Here, the $Co^{2+}$ ions serve as the autocatalyst (the order of autocatalysis, m, has not been established for this reaction).

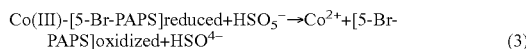
(3)

Addition of small amounts of $Co^{2+}$ to the violet mixture of (Co(III)-5-Br-PAPS) and peroxomonosulfate produces an abrupt loss of color to give a colorless solution. The time delay before this decomposition depends on the amount of the $Co^{2+}$ added to the solution. This reaction has been used to detect concentrations of $Co^{2+}$ as low as about $1\times10^{-10}$ mole/L. The reaction shows good selectivity in the presence of other ions (V(V), Cr(III), Cr(VI), Mn(II), Fe(II), Ni(II), Cu(II) and Zn(II)).

To use this reaction for amplification, a microfluidic network as shown in FIG. 38 is preferably used. An unstable solution of Co(III)-[5-Br-PAPS]reduced and peroxomonosulfate at pH=7 buffer in large plugs are preferably formed in a channel. These large plugs are preferably split in accordance with the invention into three different sizes of plugs. Preferably, the plug sizes are $(1 \ \mu m)^3 = 10^{-15}$ L in the first channel; $(10 \ \mu m)^3 = 10^{-12}$ L in the second channel; and $(100 \ \mu m)^3 = 10^{-9}$ L in the third channel. A three-step photolithography is preferably used in the fabrication of masters for these microfluidic channels.

Example 9—Multi-Stage Chemical Amplification in Microfluidic Devices for Single Molecule Detection FIG. 38 illustrates a method for a multi-stage chemical amplification for single molecule detection using microfluidic devices according to the invention. This example illustrates the use of an autocatalytic reaction between Co(III)-5-Br-PAPS (introduced through inlet 3803) and KHSO5 (introduced through inlet 3801) in a pH=7 buffer (introduced through inlet 3802) that is autocatalyzed by $Co^{2+}$ ions. Oil streams are allowed to flow through channels 3804, 3805. This reaction mixture (contained in plugs 3811) is unstable and decomposes rapidly (shown in red) when small amounts of $Co^{2+}$ 3810 are added. Thus, this reaction mixture is preferably mixed quickly and used immediately. The reaction mixture is preferably transported through the network in $(1 \ \mu m)^3$, $(10 \ \mu m)^3$, $(100 \ \mu m)^3$ size plugs. On the left side of the microfluidic network, the approximately 1 $\mu m^3$ plugs of the sample to be analyzed form at a junction of two channels (shown in green). The merging of plugs containing $Co^{2+}$ ions and plugs containing the reaction mixture results in a rapid autocatalytic reaction. By using an amplification cascade in which larger and larger plugs of the reaction mixture are used for amplification, each $Co^{2+}$ ion in a plug can be amplified to about $10^{10}$ $Co^{2+}$ ions per plug. The result of amplification is visually detectable.

The $(10 \ \mu m)^3$ plugs are preferably merged with larger $(100 \ \mu m)^3$ plugs in the third channel to give approximately $4\times10^{-8}$ mole/L solution of $Co^{2+}$ ions. Autocatalytic decomposition in the approximately $10^{-9}$ L plugs will produce plugs 3809 with about $2.4\times10^{10}$ $Co^{2+}$ ions ($4\times10^{-5}$ mole/L). The flow rates in this system are preferably controlled carefully to control the time that plugs spend in each branch. The time provided for amplification is preferably long enough to allow amplification to substantially reach completion, but short enough to prevent or minimize slow decomposition.

Using different plug sizes is advantageous when merging plugs. Plugs with a size of about $(1 \ \mu m)^3$ are preferably formed by flowing a sample containing about $3\times10^{-9}$ mole/L $Co^{2+}$ through channel 3806. This reaction can be used to detect $Co^{2+}$ at this, or lower, concentration (Endo et al., "Kinetic determination of trace cobalt(II) by visual autocatalytic indication," Talanta, 1998, vol. 47, pp. 349-353; Endo et al., "Autocatalytic decomposition of cobalt complexes as an indicator system for the determination of trace amounts of cobalt and effectors," Analyst, 1996, vol. 121, pp. 391-394.). These plugs have a corresponding volume of about $10^{-15}$ L and carry just a few cobalt ions, on average about 1.8 ions per plug (corresponding to a Poisson distribution). These plugs 3810 are preferably merged with the $(1 \ \mu m)^3$ plugs 3811 containing the Co(III)-5-Br-PAPS/peroxomonosulfate mixture (about $4\times10^{-5}$ mole/L).

Upon autocatalytic decomposition of the complex, the number of $Co^{2+}$ ions in the merged plug 3807 will increase by a factor of between about 104 to $1.2\times104$ $Co^{2+}$ ions ($2\times10^{-5}$ mole/L in 2 $\mu m^3$). These plugs 3807 are preferably merged with the $(10 \ \mu m)^3$ plugs 3811 containing the unstable mixture (about $4\times10^{-5}$ mole/L). The concentration of $Co^{2+}$ ions in these approximately $10^{-12}$ L plugs is preferably about $2\times10^{-8}$ mole/L, which is sufficient to induce autocatalytic decomposition. The number of $Co^{2+}$ ions will increase by a factor of between about $10^3$ to about $2.4\times10^7$ ions/plug in plugs 3808. The starting solution is dark violet ($\varepsilon=9.8\times10^4$ L $mol^{-1}$ $cm^{-1}$ for Co(III)-5-Br-PAPS). Channels are preferably designed to create an optical path through at least ten consecutive 100 $\mu m$ plugs. These plugs will provide an approximately 1-mm long optical path, with absorbance of the starting $4\times10^{-5}$ mole/L solution of about 0.4. This absorbance can be detected by an on-chip photodetector or with the naked eye. If $Co^{2+}$ is present in the sample solution, an autocatalytic cascade will result in the disappearance of the color of the reaction mixture.

At low concentrations of $Co^{2+}$ in the sample, the system may show stochastic behavior, that is, not every $Co^{2+}$ ion would give rise to a decomposition cascade. However, the attractive feature of this system is that thousands of tests can be carried out in a matter of seconds, and statistics and averaging can be performed. Preferably, a sequence of controlled autocatalytic amplification reactions leads to a visual detection of single ions.

Example 10—Enzyme Kinetics

A microfluidic chip according to the invention was used to measure millisecond single-turnover kinetics of ribonuclease A (RNase A; EC 3.1.27.5), a well-studied enzyme. Sub-microliter sample consumption makes the microfluidic chip especially attractive for performing such measurements because they require high concentrations of both the enzyme and the substrate, with the enzyme used in large excess.

The kinetic measurements were performed by monitoring the steady-state fluorescence arising from the cleavage of a fluorogenic substrate by RNase A as the reaction mixture flowed down the channel (see FIG. 40(a)). In FIG. 40, a substrate, buffer, and RNase A were introduced into inlets 401, 401, and 403, respectively. A carrier fluid flowed through channel 404. The amount of the product at a given reaction time t [s] was calculated from the intensity of fluorescence at the corresponding distance point d [m] (t=d/U where U=0.43 m/s is the velocity of the flow). The channels were designed to wind so that rapid chaotic mixing was induced, and were designed to fit within the field of view of the microscope so that the entire reaction profile could be measured in one spatially resolved image. Selwyn's test (Duggleby, R. G., Enzyme Kinetics and Mechanisms, Pt D; Academic Press: San Diego, 1995, vol. 249, pp. 61-90; Selwyn, M. J. Biochim. Biophys. Acta, 1965, vol. 105, pp. 193-195) was successfully performed in this system to establish that there were no factors leading to product inhibition or RNase A denaturation.

The flow rate of the stock solution of 150 µM of RNase A was kept constant to maintain 50 µM of RNase A within the plugs. By varying the flow rates of the buffer and substrate (see FIG. 45), progress curves were obtained for eight different substrate concentrations. For [E]o>>[S]o, the simple reaction equation is [P]t=[S]o(1−Exp(−kt)), where [E]o is the initial enzyme concentration, [S]o is the initial substrate concentration, [P]t is the time-dependent product concentration and k [s$^{-1}$] is the single-turnover rate constant. To obtain a more accurate fit to the data, the time delay Δtn required to mix a fraction of the reaction mixture $f_n$ was accounted for.

An attractive feature of the microfluidic system used is that the reaction mixture can be observed at time t=0 (there is no dead-time). This feature was used to determine Δtn and fn in this device by obtaining a mixing curve using fluo-4/Ca$^{2+}$ system as previously described (Song et al., Angew. Chem. Int. Ed. 2002, vol. 42, pp.

$$[P]_t = \sum_n f_n [S]_0 (1 - \mathrm{Exp}(-k(t - \Delta t_n)))$$

768-772), and correcting for differences in diffusion constants (Stroock et al., Science, 2002, vol. 295, pp. 647-651). All eight progress curves gave a good fit with the same rate constant of 1100±250 s$^{-1}$. The simpler theoretical fits gave indistinguishable rate constants. These results are in agreement with previous studies, where cleavage rates of oligonucleotides by ribonucleases were shown to be ~10$^3$ s$^{-1}$.

Thus, this example demonstrates that millisecond kinetics with millisecond resolution can be performed rapidly and economically using a microchannel chip according to the invention. Each fluorescence image was acquired for 2 s, and required less than 70 nL of the reagent solutions. These experiments with stopped-flow would require at least several hundreds of microliters of solutions. Volumes of about 2 µL are sufficient for ~25 kinetic experiments over a range of concentrations. Fabrication of these devices in PDMS is straightforward (McDonald, et al., Accounts Chem. Res. 2002, vol. 35, pp. 491-499) and no specialized equipment except for a standard microscope with a CCD camera is needed to run the experiments. This system could serve as an inexpensive and economical complement to stopped-flow methods for a broad range of kinetic experiments in chemistry and biochemistry.

Example 11—Kinetics of RNA Folding

The systems and methods of the present invention are preferably used to conduct kinetic measurements of, for example, folding in the time range from tens of microseconds to hundreds of seconds. The systems and methods according to the invention allow kinetic measurements using only small amounts of sample so that the folding of hundreds of different RNA mutants can be measured and the effect of mutation on folding established. In one aspect according to the invention, the kinetics of RNA folding is preferably measured by adding Mg$^{2+}$ to solutions of previously synthesized unfolded RNA labeled with FRET pairs in different positions. In accordance with the invention, the concentrations of Mg$^{2+}$ are preferably varied in the 0.04 to 0.4 µM range by varying the flow rates (see, for example, FIGS. 25a)-c)) to rapidly determine the folding kinetics over a range of conditions. The ability to integrate the signal over many seconds using the steady-flow microfluidic devices according to the invention can further improve sensitivity.

As shown in FIGS. 25a)-c), the concentrations of aqueous solutions inside the plugs can be controlled by changing the flow rates of the aqueous streams. In FIGS. 25a)-c), aqueous streams were introduced into inlets 251-258 wherein flow rates of about 0.6 µL/min for the two aqueous streams and 2.7 µL/min was used for the third stream. The stream with the 2.7 µL/min volumetric flow rate was introduced in the left, middle, and right inlet in FIGS. 25a)-c), respectively. A carrier fluid in the form of perfluorodecaline was introduced into channel 259, 260, 261. The corresponding photographs on each of the right side of FIGS. 25a)-c) illustrate the formation of plugs with different concentrations of the aqueous streams. The various shadings inside the streams and plugs arise from the use of aqueous solutions of food dyes (red/dark and green/light), which allowed visualization, and water were used as the three streams, the darker shading arising mainly from the red dye color while the lighter shading arising mainly from the green dye color. The dark stream is more viscous than the light stream, therefore it moves slower (in mm/s) and occupies a larger fraction of the channel at a given volumetric flow rate (in µL/min).

Example 12—Nanoparticle Experiments with and without Plugs

FIG. 15 illustrates a technique for the synthesis of CdS nanoparticles 155. In one experiment, nanoparticles were formed in a microfluidic network. The channels of the microfluidic device had 50 µm×50 µm cross-sections. A fluorinated carrier-fluid (10:1 v/v mixture of perfluorohexane and 1H,1H,2H,2H-perfluorooctanol) was flowed through the main channel at 15 µm min$^{-1}$. An aqueous solution, pH=11.4, of 0.80 mM CdCl$_2$ and 0.80 mM 3-mercaptopropionic acid was flowed through the left-most inlet channel 151 at 8 µL min$^{-1}$. An aqueous solution of 0.80 mM polyphosphates Na(PO$_3$)$_n$ was flowed through the central inlet channel 152 at 8 µL min$^{-1}$, and an aqueous solution of 0.96 mM Na$_2$S was flowed through the right-most inlet channel 153 at 8 µL min$^{-1}$. To terminate the growth of nanoparticles, an aqueous solution of 26.2 mM 3-mercaptopropionic acid, pH=12.1, was flowed through the bottom inlet of the device 157 at 24 µM min$^{-1}$. FIG. 15 shows various regions or points along the channel corresponding to regions or points where nucleation 154, growth 158, and termination 156 occurs. Based on the UV-VIS spectrum, substantially monodisperse nanoparticles formed in this experiment.

Nanoparticles were also formed without microfluidics. Solutions of CdCl$_2$, polyphosphates, Na$_2$S, and 3-mercaptopropionic acid, identical to those used in the microfluidics experiment, were used. 0.5 mL of the solution of CdCl$_2$ and 3-mercaptopropionic acid, 0.5 mL of polyphosphates solution, and 0.5 mL of Na$_2$S solution were combined in a cuvette, and the cuvette was shaken by hand. Immediately after mixing, 1.5 mL of 26.2 mM 3-mercaptopropionic acid was added to the reaction mixture to terminate the reaction, and the cuvette was again shaken by hand. Based on the UV-VIS spectrum, substantially polydisperse nanoparticles formed in this experiment.

Example 13—Crystallization

Networks of microchannels were fabricated using rapid prototyping in polydimethylsiloxane (PDMS). The PDMS was purchased from Dow Corning Sylgard Brand 184 Silicone Elastomer. The PDMS devices were sealed after plasma oxidation treatment in Plasma Prep II (SPI Supplies). The devices were rendered hydrophobic by baking the devices at 120° C. for 2-4 hours. Microphotographs were taken with a Leica MZ12.5 stereomicroscope and a SPOT Insight color digital camera (Model #3.2.0, Diagnostic Instruments, Inc.). Lighting was provided from a Machine Vision Strobe X-strobe X1200 (20 Hz, 12 µF, 600V, Perkin Elmer Optoelectronics). To obtain an image, the shutter of the camera was opened for 1 second and the strobe light was flashed once with the duration of approximately 10 µs.

Aqueous solutions were pumped using 10 µl or 50 µl Hamilton Gastight syringes (1700 series). Carrier-fluid was pumped using 50 µl Hamilton Gastight syringes (1700 series). The syringes were attached to microfluidic devices by means of Teflon tubing (Weico Wire & Cable Inc., 30 gauge). Syringe pumps from Harvard Apparatus (PHD 2000) were used to inject the liquids into microchannels.

A. Microbatch Crystallization in a Microfluidic Channel

Microbatch crystallization conditions can be achieved. This experiment shows that size of plugs can be maintained and evaporation of water prevented. In this case, the PDMS device has been soaked in water overnight before the experiment in order to saturate PDMS with water. The device was kept under water during the experiment. During the experiment, the flow rates of carrier-fluid and NaCl solution were 2.7 µL/min and 1.0 µL/min, respectively. The flow was stopped by cutting off the Teflon tubing of both carrier-fluid and NaCl solution.

FIG. 16 shows a schematic illustration of a microfluidic device according to the invention and a microphotograph of plugs of 1M aqueous NaCl sustained in oil. The carrier-fluid is perfluorodecaline with 2% 1H,1H,2H,2H-perfluorooctanol. Inside a microchannel, plugs showed no appreciable change in size.

B. Vapor Diffusion Crystallization in Microchannels: Controlling Evaporation of Water from Plugs This experiment shows that evaporation of water from plugs can be controlled by soaking devices in water for shorter amounts of time or not soaking at all. The rate of evaporation can be also controlled by the thickness of PDMS used in the fabrication of the device. Evaporation rate can be increased by keeping the device in a solution of salt or other substances instead of keeping the device in pure water.

The plug traps are separated by narrow regions that help force the plugs into the traps.

In this experiment, a composite glass/PDMS device was used. PDMS layer had microchannel and a microscopy slide (Fisher, 35×50-1) was used as the substrate. Both the glass slide and the PDMS were treated in plasma cleaner (Harrick) then sealed. The device was made hydrophobic by first baking the device at 120° C. for 2-4 hours then silanizing it by (tridecafluoro-1,1,2,2-tetrahydrooctyl)-1-trichlorosilane (United Chemical Technologies, Inc.).

During the experiment, a flow of carrier-fluid at 1.0 µL/min was established, then flow of aqueous solution was established at a total rate of 0.9 µL/min. Plug formation was observed inside the microchannel. The flow was stopped approximately 5-10 minutes afterwards by applying a pressure from the outlet and stopping the syringe pumps at the same time.

FIG. 41 shows a microphotograph (middle and right side) of the water plugs region of the microfluidic network. FIG. 41(*b*)-(*c*) show the plugs at time t=0 and t=2 hours, respectively. Red aqueous solution is 50% waterman red ink in 0.5 M NaCl solution. Ink streams were then introduced into inlets 411, 412, 413. An oil stream flowed through channel 414. The carrier-fluid is FC-3283 (3M Fluorinert Liquid) with 2% 1H,1H,2H,2H-perfluorodecanol. This photograph demonstrates that the evaporation of water through PDMS can be controlled, and thus the concentration of the contents inside the drops can be increased (this is equivalent to microbatch crystallization). FIG. 41(*a*) shows a diagram of the microfluidic network.

C. Controlling Shape and Attachment of Water Plugs

During the experiment, a flow of carrier fluid at 1.0 µL/min was established, then flow of aqueous solution was established at a total rate of 2.1 µL/min. Plug formation was observed inside the microchannel. The flow was stopped approximately 5-10 minutes afterwards by applying a pressure from the outlet and stopping the syringe pumps at the same time.

FIG. 39 shows a diagram (left side) of a microfluidic network according to the invention. Aqueous streams were introduced into inlets 3901, 3902, 3903 while an oil stream flowed through channel 3904. FIG. 39 also shows a microphotograph (right side) of the water plug region of the microfluidic network. This image shows water plugs attached to the PDMS wall. This attachment occurs when low concentrations of surfactant, or less-effective surfactants are used. In this case 1H,1H,2H,2H-perfluorooctanol is less effective than 1H,1H,2H,2H-perfluorodecanol. In this experiment the oil is FC-3283 (3M Fluorinert Liquid) with 2% 1H,1H,2H,2H-perfluorooctanol as the surfactant.

D. Examples of Protein Crystallization

During the experiment, a flow of oil at 1.0 µL/min was established. Then the flow of water was established at 0.1 µL/min. Finally flows of lysozyme and precipitant were established at 0.2 µL/min. Plug formation was observed inside the microchannel. The flow of water was reduced to zero after the flow inside the channel became stable. The flow was stopped approximately 5-10 minutes afterwards by applying a pressure from the outlet and stopping the syringe pumps at the same time.

FIG. 36 depicts lysozyme crystals grown in water plugs in the wells of the microfluidic channel. Lysozyme crystals started to appear inside aqueous plugs both inside and outside plug traps in approximately 10 minutes. The image of the three crystals in FIG. 36 was taken 1 hour after the flow was stopped. Lysozyme crystals appear colored because they were observed under polarized light. This is common for protein crystals.

The left side of FIG. 36 is a diagram of a microfluidic network according to the invention while the right side is microphotograph of the crystals formed in plugs in the microfluidic network. A precipitant, lysozyme, and water were introduced into inlets 3601, 3602, and 3603, respectively. Oil was flowed through channel 3604. The lysozyme solution contains 100 mg/ml lysozyme in 0.05 M sodium acetate (pH 4.7); the precipitant solution contains 30% w/v PEG (M.W. 5000), 1.0 M NaCl and 0.05 M sodium acetate (pH 4.7); The carrier-fluid is FC-3283 (3M Fluorinert Liquid) with 10% 1H,1H,2H,2H-perfluoro-octanol. The microchannel device was soaked in FC-3283/H2O for one hour before experiment.

FIG. 32 shows that plug traps are not required for formation of crystals in a microfluidic network. FIG. 32 shows a diagram (left side) of the microfluidic network. A precipitant was introduced into inlet 321, lysozyme was introduced into inlet 322, and an aqueous stream was introduced into inlet 323. Oil was flowed through channel 324. FIG. 32 also shows microphotographs (middle and right side) of lysozyme crystals grown inside the microfluidic channel. The experimental condition is same as in FIG. 36.

Example 14—Oil-Soluble Surfactants for Charged Surfaces

In accordance with the invention, neutral surfactants that are soluble in perfluorinated phases are preferably used to create positively and negatively-charged interfaces. To create charged surfaces, neutral surfactants that can be charged by interactions with water, e.g., by protonation of an amine or a guanidinium group (FIG. 24B), or deprotonation of a carboxylic acid group (FIG. 24C), are preferably used. Preferably, charged surfaces are used to repel, immobilize, or stabilize charged biomolecules. Negatively charged surfaces are useful for handling DNA and RNA without surface adsorption. Preferably, both negatively and positively-charged surfaces are used to control the nucleation of protein crystals. Many neutral fluorinated surfactants with acidic and basic groups (RfC(O)OH, Rf(CH$_2$)$_2$NH$_2$, Rf(CH$_2$)$_2$C(NH)NH$_2$) are available commercially (Lancaster, Fluorochem, Aldrich).

To synthesize oligoethylene-glycol terminated surfactants, a modification and improvement of a procedure based on the synthesis of perfluoro non-ionic surfactants is preferably used. In one aspect, the synthesis relies on the higher acidity of the fluorinated alcohol to prevent the polycondensation of the oligoethylene glycol. The modified synthesis uses a selective benzylation of one of the alcohol groups of oligoethylene glycol, followed by activation of the other alcohol group as a tosylate. A Williamson condensation is then performed under phase transfer conditions followed by a final deprotection step via catalytic hydrogenation using palladium on charcoal.

Example 15—Formation of Plugs in the Presence of Fluorinated Surfactants and Surface Tension The surface tension of the oil/water interface has to be sufficiently high in order to maintain a low value of capillary number, C.n. The fluorosurfactant/water interfaces for water-insoluble fluorosurfactants have not been characterized, but these surfactants are predicted to reduce surface tension similar to that observed in a system involving Span on hexane/water interface (about 20 mN/m). The surface tensions of the aqueous/fluorous interfaces are preferably measured in the presence of fluorosurfactants using the hanging drop method. A video microscopy apparatus specifically constructed for performing these measurements has been used to successfully characterize interfaces. FIG. 24 illustrates the synthesis of fluorinated surfactants containing perfluoroalkyl chains and an oligoethylene glycol head group.

Example 16—Forming Gradients by Varying Flow Rates

FIG. 42 shows an experiment involving the formation of gradients by varying the flow rates. In this experiment, networks of microchannels were fabricated using rapid prototyping in polydimethylsiloxane (PDMS). The width and height of the channel were both 50 µm. 10% 1H,1H,2H,2H-perfluorodecanol in perfluoroperhydrophenanthrene was used as oil. Red aqueous solution prepared from 50% Waterman red ink in 0.5 M NaCl solution was introduced into inlet 421. The oil flowed through channel 424 at 0.5 µl/min. Aqueous streams were introduced into inlets 422, 423. To generate the gradient of ink in the channel, the total water flow rate was gradually increased from 0.03 µl/min to 0.23 µl/min in 20 seconds at a ramp rate of 0.01 µl/min per second. At the same time, ink flow rate was gradually decreased from 0.25 µl/min to 0.05 µl/min in 20 seconds at a ramp rate of −0.01 µl/min per second. The total flow rate was constant at 0.28 µl/min. The established gradient of ink concentration inside the plugs can be clearly seen from FIG. 42: the plugs further from the inlet are darker since they were formed at a higher ink flow rate.

Example 17—Lysozome Crystallization Using Gradients

FIG. 43 illustrates an experiment involving the formation of lysozome crystals using gradients. The channel regions 435, 437 correspond to channel regions with very low precipitant concentration while channel region 436 corresponds to optimal range of precipitant concentration. In this experiment, networks of microchannels were fabricated using rapid prototyping in polydimethylsiloxane (PDMS). The width of the channel was 150 µm and the height was 100 µm. 10% 1H,1H,2H,2H-perfluorodecanol in perfluoroperhydrophenanthrene was used as oil.

During the experiment, a flow of oil through channel 434 at 1.0 µl/min was established. Then the flow of water introduced through inlet 432 was established at 0.2 µl/min. The flows of lysozyme introduced through inlet 431 and precipitant introduced through inlet 433 were established at 0.2 µl/min. Plugs formed inside the channel. To create the gradient, water flow rate was first gradually decreased from 0.35 µl/min to 0.05 µl/min over 45 seconds at a ramp rate of (−0.01 µl/min per 1.5 seconds), then increased back to 0.35 µl/min in 45 seconds at a ramp rate of (0.01 µl/min per 1.5 seconds). At the same time, precipitant flow rate was gradually increased from 0.05 µl/min to 0.35 µl/min in 45 seconds at a ramp rate of (0.01 µl/min per 1.5 seconds), then decreased to 0.05 µl/min in 45 seconds at a ramp rate of (−0.01 µl/min per 1.5 seconds). The flow was stopped by pulling out the inlet tubing immediately after water and precipitant flow rates returned to the starting values. The plugs created in this way contained constant concentration of the protein. but variable concentration of the precipitant: the concentration of the precipitant was lowest in the beginning and the end of the channel, and it peaked in the middle of the channel (the center row). Only the plugs in the middle of the channel have the optimal concentration of precipitant for lysozyme crystallization, as confirmed by observing lysozyme crystals inside plugs in the center row. Visualization was performed under polarized light. Preferably, all flow rates would be varied, not just the precipitant and water.

Example 18—Lysozyme Crystallization in Capillaries Using the Microbatch Analogue Method To grow lysozyme crystal inside plugs within capillaries, a 10 µl Hamilton syringe was filled with 100 mg/ml lysozyme in 0.05 M NaAc buffer (pH4.7) and another 10 μl Hamilton syringe was filled with 30% (w/v) MPEG 5000 with 2.0 M NaCl in 0.05 M NaAc buffer (pH4.7) as precipitant. A 50 μl Hamilton syringe filled with PFP (10% PFO) was the oil supply. All three syringes were attached to the PDMS/capillary device and driven by Harvard Apparatus syringe pumps (PHD2000). The capillary has an inner diameter of 0.18 mm and outer diameter of 0.20 mm. Oil flow rate was 1.0 μl/min and both lysozyme and precipitant solution were at 0.3 μl/min. The channel was filled with oil first. Protein and precipitant streams converged immediately before entering the channel to form plugs. After the capillary (Hampton Research) was filled with the plugs containing lysozyme, the flows were stopped. The capillary was disconnected from the PDMS device, sealed with wax and stored in an incubator (18° C.). A lysozyme crystal appeared within an hour and was stable for at least 14 days without change of size or shape (FIG. 47A).

Example 19—Thaumatin Crystallization in Capillaries Using the Microbatch Analogue Method Experiment 1. A 10 μl Hamilton syringe was filled with 50 mg/ml thaumatin in 0.1 M ADA buffer (pH 6.5) and another 10 μl Hamilton syringe was filled with 1.5 M NaK Tatrate in 0.1 M HEPES (pH 7.0). A 50 μl Hamilton syringe filled with PFP (10% PFO) was the oil supply. All three syringes were attached to the PDMS/capillary device and driven by Harvard Apparatus syringe pumps (PHD2000). The capillary has an inner diameter of 0.18 mm and outer diameter of 0.20 mm. Oil flow rate was 1.0 μl/min and both thaumatin and precipitant solution were at 0.3 μl/min. The channel was filled with oil first. Protein and precipitant streams were mixed immediately before entering the channel to form plugs. After the capillary (Hampton Research) was filled with protein plugs, the flows were stopped. The capillary was cut from the PDMS device, sealed by wax and stored in an incubator (18° C.). The thaumatin crystal appeared in 2-3 days and was stable for at least 45 days without size or shape change (FIG. 47B). Some thaumatin crystals grew at the interface of protein solution and oil, while others appeared to attach to the capillary wall.

Experiment 2. Thaumatin crystals were grown inside a capillary tube using 50 mg/mL thaumatin in 0.1M pH 6.5 ADA buffer and a precipitant solution of 1M Na/K tartrate in a 0.1 M pH 7.5 HEPES buffer. Protein and precipitant solutions were mixed in a 1.4:1 protein:precipitant ratio. A fluorinated carrier fluid was a saturated solution of FSN surfactant in FC3283. The capillary was incubated at 18 degrees C. Tetragonal crystals appeared within 5 days (FIG. 48A, B). X-ray diffraction was performed at BioCARS station 14BM-C at the Advanced Photon Source at Argonne National Laboratory. Beam wavelength was 0.9 A. The final length of a single crystal was estimated at 100-150 microns.

Capillaries were cut to the appropriate length without disturbing crystal-containing plugs, resealed using capillary waz, and mounted on clay-tipped cryoloop holders at a distance of 12+/−5 mm from base to crystal. The holder was placed on the x-ray goniometer. Crystals were centered on the beam. Snapshots were taken using 10 second (thaumatin) exposures. Distance from sample to detector was 150 mm. Diffraction to better than 2.2 A was obtained.

Example 20—Vapor Diffusion Protein Crystallization in Capillaries by an Alternating Droplet System The principle of transferring water inside a capillary from one set of plugs to another set of plugs is illustrated in FIG. 50. Briefly, a 10 μl Hamilton syringe was filled with 0.01 Fe(SCN)3 and another 10 μl Hamilton syringe was filled with 0.1 M Fe(SCN)3 with 2.5 M KNO3. Two 50 μl Hamilton syringes were filled with FMS-121 (Gelest, Inc) (saturated with PFO), which provided the oil supply. All four syringes were attached to the PDMS/capillary device and driven by Harvard Apparatus syringe pumps (PHD2000). The capillary has an inner diameter of 0.18 mm and outer diameter of 0.20 mm. One of the oil inlet channels was between the two aqueous inlets channels to separate the two aqueous streams when forming the alternating plugs. This oil inlet channel was vertical to the main channel and had a flow rate of 2.0 μl/min. The other oil inlet channel had a flow rate of 1.0 μl/min and was parallel to the main channel. Both of the aqueous solutions had a flow rate of 0.5 μl/min. After establishing alternating aqueous droplet streams in the capillary, the flows were stopped, and the capillary was disconnected from the PDMS device, sealed with wax and stored in an incubator at 18° C. The size and color change of the plugs were monitored with a Leica microscope (MZ125) having a color CCD camera (SPOT Insight, Diagnostic Instruments, Inc.).

Following the stoppage of flow and sealing of the capillary tube, plugs containing 0.01 M Fe(SCN)3 in water were yellow, while those containing 0.1 M Fe(SCN)3 and 2.5 M KNO3 in water were red (FIG. 50A). However, FIG. 50B shows that after 5 days, the yellow plugs were reduced in size and were more concentrated, while the red plugs increased in size and were more diluted. This demonstration reflects vapor diffusion conditions in the capillary tube that are predicted to facilitate protein crystallization. This technique can be further adapted to other applications requiring concentration of reagents, such as proteins.

Alternating plugs from two different aqueous solutions may be generated in accordance with several representative geometries as set forth in FIG. 51. In principle, the same oil or different oils may be used in the two oil inlets. One scheme for generating alternating plugs from two different aqueous solutions is depicted in FIG. 51A. In this case, one 10 μl Hamilton syringe was filled with 0.1 Fe(SCN)3, another with 1.5 M NaCl. Two 50 μl Hamilton syringes filled with PFP (with 10% PFO) provided the oil supply. All four syringes were attached to the PDMS device and driven by Harvard Apparatus syringe pumps (PHD2000). Alternatively, multiple solutions can be co-introduced together in each of the two aqueous channels as depicted in FIG. 51B. In each of these two cases one of the oil inlet channels was between the two aqueous inlet channels. This oil inlet channel was used to separate the two aqueous streams into alternating plugs and was vertical to the main channel, having a flow rate of 2.0 μl/min. The other oil inlet channel was parallel to the main channel and had a flow rate of 1.0 μmin. Each of the two aqueous solutions had flow rates of 0.5 μmin. Alternating plugs were found to form in the channel (FIG. 51C).

FIG. 52 illustrates another example of generating alternating plugs from two different aqueous solutions. In this case, one 10 μl Hamilton syringe was filled with 0.1 Fe(SCN)3, the other with 1.5 M NaCl. Two 50 μl Hamilton syringes filled with FMS-121 (saturated with PFO) provided the oil supply. All four syringes were attached to the device and driven by Harvard Apparatus syringe pumps (PT-D2000). One of the oil inlet channels was between the two aqueous inlet channels and was used to separate the two aqueous streams prior to formation of alternating plugs (FIG. 52A). This oil inlet channel was vertical to the main channel and had a flow rate of 1.5 μl/min. The other oil stream had a flow rate of 1.5 µl/min and was parallel to the main channel. Each of the two aqueous solutions had flow rates of 0.5 Alternating plugs were found to form in the channel (FIG. 52B).

Other geometries that can support the formation of alternating plugs are depicted in FIG. 53. Importantly, the flow rates of solutions A and B may be changed in a correlated fashion (FIG. 54). Thus, when the flow rate of solution A1 is increased and solution A2 is decreased, the flow rate of solutions B1 is also increased and solution B2 is also decreased. This principle, depicted in FIG. 54, is useful for maintaining a constant difference in salt concentration between the plugs of stream A and stream B to ensure that transfer from all plugs A to all plugs B occurs at a constant rate.

FIG. 54 provides a schematic illustration of a device for preparing plugs of varying protein concentrations where the flow rates of the A and B streams change in a correlated fashion. In this example, A1 through A3 are for protein solution, buffer and precipitants, such as PEG or salts. Highly concentrated salt solutions are injected through B1~B3. The flow rate ratio of inlet Ai to that of Bi (i=1~3) is maintained constant. Therefore all of the protein plugs will shrink at a rate similar to the salt plugs.

FIG. 54 shows that if the flow rates of corresponding A and B streams are changed in a correlative fashion, the composition of plugs B will reflect the composition of plugs A. Therefore, one can incorporate markers into the B stream plugs to serve as a code for the plugs in the A stream. In other words, absorption/fluorescent dyes or x-ray scattering/absorbing materials can be incorporated in markers in the B streams to facilitate optical or x-ray-mediated quantification so as to provide a read out of relative protein and precipitant concentrations in the A streams. This approach can provide a powerful means for optimizing crystallization conditions for subsequent scale-up experiments.

We claim:

1. A method of forming a plurality of plugs and conducting an autocatalytic reaction in at least one thereof, the method comprising the steps of:
   providing a microfluidic device comprising a substrate having at least a first channel and a second channel intersecting each other at a downstream plug-forming junction;
   introducing to the first channel of the microfluidic device a stream of a first plug fluid containing at least one substrate molecule and a stream of a second plug fluid containing one or more reagents for conducting an autocatalytic reaction with the at least one substrate molecule;
   continuously coflowing the stream of the first plug fluid and the stream of the second plug fluid with one another and through the first channel towards the plug-forming junction such that at least one substrate molecule of the first plug fluid and one or more reagents, of the second plug fluid, for conducting an autocatalytic reaction with the at least one substrate molecule coflow with one another prior to contact with a carrier fluid and prior to plug formation;
   continuously flowing a stream of a carrier fluid comprising an oil immiscible with the streams of first and second plug fluids through the second channel of the microfluidic device towards the plug-forming junction, wherein the carrier fluid comprises a fluorosurfactant that comprises an oligoethylene glycol (OEG) terminal end to which an OEG is linked;
   forming a plurality of plugs comprising a subvolume of the coflowing first and second plug fluids containing the at least one substrate molecule and the one or more reagents, respectively, by partitioning the continuously coflowing streams of first and second plug fluids with the continuously flowing carrier fluid at the plug-forming junction of the first and second channels, each of the plurality of plugs being substantially surrounded by the carrier fluid, wherein at least one of the plurality of plugs comprises at least one substrate molecule and one or more reagents for conducting an autocatalytic reaction with the at least one substrate molecule; and
   providing conditions suitable for the autocatalytic reaction in the at least one plug such that the at least one substrate molecule is amplified.

2. The method of claim 1, wherein the at least one substrate molecule is a single biological molecule.

3. The method of claim 2, wherein the at least one substrate molecule is DNA and the autocatalytic reaction is a polymerase-chain reaction.

4. The method of claim 1, wherein the providing conditions suitable for the autocatalytic reaction step includes heating.

5. The method of claim 1, further comprising the step of providing a detector to detect, analyze, characterize, or monitor one or more properties of the autocatalytic reaction during and/or after it has occurred.

6. The method of claim 1, wherein the oil is fluorinated oil.

7. The method of claim 1, wherein the at least one plug is a merged plug.

8. The method of claim 1, further comprising trapping the at least one plug for a period of time during or after the reaction in an expansion portion in a channel of the microfluidic device positioned downstream of the junction.

9. The method of claim 1, wherein the at least one plug is substantially spherical in shape.

10. The method of claim 1, further comprising a mixing step, wherein the mixing step occurs via a special design of a channel of the microfluidic device positioned downstream of the junction.

11. The method of claim 10, wherein the special design of the channel comprises periodic or aperiodic turns and relevant parameters.

12. The method of claim 11, wherein the relevant parameters are selected from the group comprising channel width, period, radius of curvature, and sequence of turns based on the direction of the turns.

13. The method of claim 1, wherein each of the plurality of plugs is substantially surrounded on all sides by the oil.

14. The method of claim 1, further comprising the step of collecting the plurality of plugs in a segment of tubing or the sample tube through an outlet of the microfluidic device positioned downstream of the junction, wherein the plugs remain separated by the oil.

15. The method of claim 1, further comprising the step of flowing the plurality of plugs and oil into a non-fluorinated channel of the microfluidic device positioned downstream of the junction.

16. The method of claim 15, wherein the oil comprises a fluorinated oil and a fluorinated surfactant comprising a hydrophilic head group, wherein the fluorinated surfactant is present at a concentration such that surface tension at the aqueous fluid/channel wall interface is higher than surface tension at the aqueous fluid/oil interface.

17. The method of claim 1, wherein the fluorosurfactant is of the formula:
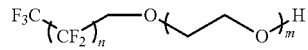
wherein m is 0, 3, 4, 5, or 6; and n is an integer of no less than 16.
* * * * *